United States Patent [19]
Johnson et al.

[11] Patent Number: 6,001,581
[45] Date of Patent: Dec. 14, 1999

[54] CATION-BASED BIOASSAY USING HUMAN METABOTROPIC GLUTAMATE RECEPTORS

[75] Inventors: Edwin C. Johnson; Stephen D. Hess, both of San Diego, Calif.

[73] Assignee: Sibia Neurosciences, Inc., La Jolla, Calif.

[21] Appl. No.: 08/367,264

[22] PCT Filed: Jun. 3, 1994

[86] PCT No.: PCT/US94/06273

§ 371 Date: Jan. 9, 1995

§ 102(e) Date: Jan. 9, 1995

[87] PCT Pub. No.: WO94/29449

PCT Pub. Date: Dec. 22, 1994

Related U.S. Application Data

[63] Continuation-in-part of application No. 08/072,574, Jun. 4, 1993, Pat. No. 5,521,297.

[51] Int. Cl.⁶ ..................... G01N 33/566; C07K 14/705; C12N 15/10
[52] U.S. Cl. ..................... 435/7.21; 435/69.1; 435/325; 530/350; 536/23.5; 436/501
[58] Field of Search ..................... 435/7.2, 69.1, 435/252.3, 325, 7.21, 254.11; 514/44; 536/23.5; 530/350; 436/501

[56] References Cited

U.S. PATENT DOCUMENTS

| | | |
|---|---|---|
| 4,837,148 | 6/1989 | Cregg ..................... 435/172.3 |
| 4,855,231 | 8/1989 | Stroman et al. ..................... 435/68 |
| 4,882,279 | 11/1989 | Cregg ..................... 435/172.3 |
| 4,929,555 | 5/1990 | Cregg et al. ..................... 435/172.3 |
| 5,024,939 | 6/1991 | Gorman ..................... 435/69.1 |
| 5,385,831 | 1/1995 | Mulvihill et al. ..................... 435/69.1 |
| 5,482,835 | 1/1996 | King et al. ..................... 435/6 |
| 5,521,297 | 5/1996 | Daggett et al. ..................... 536/23.5 |
| 5,807,689 | 9/1998 | Daggett et al. ..................... 435/78 |

FOREIGN PATENT DOCUMENTS

| | | |
|---|---|---|
| WO 92/02639 | 8/1991 | WIPO . |
| WO 93/13423 | 12/1992 | WIPO . |

OTHER PUBLICATIONS

Abe et al., "Molecular Characterization of a Novel Metabotropic Glutamate Receptor mGluR5 Coupled to Inositol Phosphate/$Ca^{2+}$ Signal Transduction" *Journal of Biological Chemistry* 267(19):13361–13368 (1992).

Bahouth et al., "Immunological approaches for probing receptor structure and function" *TIPS Reviews* 12:338–343 (1991).

Biel et al., "Another member of the cyclic nucleotide–gated channel family, expressed in testis, kidney and heart" *Procl Natl. Acad. Sci. USA* 91:3505–3509 (1994).

Brabet et al., "Phenylglycine Derivatives Discriminate Between mGluR1-and mGluR5-mediated Responses" *Neuropharmacology* 34(8):895–903 (1995).

Bradford, Marion M., "A Rapid and Sensitive Method for the Quantitation of Microgram Quantities of Protein Utilizing the Principle of Protein-Dye Binding" *Analytical Biochemistry* 72:248–254 (1976).

Bruno et al., "Activation of Metabotropic Glutamate Receptors Coupled to Inositol Phospholipid Hydrolysis Amplifies NMDA–induced Neuronal Degeneration in Cultured Cortical Cells" *Neuropharmacology* 34(8):1089–1098 (1995).

Buisson and Choi, "The Inhibitory mGluR Agonist, s–4–carboxy–3–hydroxy–phenylglycine Selectively Attenuates DMDA Neurotoxicity and Oxygen–Glucose Deprivation–induced Neuronal Death" *Neuropharmacology* 34(8):1081–1087 (1995).

Conquet, F., "Inactivation In Vivo of Metabotropic Glutamate Receptor I by Specific Chromosomal Insertion of Reporter Gene 1acZ" *Neuropharmacology* 34(8):865–870 (1995).

Daggett et al., "Molecular and Functional Characterization of Recombinant Human Metabotropic Glutamate Receptor Subtype 5" *Neuropharmacology* 34(8):871–886 (1995).

Dani and Mayer, "Structure and function of glutamate and nicotinic acetylcholine receptors" *Current Opinion in Neurobiology* 5:310–317 (1995).

Dascal, Nathan, "The Use of Xenopus Oocytes for the Study of Ion Channels" *CRC Critical Reviews in Biochemistry* 22(4):317–387 (1987).

Denhardt et al., "A Membrane–Filter Technique for the Detection of Complementary DNA" *Biochemistry and Biophysical Research Communications* 23(5):641–646 (1966).

Dhallan et al., "Primary structure and functional expression of a cyclic nucleotide–activated channel from olfactory neurons" *Nature* 347:184–187 (1990).

Felder et al., "A Transfected m1 Muscarinic Acetylcholine Receptor Stimulates Adenylate Cyclase via Phosphatidylinositol Hydrolysis" *J. of Biol. Chem.* 264(34):20356–20362 (1989).

Fisher and Aronson, Jr., "Characterization of the cDNA and Genomic Sequence of a G Protein γ Subunit ($\gamma_5$)" *Molecular and Cellular Biol.* 12(4):1585–1591 (1992).

(List continued on next page.)

*Primary Examiner*—Lorraine Spector
*Assistant Examiner*—Claire M. Kaufman
*Attorney, Agent, or Firm*—Gray Cary Ware & Freidenrich, LLP; Stephen E. Reiter

[57] ABSTRACT

In accordance with the present invention, there are provided nucleic acids encoding human metabotropic glutamate receptor subtypes and the proteins encoded thereby. In a particular embodiment, the invention nucleic acids encode mGluR1, mGluR2, mGluR3 and mGluR5 subtypes of human metabotropic glutamate receptors. In addition to being useful for the production of metabotropic glutamate receptor subtypes, these nucleic acids are also useful as probes, thus enabling those skilled in the art, without undue experimentation, to identify and isolate related human receptor subunits. In addition to disclosing novel metabotropic glutamate receptor subtypes, the present invention also comprises methods for using such receptor subtypes to identify and characterize compounds which affect the function of such receptors, e.g., agonists, antagonists, and modulators of glutamate receptor function.

15 Claims, 1 Drawing Sheet

OTHER PUBLICATIONS

Gautam et al., "G protein diversity is increased by associations with a variety of γ subunits" *Proc. Natl. Acad. Sci. USA* 87:7973–7977 (1990).

Gautam et al., "A G Protein Gamma Subunit Shares Homology with ras Proteins" *Science* 244:971–974 (1989).

Grynkiewicz et al., "A New Generation of $Ca^{2+}$ Indicators with Greatly Improved Fluorescence Properties" *J. of Biol. Chem.* 260(6):3440–3450 (1985).

Gubler and Hoffman, "A simple and very efficient method for generating cDNA libraries" *Gene* 25:263–269 (1983).

Gundersen et al., "Glutamate and kainate receptors induced by rat brain messenger RNA in Xenopus oocytes" *Proc. R. Soc. Lond. B* 221:127–143 (1984).

Hurley et al., "Isolation and characterization of a cDNA clone for the γ subunit of bovine retinal transducin" *Proc. Natl. Acad. Sci. USA* 81:6948–6952 (1984).

Ito et al., "Characterization of Prostaglandin $E_2$–Induced $Ca^{2+}$ Mobilization in Single Bovine Adrenal Chromaffin Cells by Digital Image Microscopy" *J. Neurochem.* 56(2):531–540 (1991).

Kaupp et al., "Primary structure and functional expression from complementary DNA of the rod photoreceptor cyclic GMP–gated channel" *Nature* 342:7612–766 (1989).

Kingston et al., "Pharmacological Analysis of 4–Carboxyphenylglycine Derivatives: Comparison of Effects on mGluR1α and mGluR5a Subtypes" *Neuropharmacology* 34(8):887–894 (1995).

Kleuss et al., "Selectivity in Signal Transduction Determined by γ Subunits of Heterotrimeric G Proteins" *Science* 259:832–834 (1993).

Knöpfel et al., "Pharmacological Characterization of MCCG and MAP4 at the mGluR1b, mGluR2 and mGluR4a Human Metabotropic Glutamate Receptor Subtypes" *Neuropharmacology* 34(8):1099–1102 (1995).

Kozak, Marilyn, "Structural Features in Eukaryotic mRNAs That Modulate the Initiation of Translation" *J. Biol. Chem.* 266(30):19867–19870 (1991).

Krieg and Melton, "Functional messenger RNAs are produced by SP6 in vitro transcripton of cloned cDNAs" *Nucleic Acids Research* 12(18):7057–7070 (1984).

Kyte and Doolittle, "A Simple Method for Displaying the Hydropathic Character of a Protein" *J. Mol. Biol.* 157:105–132 (1982).

Linder and Gilman, "G Proteins—Tucked into the internal surface of the cell's outer membrane, these versatile molecules coordinate cellular responses to a multitide of signals that impinge from without" *Scientific American* 56–65 (Jul. 1992).

Masu et al., "Sequence and expression of a metabotropic glutamate receptor" *Nature* 349:760–765 (1991).

Masu et al., "Specific Deficit on the ON Response in Visual Transmission by Targeted Disruption of the mGluR6 Gene" *Cell* 80:757–765 (1995).

Miller, J.H., "Experiment 48: Assay of β–Galactosidase" *Experiments in Molecular Genetics,* (Cold Spring Harbor Laboratory) pp. 352–355 (1972).

Monaghan et al., "The Excitatory Amino Acid Receptors: Their classes, Pharmacology, and Distinct Properties in the Function of the Central Nervous System" *Annu. Rev. Pharmacol. Taxicol.* 29:365–402 (1989).

Nakajima et al., "Direct Linkage of Three Tachykinin Receptors to Stimulation of Both Phosphatidylinositol Hydrolysis and Cyclic AMP Cascades in Transfected Chinese Hamster Ovary Cells" *J. Biol. Chem.* 267(4):2437–2442 (1992).

Nakanishi, Shigetada, "Metabotropic Glutamate Receptors: Synaptic Transmission, Modulation, and Plasticity" *Neuron* 13:1031–1037 (1994).

Nicoletti et al., "The Activation of Inositol Phospholipid Metabolism as a Signal–Transducing System for Excitatory Amino Acids in Primary Cultures of Cerebellar Granule Cells" *J. Neuroscience* 6(7):1905–1911 (1986).

Pin and Bockaert, "Get receptive to metabotropic glutamate receptors" *Current Opinion in Neurobiology* 5:342–349 (1995).

Pin and Duvoisin, "Review: Neurotransmitter receptors I—The Metabotropic Glutamate Receptors: Structure and Functions" *Neuropharmacology* 34(1):1–26 (1995).

Schoepp and True, "1S, 3R–ACPD–sensitive (metabotropic) [$^3$H] glutamate receptor binding in membranes" *Neuroscience Letters* 145:100–104 (1992).

Schoepp et al., "Selective Inhibition of Forskolin–stimulated Cyclic AMP Formation in Rat Hippocampus by a Novel mGluR Agonist, 2R,4R–4–aminopyrrolidine–2,4–dicarboxylate" *Neuropharmacology* 34(8):843–850 (1995).

Simon et al., "Diversity of G Proteins in Signal Transduction" *Science* 252:802–808 (1991).

Sladeczek et al., "Glutamate stimulates inositol phosphate formation in striatal neurones" *Nature* 317:717–719 (1985).

Steiner et al., "Radioimmunoassay for Cyclic Nucleotides—I. Preparation of Antibodies and Iodinated Cyclic Nucleotides" *J. Biol. Chem.* 247(4):1106–1113 (1972).

Stillman and Gluzman, "Replication and Supercoiling of Simian Virus 40 DNA in Cell Extracts from Human Cells" *Molecular and Cellular Biology* 5(8):2051–2060 (1985).

Stühmer, Walter, "Electrophysiological Recording from Xenopus Oocytes" *Methods in Enzymology* 207:319–339 (1992).

Tamir et al., "G–Protein βγ Forms: Identity of β and Diversity of γ Subunits" *Biochemistry* 30:3929–3936 (1991).

Tanabe et al., "A Family of Metabotropic Glutamate Receptors" *Neuron* 8:169–179 (1992).

Urlaub et al., "Effect of Gamma Rays at the Dihydrofolate Reductase Locus: Deletions and Inversions" *Somatic Cell and Molecular Genetics* 12(6):555–566 (1986).

Waechter and Baserga, "Effect of methylation on expression of microinjected genes" *Proc. Natl. Acad. Sci. USA* 79:1106–1110 (1982).

Wickman and Clapham, "G–protein regulation of ion channels" *Current Opinion in Neurobiology* 5:278–285 (1995).

Wigler et al., "DNA–mediated transfer of the adenine phosphoribosyltransferase locus into mammalian cells" *Proc. Natl. Acad. Sci. USA* 76(3):1373–1376 (1979).

Minakami et al, (Mar. 1994), "Molecular cloning and the functional expression of two isoforms of human metabotropic glutamate receptor subtype 5", Biochem. Biophys. Res. Comm. 199(3):1136–43.

Hodgson, Receptor screening and the search for new pharmaceuticals, Bio/Technology, 10: 973–977, Sep. 1992.

Schoepp, D., Bockaert, J., & Sladeczek, F. (1990) Pharmacological and functional characteristics of metabotropic excitatory amino acid receptors, Trend Pharm. Sci. 11:508–515.

Sugiyama, H., Ito, I, and Hirona, C. (1987) A new type of glutamate receptor linked to inositol phospholipid metabolism, Nature 325:531–533.

Oikawa, S., Inuzuka, C., Kuroki, M., Matsuoka, Y., Kosaki, G., & Nakazato, H. (1989) Cell Adhesion Activity of non-–specific cross–reacting antigen (NCA) and carcinoembryonic antigen (CEA) expressed on CHO cells surface, Biochem. Biophys. Res. Comm. 164(1):39–45.

Nakajima et al., Molecular characterization of a novel retinal metabotropic glutamate receptor mGluR6 with a high agonist selectivity for L–2–amino–4 phosphonobutyrate, J. Biol. Chem., 268(16): 11868–11873, Jun. 5, 1993.

Pittler et al., Primary structure and chromosomal localization of human and mouse rod photoreceptor cGMP–gated cation channel, J. Biol. Chem., 267(9): 6257–6262, Mar. 25, 1992.

Nawy et al., Suppression by glutamate of cGMP–activated conductance in retinal bipolar cells, Nature, 346:269–271, Jul. 19, 1990.

Takahashi et al., Role of the large extracellular domain of metabotropic glutamate receptors in agonist selectiveity determination, J. Biol. Chem., 268(26): 19341–19345, Sep. 15, 1993.

Watson et al., The G–protein Linked Receptor FactsBook, Academic Press:London, pp. 131, 134, 214, 163, 1994.

Huang et al., Functional expression of rat M5 muscarinic acetylcholine receptor in yeast, Biochem. Biophys. Res. Comm., 182(3): 1180–1186, Feb. 14, 1992.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 3321 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 388..3108
      (D) OTHER INFORMATION: /product= "HUMAN MGLUR1B"

(xi) SEQUENCE DESCRIPTION: SEQ ID NO:1:

```
GCCGAGCGTG GCCACGGYCC TCTGGCCCCG GGACCATAGC GCTGTCTACC CCGACTCAGG      60

TACTCAGCAT CTAGCTCACC GCTGCCAACA CGACTTCCAC TGTACTCTTG ATCAATTTAC     120

CTTGATGCAC TACCGGTGAA GAACGGGGAC TCGAATTCCC TTACAAACGC CTCCAGCTTG     180

TAGAGGCGGT CGTGGAGGAC CCAGAGGAGG AGACGAAGGG GAAGGAGGCG GTGGTGGAGG     240

AGGCAAAGGC CTTGGACGAC CATTGTTGGC GAGGGCACC ACTCCGGGAG AGGCGGCGCT     300

GGGCGTCTTG GGGGTGCGCG CCGGGAGCCT GCAGCGGGAC CAGCGTGGGA ACGCGGCTGG     360

CAGGCTGTGG ACCTCGTCCT CACCACC ATG GTC GGG CTC CTT TTG TTT TTT          411
                                Met Val Gly Leu Leu Leu Phe Phe
                                 1               5

TTC CCA GCG ATC TTT TTG GAG GTG TCC CTT CTC CCC AGA AGC CCC GGC        459
Phe Pro Ala Ile Phe Leu Glu Val Ser Leu Leu Pro Arg Ser Pro Gly
         10                  15                  20

AGG AAA GTG TTG CTG GCA GGA GCG TCG TCT CAG CGC TCG GTG GCC AGA        507
Arg Lys Val Leu Leu Ala Gly Ala Ser Ser Gln Arg Ser Val Ala Arg
 25                  30                  35                  40

ATG GAC GGA GAT GTC ATC ATT GGA GCC CTC TTC TCA GTC CAT CAC CAG        555
Met Asp Gly Asp Val Ile Ile Gly Ala Leu Phe Ser Val His His Gln
                 45                  50                  55

CCT CCG GCC GAG AAA GTG CCC GAG AGG AAG TGT GGG GAG ATC AGG GAG        603
Pro Pro Ala Glu Lys Val Pro Glu Arg Lys Cys Gly Glu Ile Arg Glu
             60                  65                  70

CAG TAT GGC ATC CAG AGG GTG GAG GCC ATG TTC CAC ACG TTG GAT AAG        651
Gln Tyr Gly Ile Gln Arg Val Glu Ala Met Phe His Thr Leu Asp Lys
         75                  80                  85

ATC AAC GCG GAC CCG GTC CTC CTG CCC AAC ATC ACC CTG GGC AGT GAG        699
Ile Asn Ala Asp Pro Val Leu Leu Pro Asn Ile Thr Leu Gly Ser Glu
 90                  95                 100

ATC CGG GAC TCC TGC TGG CAC TCT TCC GTG GCT CTG GAA CAG AGC ATT        747
Ile Arg Asp Ser Cys Trp His Ser Ser Val Ala Leu Glu Gln Ser Ile
105                 110                 115                 120

GAG TTC ATT AGG GAC TCT CTG ATT TCC ATT CGA GAT GAG AAG GAT GGG        795
Glu Phe Ile Arg Asp Ser Leu Ile Ser Ile Arg Asp Glu Lys Asp Gly
                125                 130                 135

ATC AAC CGG TGT CTG CCT GAC GGC CAG TCC CTC CCC CCA GGC AGG ACT        843
Ile Asn Arg Cys Leu Pro Asp Gly Gln Ser Leu Pro Pro Gly Arg Thr
            140                 145                 150

AAG AAG CCC ATT GCG GGA GTG ATC GGT CCC GGC TCC AGC TCT GTA GCC        891
Lys Lys Pro Ile Ala Gly Val Ile Gly Pro Gly Ser Ser Ser Val Ala
        155                 160                 165
```

```
ATT CAA GTG CAG AAC CTG CTC CAG CTC TTC GAC ATC CCC CAG ATC GCT    939
Ile Gln Val Gln Asn Leu Leu Gln Leu Phe Asp Ile Pro Gln Ile Ala
170                 175                 180

TAT TCA GCC ACA AGC ATC GAC CTG AGT GAC AAA ACT TTG TAC AAA TAC    987
Tyr Ser Ala Thr Ser Ile Asp Leu Ser Asp Lys Thr Leu Tyr Lys Tyr
185                 190                 195                 200

TTC CTG AGG GTT GTC CCT TCT GAC ACT TTG CAG GCA AGG GCC ATG CTT   1035
Phe Leu Arg Val Val Pro Ser Asp Thr Leu Gln Ala Arg Ala Met Leu
                205                 210                 215

GAC ATA GTC AAA CGT TAC AAT TGG ACC TAT GTC TCT GCA GTC CAC ACG   1083
Asp Ile Val Lys Arg Tyr Asn Trp Thr Tyr Val Ser Ala Val His Thr
            220                 225                 230

GAA GGG AAT TAT GGG GAG AGC GGA ATG GAC GCT TTC AAA GAG CTG GCT   1131
Glu Gly Asn Tyr Gly Glu Ser Gly Met Asp Ala Phe Lys Glu Leu Ala
        235                 240                 245

GCC CAG GAA GGC CTC TGT ATC GCC CAT TCT GAC AAA ATC TAC AGC AAC   1179
Ala Gln Glu Gly Leu Cys Ile Ala His Ser Asp Lys Ile Tyr Ser Asn
    250                 255                 260

GCT GGG GAG AAG AGC TTT GAC CGA CTC TTG CGC AAA CTC CGA GAG AGG   1227
Ala Gly Glu Lys Ser Phe Asp Arg Leu Leu Arg Lys Leu Arg Glu Arg
265                 270                 275                 280

CTT CCC AAG GCT AGA GTG GTG GTC TGC TTC TGT GAA GGC ATG ACA GTG   1275
Leu Pro Lys Ala Arg Val Val Val Cys Phe Cys Glu Gly Met Thr Val
                285                 290                 295

CGA GGA CTC CTG AGC GCC ATG CGG CGC CTT GGC GTC GTG GGC GAG TTC   1323
Arg Gly Leu Leu Ser Ala Met Arg Arg Leu Gly Val Val Gly Glu Phe
            300                 305                 310

TCA CTC ATT GGA AGT GAT GGA TGG GCA GAC AGA GAT GAA GTC ATT GAA   1371
Ser Leu Ile Gly Ser Asp Gly Trp Ala Asp Arg Asp Glu Val Ile Glu
        315                 320                 325

GGT TAT GAG GTG GAA GCC AAC GGG GGA ATC ACG ATA AAG CTG CAG TCT   1419
Gly Tyr Glu Val Glu Ala Asn Gly Gly Ile Thr Ile Lys Leu Gln Ser
    330                 335                 340

CCA GAG GTC AGG TCA TTT GAT GAT TAT TTC CTG AAA CTG AGG CTG GAC   1467
Pro Glu Val Arg Ser Phe Asp Asp Tyr Phe Leu Lys Leu Arg Leu Asp
345                 350                 355                 360

ACT AAC ACG AGG AAT CCC TGG TTC CCT GAG TTC TGG CAA CAT CGG TTC   1515
Thr Asn Thr Arg Asn Pro Trp Phe Pro Glu Phe Trp Gln His Arg Phe
                365                 370                 375

CAG TGC CGC CTT CCA GGA CAC CTT CTG GAA AAT CCC AAC TTT AAA CGA   1563
Gln Cys Arg Leu Pro Gly His Leu Leu Glu Asn Pro Asn Phe Lys Arg
            380                 385                 390

ATC TGC ACA GGC AAT GAA AGC TTA GAA GAA AAC TAT GTC CAG GAC AGT   1611
Ile Cys Thr Gly Asn Glu Ser Leu Glu Glu Asn Tyr Val Gln Asp Ser
        395                 400                 405

AAG ATG GGG TTT GTC ATC AAT GCC ATC TAT GCC ATG GCA CAT GGG CTG   1659
Lys Met Gly Phe Val Ile Asn Ala Ile Tyr Ala Met Ala His Gly Leu
    410                 415                 420

CAG AAC ATG CAC CAT GCC CTC TGC CCT GGC CAC GTG GGC CTC TGC GAT   1707
Gln Asn Met His His Ala Leu Cys Pro Gly His Val Gly Leu Cys Asp
425                 430                 435                 440

GCC ATG AAG CCC ATC GAC GGC AGC AAG CTG CTG GAC TTC CTC ATC AAG   1755
Ala Met Lys Pro Ile Asp Gly Ser Lys Leu Leu Asp Phe Leu Ile Lys
                445                 450                 455

TCC TCA TTC ATT GGA GTA TCT GGA GAG GAG GTG TGG TTT GAT GAG AAA   1803
Ser Ser Phe Ile Gly Val Ser Gly Glu Glu Val Trp Phe Asp Glu Lys
            460                 465                 470

GGA GAC GCT CCT GGA AGG TAT GAT ATC ATG AAT CTG CAG TAC ACT GAA   1851
Gly Asp Ala Pro Gly Arg Tyr Asp Ile Met Asn Leu Gln Tyr Thr Glu
        475                 480                 485
```

-continued

| | | |
|---|---|---|
| GCT AAT CGC TAT GAC TAT GTG CAC GTT GGA ACC TGG CAT GAA GGA GTG<br>Ala Asn Arg Tyr Asp Tyr Val His Val Gly Thr Trp His Glu Gly Val<br>490                          495                     500 | | 1899 |
| CTG AAC ATT GAT GAT TAC AAA ATC CAG ATG AAC AAG AGT GGA GTG GTG<br>Leu Asn Ile Asp Asp Tyr Lys Ile Gln Met Asn Lys Ser Gly Val Val<br>505                    510                  515                  520 | | 1947 |
| CGG TCT GTG TGC AGT GAG CCT TGC TTA AAG GGC CAG ATT AAG GTT ATA<br>Arg Ser Val Cys Ser Glu Pro Cys Leu Lys Gly Gln Ile Lys Val Ile<br>             525                  530                  535 | | 1995 |
| CGG AAA GGA GAA GTG AGC TGC TGC TGG ATT TGC GCG GCC TGC AAA GAG<br>Arg Lys Gly Glu Val Ser Cys Cys Trp Ile Cys Ala Ala Cys Lys Glu<br>        540                  545                  550 | | 2043 |
| AAT GAA TAT GTG CAA GAT GAG TTC ACC TGC AAA GCT TGT GAC TTG GGA<br>Asn Glu Tyr Val Gln Asp Glu Phe Thr Cys Lys Ala Cys Asp Leu Gly<br>        555                  560                  565 | | 2091 |
| TGG TGG CCC AAT GCA GAT CTA ACA GGC TGT GAG CCC ATT CCT GTG CGC<br>Trp Trp Pro Asn Ala Asp Leu Thr Gly Cys Glu Pro Ile Pro Val Arg<br>        570                  575                  580 | | 2139 |
| TAT CTT GAG TGG AGC AAC ATC GAA TCC ATT ATA GCC ATC GCC TTT TCA<br>Tyr Leu Glu Trp Ser Asn Ile Glu Ser Ile Ile Ala Ile Ala Phe Ser<br>585                          590                  595                  600 | | 2187 |
| TGC CTG GGA ATC CTT GTT ACC TTG TTT GTC ACC CTA ATC TTT GTA CTG<br>Cys Leu Gly Ile Leu Val Thr Leu Phe Val Thr Leu Ile Phe Val Leu<br>                     605                  610                  615 | | 2235 |
| TAC CGG GAC ACA CCA GTG GTC AAA TCC TCC AGT CGG GAG CTC TGC TAC<br>Tyr Arg Asp Thr Pro Val Val Lys Ser Ser Ser Arg Glu Leu Cys Tyr<br>        620                  625                  630 | | 2283 |
| ATC ATC CTA GCT GGC ATC TTC CTT GGT TAT GTG TGC CCA TTC ACT CTC<br>Ile Ile Leu Ala Gly Ile Phe Leu Gly Tyr Val Cys Pro Phe Thr Leu<br>             635                  640                  645 | | 2331 |
| ATT GCC AAA CCT ACT ACC ACC TCC TGC TAC CTC CAG CGC CTC TTG GTT<br>Ile Ala Lys Pro Thr Thr Thr Ser Cys Tyr Leu Gln Arg Leu Leu Val<br>650                          655                  660 | | 2379 |
| GGC CTC TCC TCT GCG ATG TGC TAC TCT GCT TTA GTG ACT AAA ACC AAT<br>Gly Leu Ser Ser Ala Met Cys Tyr Ser Ala Leu Val Thr Lys Thr Asn<br>665                          670                  675                  680 | | 2427 |
| CGT ATT GCA CGC ATC CTG GCT GGC AGC AAG AAG AAG ATC TGC ACC CGG<br>Arg Ile Ala Arg Ile Leu Ala Gly Ser Lys Lys Lys Ile Cys Thr Arg<br>             685                  690                  695 | | 2475 |
| AAG CCC AGG TTC ATG AGT GCC TGG GCT CAG GTG ATC ATT GCC TCA ATT<br>Lys Pro Arg Phe Met Ser Ala Trp Ala Gln Val Ile Ile Ala Ser Ile<br>                  700                  705                  710 | | 2523 |
| CTG ATT AGT GTG CAA CTA ACC CTG GTG GTA ACC CTG ATC ATC ATG GAA<br>Leu Ile Ser Val Gln Leu Thr Leu Val Val Thr Leu Ile Ile Met Glu<br>        715                  720                  725 | | 2571 |
| CCC CCT ATG CCC ATT CTG TCC TAC CCA AGT ATC AAG GAA GTC TAC CTT<br>Pro Pro Met Pro Ile Leu Ser Tyr Pro Ser Ile Lys Glu Val Tyr Leu<br>730                          735                  740 | | 2619 |
| ATC TGC AAT ACC AGC AAC CTG GGT GTG GTG GCC CCT TTG GGC TAC AAT<br>Ile Cys Asn Thr Ser Asn Leu Gly Val Val Ala Pro Leu Gly Tyr Asn<br>745                          750                  755                  760 | | 2667 |
| GGA CTC CTC ATC ATG AGC TGT ACC TAC TAT GCC TTC AAG ACC CGC AAC<br>Gly Leu Leu Ile Met Ser Cys Thr Tyr Tyr Ala Phe Lys Thr Arg Asn<br>             765                  770                  775 | | 2715 |
| GTG CCC GCC AAC TTC AAC GAG GCC AAA TAT ATC GCG TTC ACC ATG TAC<br>Val Pro Ala Asn Phe Asn Glu Ala Lys Tyr Ile Ala Phe Thr Met Tyr<br>        780                  785                  790 | | 2763 |
| ACC ACC TGT ATC ATC TGG CTA GCT TTT GTG CCC ATT TAC TTT GGG AGC<br>Thr Thr Cys Ile Ile Trp Leu Ala Phe Val Pro Ile Tyr Phe Gly Ser<br>        795                  800                  805 | | 2811 |

-continued

```
AAC TAC AAG ATC ATC ACA ACT TGC TTT GCA GTG AGT CTC AGT GTA ACA     2859
Asn Tyr Lys Ile Ile Thr Thr Cys Phe Ala Val Ser Leu Ser Val Thr
810                 815                 820

GTG GCT CTG GGG TGC ATG TTC ACT CCC AAG ATG TAC ATC ATT ATT GCC     2907
Val Ala Leu Gly Cys Met Phe Thr Pro Lys Met Tyr Ile Ile Ile Ala
825                 830                 835                 840

AAG CCT GAG AGG AAT GTC CGC AGT GCC TTC ACC ACC TCT GAT GTT GTC     2955
Lys Pro Glu Arg Asn Val Arg Ser Ala Phe Thr Thr Ser Asp Val Val
                845                 850                 855

CGC ATG CAT GTT GGC GAT GGC AAG CTG CCC TGC CGC TCC AAC ACT TTC     3003
Arg Met His Val Gly Asp Gly Lys Leu Pro Cys Arg Ser Asn Thr Phe
                860                 865                 870

CTC AAC ATC TTC CGA AGA AAG AAG GCA GGG GCA GGG AAT GCC AAG AAG     3051
Leu Asn Ile Phe Arg Arg Lys Lys Ala Gly Ala Gly Asn Ala Lys Lys
                875                 880                 885

AGG CAG CCA GAA TTC TCG CCC ACC AGC CAA TGT CCG TCG GCA CAT GTG     3099
Arg Gln Pro Glu Phe Ser Pro Thr Ser Gln Cys Pro Ser Ala His Val
890                 895                 900

CAG CTT TGAAAACCCC CACACTGCAG TGAATGTTTC TAATGGCAAG TCTGTGTCAT      3155
Gln Leu
905

GGTCTGAACC AGGTGGAGGA CAGGTGCCCA AGGGACAGCA TATGTGGCAC CGCCTCTCTG   3215

TGCACGTGAA GACCAATGAG ACGGCCTGCA ACCAAACAGC CGTCATCAAA CCCCTCACTA   3275

AAAGTTACCA AGGCTCTGGC AAGAGCCTGA CCTTTTCAGA TACCAG                  3321

(2) INFORMATION FOR SEQ ID NO:2:

(i) SEQUENCE CHARACTERISTICS:
        (A) LENGTH: 906 amino acids
        (B) TYPE: amino acid
        (D) TOPOLOGY: linear (ii) MOLECULE TYPE: protein (xi) SEQUENCE DESCRIPTION: SEQ ID NO:2:

Met Val Gly Leu Leu Phe Phe Phe Pro Ala Ile Phe Leu Glu Val
1               5                   10                  15

Ser Leu Leu Pro Arg Ser Pro Gly Arg Lys Val Leu Leu Ala Gly Ala
            20                  25                  30

Ser Ser Gln Arg Ser Val Ala Arg Met Asp Gly Asp Val Ile Ile Gly
        35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
        115                 120                 125

Ser Ile Arg Asp Glu Lys Asp Gly Ile Asn Arg Cys Leu Pro Asp Gly
    130                 135                 140

Gln Ser Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175
```

-continued

```
Leu Phe Asp Ile Pro Gln Ile Ala Tyr Ser Ala Thr Ser Ile Asp Leu
                180                 185                 190

Ser Asp Lys Thr Leu Tyr Lys Tyr Phe Leu Arg Val Pro Ser Asp
        195                 200                 205

Thr Leu Gln Ala Arg Ala Met Leu Asp Ile Val Lys Arg Tyr Asn Trp
    210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
    290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
    370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
        435                 440                 445

Lys Leu Leu Asp Phe Leu Ile Lys Ser Ser Phe Ile Gly Val Ser Gly
    450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
        515                 520                 525

Leu Lys Gly Gln Ile Lys Val Ile Arg Lys Gly Glu Val Ser Cys Cys
    530                 535                 540

Trp Ile Cys Ala Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
                565                 570                 575

Gly Cys Glu Pro Ile Pro Val Arg Tyr Leu Glu Trp Ser Asn Ile Glu
            580                 585                 590

Ser Ile Ile Ala Ile Ala Phe Ser Cys Leu Gly Ile Leu Val Thr Leu
        595                 600                 605
```

```
Phe Val Thr Leu Ile Phe Val Leu Tyr Arg Asp Thr Pro Val Val Lys
        610             615             620
Ser Ser Ser Arg Glu Leu Cys Tyr Ile Ile Leu Ala Gly Ile Phe Leu
625             630             635             640
Gly Tyr Val Cys Pro Phe Thr Leu Ile Ala Lys Pro Thr Thr Thr Ser
            645             650             655
Cys Tyr Leu Gln Arg Leu Leu Val Gly Leu Ser Ser Ala Met Cys Tyr
        660             665             670
Ser Ala Leu Val Thr Lys Thr Asn Arg Ile Ala Arg Ile Leu Ala Gly
    675             680             685
Ser Lys Lys Lys Ile Cys Thr Arg Lys Pro Arg Phe Met Ser Ala Trp
690             695             700
Ala Gln Val Ile Ile Ala Ser Ile Leu Ile Ser Val Gln Leu Thr Leu
705             710             715             720
Val Val Thr Leu Ile Ile Met Glu Pro Pro Met Pro Ile Leu Ser Tyr
            725             730             735
Pro Ser Ile Lys Glu Val Tyr Leu Ile Cys Asn Thr Ser Asn Leu Gly
        740             745             750
Val Val Ala Pro Leu Gly Tyr Asn Gly Leu Leu Ile Met Ser Cys Thr
    755             760             765
Tyr Tyr Ala Phe Lys Thr Arg Asn Val Pro Ala Asn Phe Asn Glu Ala
770             775             780
Lys Tyr Ile Ala Phe Thr Met Tyr Thr Thr Cys Ile Ile Trp Leu Ala
785             790             795             800
Phe Val Pro Ile Tyr Phe Gly Ser Asn Tyr Lys Ile Ile Thr Thr Cys
            805             810             815
Phe Ala Val Ser Leu Ser Val Thr Val Ala Leu Gly Cys Met Phe Thr
        820             825             830
Pro Lys Met Tyr Ile Ile Ile Ala Lys Pro Glu Arg Asn Val Arg Ser
    835             840             845
Ala Phe Thr Thr Ser Asp Val Val Arg Met His Val Gly Asp Gly Lys
850             855             860
Leu Pro Cys Arg Ser Asn Thr Phe Leu Asn Ile Phe Arg Arg Lys Lys
865             870             875             880
Ala Gly Ala Gly Asn Ala Lys Lys Arg Gln Pro Glu Phe Ser Pro Thr
            885             890             895
Ser Gln Cys Pro Ser Ala His Val Gln Leu
        900             905

(2) INFORMATION FOR SEQ ID NO:3:

(i) SEQUENCE CHARACTERISTICS:
        (A) LENGTH: 355 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..354
        (D) OTHER INFORMATION: /product= "HUMAN MGLUR2 FRAGMENT"

(xi) SEQUENCE DESCRIPTION: SEQ ID NO:3:

GCC AAG CCA TCC ACG GCA GTG TGT ACC TTA CGG CGT CTT GGT TTG GGC      48
Ala Lys Pro Ser Thr Ala Val Cys Thr Leu Arg Arg Leu Gly Leu Gly
 1               5                  10                  15
```

```
ACT GCC TTC TCT GTC TGC TAC TCA GCC CTG CTC ACC AAG ACC AAC CGC        96
Thr Ala Phe Ser Val Cys Tyr Ser Ala Leu Leu Thr Lys Thr Asn Arg
            20                  25                  30

ATT GCA CGC ATC TTC GGT GGG GCC CGG GAG GGT GCC CAG CGG CCA CGC       144
Ile Ala Arg Ile Phe Gly Gly Ala Arg Glu Gly Ala Gln Arg Pro Arg
 35                  40                  45

TTC ATC AGT CCT GCC TCA CAG GTG GCC ATC TGC CTG GAA CTT ATC TCG       192
Phe Ile Ser Pro Ala Ser Gln Val Ala Ile Cys Leu Glu Leu Ile Ser
    50                  55                  60

GGC CAG CTG CTC ATC GTG GTC GCC TGG CTG GTG GTG GAG GCA CCG GGC       240
Gly Gln Leu Leu Ile Val Val Ala Trp Leu Val Val Glu Ala Pro Gly
 65                  70                  75                  80

ACA GGC AAG GAG ACA GCC CCC GAA CGG CGG GAG GTG GTG ACA CTG CGC       288
Thr Gly Lys Glu Thr Ala Pro Glu Arg Arg Glu Val Val Thr Leu Arg
                 85                  90                  95

TGC AAC CAC CGC GAT GCA AGT ATG TTG GGC TCG CTG GCC TAC AAT GTG       336
Cys Asn His Arg Asp Ala Ser Met Leu Gly Ser Leu Ala Tyr Asn Val
                100                 105                 110

CTC CTC ATC GCG CTC TGC A                                             355
Leu Leu Ile Ala Leu Cys
            115

(2) INFORMATION FOR SEQ ID NO:4:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:4:

Ala Lys Pro Ser Thr Ala Val Cys Thr Leu Arg Arg Leu Gly Leu Gly
 1               5                  10                  15

Thr Ala Phe Ser Val Cys Tyr Ser Ala Leu Leu Thr Lys Thr Asn Arg
            20                  25                  30

Ile Ala Arg Ile Phe Gly Gly Ala Arg Glu Gly Ala Gln Arg Pro Arg
 35                  40                  45

Phe Ile Ser Pro Ala Ser Gln Val Ala Ile Cys Leu Glu Leu Ile Ser
    50                  55                  60

Gly Gln Leu Leu Ile Val Val Ala Trp Leu Val Val Glu Ala Pro Gly
 65                  70                  75                  80

Thr Gly Lys Glu Thr Ala Pro Glu Arg Arg Glu Val Val Thr Leu Arg
                 85                  90                  95

Cys Asn His Arg Asp Ala Ser Met Leu Gly Ser Leu Ala Tyr Asn Val
                100                 105                 110

Leu Leu Ile Ala Leu Cys
            115

(2) INFORMATION FOR SEQ ID NO:5:

(i) SEQUENCE CHARACTERISTICS:
        (A) LENGTH: 3919 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1064..3703
        (D) OTHER INFORMATION: /product= "HUMAN MGLUR3"
```

(xi) SEQUENCE DESCRIPTION: SEQ ID NO:5:

```
CGGCCTCCCT GGCTCTCACA CTCCCTCTCT GCTCCCGCTC TCCTAATCTC CTCTGGCATG      60

CGGTCAGCCC CCTGCCCAGG GACCACAGGA GAGTTCTTGT AAGGACTGTT AGTCCCTGCT     120

TACCTGAAAG CCAAGCGCTC TAGCAGAGCT TTAAAGTTGG AGCCGCCACC CTCCCTACCG     180

CCCCATGCCC CTTCACCCCA CTCCGAAATT CACCGACCTT TGCATGCACT GCCTAAGGAT     240

TTCAGAGTGA GGCAAAGCAG TCGGCAAATC TACCCTGGCT TTTCGTATAA AAATCCTCTC     300

GTCTAGGTAC CCTGGCTCAC TGAAGACTCT GCAGATATAC CCTTATAAGA GGGAGGGTGG     360

GGGAGGGAAA AGAACGAGAG AGGGAGGAAA GAATGAAAAG GAGAGGATGC CAGGAGGTCC     420

GTGCTTCTGC CAAGAGTCCC AATTAGATGC GACGGCTTCA GCCTGGTCAA GGTGAAGGAA     480

AGTTGCTTCC GCGCCTAGGA AGTGGGTTTG CCTGATAAGA GAAGGAGGAG GGGACTCGGC     540

TGGGAAGAGC TCCCCTCCCC TCCGCGGAAG ACCACTGGGT CCCCTCTTTC GGCAACCTCC     600

TCCCTCTCTT CTACTCCACC CCTCCGTTTT CCCACTCCCC ACTGACTCGG ATGCCTGGAT     660

GTTCTGCCAC CGGGCAGTGG TCCAGCGTGC AGCGGGAGG GGGCAGGGGC AGGGGGCACT     720

GTGACAGGAA GCTGCGCGCA CAAGTTGGCC ATTTCGAGGG CAAAATAAGT TCTCCCTTGG     780

ATTTGGAAAG GACAAAGCCA GTAAGCTACC TCTTTTGTGT CGGATGAGGA GGACCAACCA     840

TGAGCCAGAG CCCGGGTGCA GGCTCACCGC CGCCGCTGCC ACCGCGGTCA GCTCCAGTTC     900

CTGCCAGGAG TTGTCGGTGC GAGGAATTTT GTGACAGGCT CTGTTAGTCT GTTCCTCCCT     960

TATTTGAAGG ACAGGCCAAA GATCCAGTTT GGAAATGAGA GAGGACTAGC ATGACACATT    1020

GGCTCCACCA TTGATATCTC CCAGAGGTAC AGAAACAGGA TTC ATG AAG ATG TTG      1075
                                              Met Lys Met Leu
                                                1
```

| ACA AGA CTG CAA GTT CTT ACC TTA GCT TTG TTT TCA AAG GGA TTT TTA | 1123 |
| Thr Arg Leu Gln Val Leu Thr Leu Ala Leu Phe Ser Lys Gly Phe Leu | |
| 5                  10                 15                 20 | |

```
CTC TCT TTA GGG GAC CAT AAC TTT CTA AGG AGA GAG ATT AAA ATA GAA    1171
Leu Ser Leu Gly Asp His Asn Phe Leu Arg Arg Glu Ile Lys Ile Glu
            25                  30                  35

GGT GAC CTT GTT TTA GGG GGC CTG TTT CCT ATT AAC GAA AAA GGC ACT    1219
Gly Asp Leu Val Leu Gly Gly Leu Phe Pro Ile Asn Glu Lys Gly Thr
        40                  45                  50

GGA ACT GAA GAA TGT GGG CGA ATC AAT GAA GAC CGA GGG ATT CAA CGC    1267
Gly Thr Glu Glu Cys Gly Arg Ile Asn Glu Asp Arg Gly Ile Gln Arg
    55                  60                  65

CTG GAA GCC ATG TTG TTT GCT ATT GAT GAA ATC AAC AAA GAT GAT TAC    1315
Leu Glu Ala Met Leu Phe Ala Ile Asp Glu Ile Asn Lys Asp Asp Tyr
70                  75                  80

TTG CTA CCA GGA GTG AAG TTG GGT GTT CAC ATT TTG GAT ACA TGT TCA    1363
Leu Leu Pro Gly Val Lys Leu Gly Val His Ile Leu Asp Thr Cys Ser
85                  90                  95                 100

AGG GAT ACC TAT GCA TTG GAG CAA TCA CTG GAG TTT GTC AGG GCA TCT    1411
Arg Asp Thr Tyr Ala Leu Glu Gln Ser Leu Glu Phe Val Arg Ala Ser
            105                 110                 115

TTG ACA AAA GTG GAT GAA GCT GAG TAT ATG TGT CCT GAT GGA TCC TAT    1459
Leu Thr Lys Val Asp Glu Ala Glu Tyr Met Cys Pro Asp Gly Ser Tyr
        120                 125                 130

GCC ATT CAA GAA AAC ATC CCA CTT CTC ATT GCA GGG GTC ATT GGT GGC    1507
Ala Ile Gln Glu Asn Ile Pro Leu Leu Ile Ala Gly Val Ile Gly Gly
    135                 140                 145

TCT TAT AGC AGT GTT TCC ATA CAG GTG GCA AAC CTG CTG CGG CTC TTC    1555
Ser Tyr Ser Ser Val Ser Ile Gln Val Ala Asn Leu Leu Arg Leu Phe
150                 155                 160
```

-continued

| | | |
|---|---|---|
| CAG ATC CCT CAG ATC AGC TAC GCA TCC ACC AGC GCC AAA CTC AGT GAT<br>Gln Ile Pro Gln Ile Ser Tyr Ala Ser Thr Ser Ala Lys Leu Ser Asp<br>165                    170                    175                    180 | 1603 |
| AAG TCG CGC TAT GAT TAC TTT GCC AGG ACC GTG CCC CCC GAC TTC TAC<br>Lys Ser Arg Tyr Asp Tyr Phe Ala Arg Thr Val Pro Pro Asp Phe Tyr<br>                    185                    190                    195 | 1651 |
| CAG GCC AAA GCC ATG GCT GAG ATC TTG CGC TTC TTC AAC TGG ACC TAC<br>Gln Ala Lys Ala Met Ala Glu Ile Leu Arg Phe Phe Asn Trp Thr Tyr<br>                    200                    205                    210 | 1699 |
| GTG TCC ACA GTA GCC TCC GAG GGT GAT TAC GGG GAG ACA GGG ATC GAG<br>Val Ser Thr Val Ala Ser Glu Gly Asp Tyr Gly Glu Thr Gly Ile Glu<br>      215                    220                    225 | 1747 |
| GCC TTC GAG CAG GAA GCC CGC CTG CGC AAC ATC TGC ATC GCT ACG GCG<br>Ala Phe Glu Gln Glu Ala Arg Leu Arg Asn Ile Cys Ile Ala Thr Ala<br>230                    235                    240 | 1795 |
| GAG AAG GTG GGC CGC TCC AAC ATC CGC AAG TCC TAC GAC AGC GTG ATC<br>Glu Lys Val Gly Arg Ser Asn Ile Arg Lys Ser Tyr Asp Ser Val Ile<br>245                    250                    255                    260 | 1843 |
| CGA GAA CTG TTG CAG AAG CCC AAC GCG CGC GTC GTG GTC CTC TTC ATG<br>Arg Glu Leu Leu Gln Lys Pro Asn Ala Arg Val Val Val Leu Phe Met<br>                    265                    270                    275 | 1891 |
| CGC AGC GAC GAC TCG CGG GAG CTC ATT GCA GCC GCC AGC CGC GCC AAT<br>Arg Ser Asp Asp Ser Arg Glu Leu Ile Ala Ala Ala Ser Arg Ala Asn<br>                    280                    285                    290 | 1939 |
| GCC TCC TTC ACC TGG GTG GCC AGC GAC GGT TGG GGC GCG CAG GAG AGC<br>Ala Ser Phe Thr Trp Val Ala Ser Asp Gly Trp Gly Ala Gln Glu Ser<br>      295                    300                    305 | 1987 |
| ATC ATC AAG GGC AGC GAG CAT GTG GCC TAC GGC GAC ATC ACC CTG GAG<br>Ile Ile Lys Gly Ser Glu His Val Ala Tyr Gly Asp Ile Thr Leu Glu<br>310                    315                    320 | 2035 |
| CTG GCC TCC CAG CCT GTC CGC CAG TTC GGC CGC TAC TTC CAG AGC CTC<br>Leu Ala Ser Gln Pro Val Arg Gln Phe Gly Arg Tyr Phe Gln Ser Leu<br>325                    330                    335                    340 | 2083 |
| AAC CCC TAC AAC AAC CAC CGC AAC CCC TGG TTC CGG GAC TTC TGG GAG<br>Asn Pro Tyr Asn Asn His Arg Asn Pro Trp Phe Arg Asp Phe Trp Glu<br>                    345                    350                    355 | 2131 |
| CAA AAG TTT CAG TGC AGC CTC CAG AAC AAA CGC AAC CAC AGG CGC GTC<br>Gln Lys Phe Gln Cys Ser Leu Gln Asn Lys Arg Asn His Arg Arg Val<br>                    360                    365                    370 | 2179 |
| TGC GAA AAG CAC CTG GCC ATC GAC AGC AGC AAC TAC GAG CAA GAG TCC<br>Cys Glu Lys His Leu Ala Ile Asp Ser Ser Asn Tyr Glu Gln Glu Ser<br>      375                    380                    385 | 2227 |
| AAG ATC ATG TTT GTG GTG AAC GCG GTG TAT GCC ATG GCC CAC GCT TTG<br>Lys Ile Met Phe Val Val Asn Ala Val Tyr Ala Met Ala His Ala Leu<br>390                    395                    400 | 2275 |
| CAC AAA ATG CAG CGC ACC CTC TGT CCC AAC ACT ACC AAG CTT TGT GAT<br>His Lys Met Gln Arg Thr Leu Cys Pro Asn Thr Thr Lys Leu Cys Asp<br>405                    410                    415                    420 | 2323 |
| GCT ATG AAG ATC CTG GAT GGG AAG AAG TTG TAC AAG GAT TAC TTG CTG<br>Ala Met Lys Ile Leu Asp Gly Lys Lys Leu Tyr Lys Asp Tyr Leu Leu<br>                    425                    430                    435 | 2371 |
| AAA ATC AAC TTC ACG GCT CCA TTC AAC CCA AAT AAA GAT GCA GAT AGC<br>Lys Ile Asn Phe Thr Ala Pro Phe Asn Pro Asn Lys Asp Ala Asp Ser<br>                    440                    445                    450 | 2419 |
| ATA GTC AAG TTT GAC ACT TTT GGA GAT GGA ATG GGG CGA TAC AAC GTG<br>Ile Val Lys Phe Asp Thr Phe Gly Asp Gly Met Gly Arg Tyr Asn Val<br>      455                    460                    465 | 2467 |
| TTC AAT TTC CAA AAT GTA GGT GGG AAG TAT TCC TAC TTG AAA GTT GGT<br>Phe Asn Phe Gln Asn Val Gly Gly Lys Tyr Ser Tyr Leu Lys Val Gly<br>470                    475                    480 | 2515 |

-continued

| | |
|---|---|
| CAC TGG GCA GAA ACC TTA TCG CTA GAT GTC AAC TCT ATC CAC TGG TCC<br>His Trp Ala Glu Thr Leu Ser Leu Asp Val Asn Ser Ile His Trp Ser<br>485                   490                   495                   500 | 2563 |
| CGG AAC TCA GTC CCC ACT TCC CAG TGC AGC GAC CCC TGT GCC CCC AAT<br>Arg Asn Ser Val Pro Thr Ser Gln Cys Ser Asp Pro Cys Ala Pro Asn<br>                   505                   510                   515 | 2611 |
| GAA ATG AAG AAT ATG CAA CCA GGG GAT GTC TGC TGC TGG ATT TGC ATC<br>Glu Met Lys Asn Met Gln Pro Gly Asp Val Cys Cys Trp Ile Cys Ile<br>         520                   525                   530 | 2659 |
| CCC TGT GAA CCC TAC GAA TAC CTG GCT GAT GAG TTT ACC TGT ATG GAT<br>Pro Cys Glu Pro Tyr Glu Tyr Leu Ala Asp Glu Phe Thr Cys Met Asp<br>                   535                   540                   545 | 2707 |
| TGT GGG TCT GGA CAG TGG CCC ACT GCA GAC CTA ACT GGA TGC TAT GAC<br>Cys Gly Ser Gly Gln Trp Pro Thr Ala Asp Leu Thr Gly Cys Tyr Asp<br>         550                   555                   560 | 2755 |
| CTT CCT GAG GAC TAC ATC AGG TGG GAA GAC GCC TGG GCC ATT GGC CCA<br>Leu Pro Glu Asp Tyr Ile Arg Trp Glu Asp Ala Trp Ala Ile Gly Pro<br>565                   570                   575                   580 | 2803 |
| GTC ACC ATT GCC TGT CTG GGT TTT ATG TGT ACA TGC ATG GTT GTA ACT<br>Val Thr Ile Ala Cys Leu Gly Phe Met Cys Thr Cys Met Val Val Thr<br>                   585                   590                   595 | 2851 |
| GTT TTT ATC AAG CAC AAC AAC ACA CCC TTG GTC AAA GCA TCG GGC CGA<br>Val Phe Ile Lys His Asn Asn Thr Pro Leu Val Lys Ala Ser Gly Arg<br>         600                   605                   610 | 2899 |
| GAA CTC TGC TAC ATC TTA TTT TTT GGG GTT GGC CTG TCA TAC TGC ATG<br>Glu Leu Cys Tyr Ile Leu Leu Phe Gly Val Gly Leu Ser Tyr Cys Met<br>                   615                   620                   625 | 2947 |
| ACA TTC TTC TTC ATT GCC AAG CCA TCA CCA GTC ATC TGT GCA TTG CGC<br>Thr Phe Phe Phe Ile Ala Lys Pro Ser Pro Val Ile Cys Ala Leu Arg<br>         630                   635                   640 | 2995 |
| CGA CTC GGG CTG GGG AGT TCC TTC GCT ATC TGT TAC TCA GCC CTG CTG<br>Arg Leu Gly Leu Gly Ser Ser Phe Ala Ile Cys Tyr Ser Ala Leu Leu<br>645                   650                   655                   660 | 3043 |
| ACC AAG ACA AAC TGC ATT GCC CGC ATC TTC GAT GGG GTC AAG AAT GGC<br>Thr Lys Thr Asn Cys Ile Ala Arg Ile Phe Asp Gly Val Lys Asn Gly<br>                   665                   670                   675 | 3091 |
| GCT CAG AGG CCA AAA TTC ATC AGC CCC AGT TCT CAG GTT TTC ATC TGC<br>Ala Gln Arg Pro Lys Phe Ile Ser Pro Ser Ser Gln Val Phe Ile Cys<br>         680                   685                   690 | 3139 |
| CTG GGT CTG ATC CTG GTG CAA ATT GTG ATG GTG TCT GTG TGG CTC ATC<br>Leu Gly Leu Ile Leu Val Gln Ile Val Met Val Ser Val Trp Leu Ile<br>                   695                   700                   705 | 3187 |
| CTG GAG GCC CCA GGC ACC AGG AGG TAT ACC CTT GCA GAG AAG CGG GAA<br>Leu Glu Ala Pro Gly Thr Arg Arg Tyr Thr Leu Ala Glu Lys Arg Glu<br>         710                   715                   720 | 3235 |
| ACA GTC ATC CTA AAA TGC AAT GTC AAA GAT TCC AGC ATG TTG ATC TCT<br>Thr Val Ile Leu Lys Cys Asn Val Lys Asp Ser Ser Met Leu Ile Ser<br>725                   730                   735                   740 | 3283 |
| CTT ACC TAC GAT GTG ATC CTG GTG ATC TTA TGC ACT GTG TAC GCC TTC<br>Leu Thr Tyr Asp Val Ile Leu Val Ile Leu Cys Thr Val Tyr Ala Phe<br>                   745                   750                   755 | 3331 |
| AAA ACG CGG AAG TGC CCA GAA AAT TTC AAC GAA GCT AAG TTC ATA GGT<br>Lys Thr Arg Lys Cys Pro Glu Asn Phe Asn Glu Ala Lys Phe Ile Gly<br>         760                   765                   770 | 3379 |
| TTT ACC ATG TAC ACC ACG TGC ATC ATC TGG TTG GCC TTC CTC CCT ATA<br>Phe Thr Met Tyr Thr Thr Cys Ile Ile Trp Leu Ala Phe Leu Pro Ile<br>                   775                   780                   785 | 3427 |
| TTT TAT GTG ACA TCA AGT GAC TAC AGA GTG CAG ACG ACA ACC ATG TGC<br>Phe Tyr Val Thr Ser Ser Asp Tyr Arg Val Gln Thr Thr Thr Met Cys<br>         790                   795                   800 | 3475 |

```
ATC TCT GTC AGC CTG AGT GGC TTT GTG GTC TTG GGC TGT TTG TTT GCA    3523
Ile Ser Val Ser Leu Ser Gly Phe Val Val Leu Gly Cys Leu Phe Ala
805                 810                 815                 820

CCC AAG GTT CAC ATC ATC CTG TTT CAA CCC CAG AAG AAT GTT GTC ACA    3571
Pro Lys Val His Ile Ile Leu Phe Gln Pro Gln Lys Asn Val Val Thr
            825                 830                 835

CAC AGA CTG CAC CTC AAC AGG TTC AGT GTC AGT GGA ACT GGG ACC ACA    3619
His Arg Leu His Leu Asn Arg Phe Ser Val Ser Gly Thr Gly Thr Thr
                840                 845                 850

TAC TCT CAG TCC TCT GCA AGC ACG TAT GTG CCA ACG GTG TGC AAT GGG    3667
Tyr Ser Gln Ser Ser Ala Ser Thr Tyr Val Pro Thr Val Cys Asn Gly
        855                 860                 865

CGG GAA GTC CTC GAC TCC ACC ACC TCA TCT CTG TGATTGTGAA TTGCAGTTCA  3720
Arg Glu Val Leu Asp Ser Thr Thr Ser Ser Leu
870                 875                 880

GTTCTTGTGT TTTTAGACTG TTAGACAAAA GTGCTCACGT GCAGCTCCAG AAATATGGAAA 3780

CAGAGCAAAA GAACAACCCT AGTACCTTTT TTTAGAAACA GTACGATAAA TTATTTTTGA  3840

GGACTGTATA TAGTGATGTG CTAGAACTTT CTAGGCTGAG TCTAGTGCCC CTATTATTAA  3900

CAGTCCGAGT GTACGTACC                                               3919

(2) INFORMATION FOR SEQ ID NO:6:

(i) SEQUENCE CHARACTERISTICS:
        (A) LENGTH: 879 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Gly Arg Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
```

```
              210                 215                 220
Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
                260                 265                 270

Val Leu Phe Met Arg Ser Asp Ser Arg Glu Leu Ile Ala Ala Ala
            275                 280                 285

Ser Arg Ala Asn Ala Ser Phe Thr Trp Val Ala Ser Asp Gly Trp Gly
        290                 295                 300

Ala Gln Glu Ser Ile Ile Lys Gly Ser Glu His Val Ala Tyr Gly Asp
305                 310                 315                 320

Ile Thr Leu Glu Leu Ala Ser Gln Pro Val Arg Gln Phe Gly Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Arg Val Cys Glu Lys His Leu Ala Ile Asp Ser Ser Asn Tyr
        370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
            420                 425                 430

Asp Tyr Leu Leu Lys Ile Asn Phe Thr Ala Pro Phe Asn Pro Asn Lys
        435                 440                 445

Asp Ala Asp Ser Ile Val Lys Phe Asp Thr Phe Gly Asp Gly Met Gly
    450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
                485                 490                 495

Ile His Trp Ser Arg Asn Ser Val Pro Thr Ser Gln Cys Ser Asp Pro
            500                 505                 510

Cys Ala Pro Asn Glu Met Lys Asn Met Gln Pro Gly Asp Val Cys Cys
        515                 520                 525

Trp Ile Cys Ile Pro Cys Glu Pro Tyr Glu Tyr Leu Ala Asp Glu Phe
    530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
                565                 570                 575

Ala Ile Gly Pro Val Thr Ile Ala Cys Leu Gly Phe Met Cys Thr Cys
            580                 585                 590

Met Val Val Thr Val Phe Ile Lys His Asn Asn Thr Pro Leu Val Lys
        595                 600                 605

Ala Ser Gly Arg Glu Leu Cys Tyr Ile Leu Leu Phe Gly Val Gly Leu
    610                 615                 620

Ser Tyr Cys Met Thr Phe Phe Phe Ile Ala Lys Pro Ser Pro Val Ile
625                 630                 635                 640
```

```
Cys Ala Leu Arg Arg Leu Gly Leu Gly Ser Ser Phe Ala Ile Cys Tyr
            645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
                    725                 730                 735

Met Leu Ile Ser Leu Thr Tyr Asp Val Ile Leu Val Ile Leu Cys Thr
                    740                 745                 750

Val Tyr Ala Phe Lys Thr Arg Lys Cys Pro Glu Asn Phe Asn Glu Ala
                    755                 760                 765

Lys Phe Ile Gly Phe Thr Met Tyr Thr Thr Cys Ile Ile Trp Leu Ala
                    770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
                    805                 810                 815

Cys Leu Phe Ala Pro Lys Val His Ile Ile Leu Phe Gln Pro Gln Lys
                    820                 825                 830

Asn Val Val Thr His Arg Leu His Leu Asn Arg Phe Ser Val Ser Gly
                    835                 840                 845

Thr Gly Thr Thr Tyr Ser Gln Ser Ser Ala Ser Thr Tyr Val Pro Thr
        850                 855                 860

Val Cys Asn Gly Arg Glu Val Leu Asp Ser Thr Thr Ser Ser Leu
865                 870                 875
```

(2) INFORMATION FOR SEQ ID NO:7:

(i) SEQUENCE CHARACTERISTICS:
        (A) LENGTH: 4085 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 370..3912
        (D) OTHER INFORMATION: /product= "HUMAN MGLUR5A"

(xi) SEQUENCE DESCRIPTION: SEQ ID NO:7:

```
CAGCTCGGCT GTTCTGCGCA CGCTGAGCGG AGGGAATGAG CTTGAGATCA TCTTGGGGGG      60

GAAGCCGGGG ACTGGAGAGG CCGGCTCTGC CCTGCTGATC CCCGTGGCCC AACTTTTCGG     120

GGGGCTAGCT AGACCGAGTC TCACTGCTCG CAGCGCAGCC AACAGGGGGG TTTAGAAGAT     180

CATGACCACA TGGATCATCT AACTAAATGG TACATGGGGA CAAAATGGTC CTTTAGAAAA     240

TACATCTGAA TTGCTGGCTA ATTTCTTGAT TTGCGACTCA ACGTAGGACA TCGCTTGTTC     300

GTAGCTATCA GAACCCTCCT GAATTTTCCC CACCATGCTA TCTTTATTGG CTTGAACTCC     360

TTTCCTAAA ATG GTC CTT CTG TTG ATC CTG TCA GTC TTA CTT TGG AAA         408
            Met Val Leu Leu Leu Ile Leu Ser Val Leu Leu Trp Lys
              1               5                  10

GAA GAT GTC CGT GGG AGT GCA CAG TCC AGT GAG AGG AGG GTG GTG GCT        456
```

```
         Glu Asp Val Arg Gly Ser Ala Gln Ser Ser Glu Arg Arg Val Val Ala
             15                  20                  25

CAC ATG CCG GGT GAC ATC ATT ATT GGA GCT CTC TTT TCT GTT CAT CAC              504
His Met Pro Gly Asp Ile Ile Ile Gly Ala Leu Phe Ser Val His His
 30              35                  40                  45

CAG CCT ACT GTG GAC AAA GTT CAT GAG AGG AAG TGT GGG GCG GTC CGT              552
Gln Pro Thr Val Asp Lys Val His Glu Arg Lys Cys Gly Ala Val Arg
                 50                  55                  60

GAA CAG TAT GGC ATT CAG AGA GTG GAG GCC ATG CTG CAT ACC CTG GAA              600
Glu Gln Tyr Gly Ile Gln Arg Val Glu Ala Met Leu His Thr Leu Glu
             65                  70                  75

AGG ATC AAT TCA GAC CCC ACA CTC TTG CCC AAC ATC ACA CTG GGC TGT              648
Arg Ile Asn Ser Asp Pro Thr Leu Leu Pro Asn Ile Thr Leu Gly Cys
 80                  85                  90

GAG ATA AGG GAC TCC TGC TGG CAT TCG GCT GTG GCC CTA GAG CAG AGC              696
Glu Ile Arg Asp Ser Cys Trp His Ser Ala Val Ala Leu Glu Gln Ser
 95                 100                 105

ATT GAG TTC ATA AGA GAT TCC CTC ATT TCT TCA GAA GAG GAA GAA GGC              744
Ile Glu Phe Ile Arg Asp Ser Leu Ile Ser Ser Glu Glu Glu Glu Gly
110             115                 120                 125

TTG GTA CGC TGT GTG GAT GGC TCC TCC TCT TCC TTC CGC TCC AAG AAG              792
Leu Val Arg Cys Val Asp Gly Ser Ser Ser Ser Phe Arg Ser Lys Lys
                130                 135                 140

CCC ATA GTA GGG GTC ATT GGG CCT GGC TCC AGT TCT GTA GCC ATT CAG              840
Pro Ile Val Gly Val Ile Gly Pro Gly Ser Ser Ser Val Ala Ile Gln
            145                 150                 155

GTC CAG AAT TTG CTC CAG CTT TTC AAC ATA CCT CAG ATT GCT TAC TCA              888
Val Gln Asn Leu Leu Gln Leu Phe Asn Ile Pro Gln Ile Ala Tyr Ser
        160                 165                 170

GCA ACC AGC ATG GAT CTG AGT GAC AAG ACT CTG TTC AAA TAT TTC ATG              936
Ala Thr Ser Met Asp Leu Ser Asp Lys Thr Leu Phe Lys Tyr Phe Met
175                 180                 185

AGG GTT GTG CCT TCA GAT GCT CAG CAG GCA AGG GCC ATG GTG GAC ATA              984
Arg Val Val Pro Ser Asp Ala Gln Gln Ala Arg Ala Met Val Asp Ile
190                 195                 200                 205

GTG AAG AGG TAC AAC TGG ACC TAT GTA TCA GCC GTG CAC ACA GAA GGC             1032
Val Lys Arg Tyr Asn Trp Thr Tyr Val Ser Ala Val His Thr Glu Gly
                210                 215                 220

AAC TAT GGA GAA AGT GGG ATG GAA GCC TCC AAA GAT ATG TCA GCG AAG             1080
Asn Tyr Gly Glu Ser Gly Met Glu Ala Ser Lys Asp Met Ser Ala Lys
            225                 230                 235

GAA GGG ATT TGC ATC GCC CAC TCT TAC AAA ATC TAC AGT AAT GCA GGG             1128
Glu Gly Ile Cys Ile Ala His Ser Tyr Lys Ile Tyr Ser Asn Ala Gly
        240                 245                 250

GAG CAG AGC TTT GAT AAG CTG CTG AAG AAG CTC ACA AGT CAC TTG CCC             1176
Glu Gln Ser Phe Asp Lys Leu Leu Lys Lys Leu Thr Ser His Leu Pro
255                 260                 265

AAG GCC CGG GTG GTG GCC TGC TTC TGT GAG GGC ATG ACG GTG AGA GGT             1224
Lys Ala Arg Val Val Ala Cys Phe Cys Glu Gly Met Thr Val Arg Gly
270                 275                 280                 285

CTG CTG ATG GCC ATG AGG CGC CTG GGT CTA GCG GGA GAA TTT CTG CTT             1272
Leu Leu Met Ala Met Arg Arg Leu Gly Leu Ala Gly Glu Phe Leu Leu
                290                 295                 300

CTG GGC AGT GAT GGC TGG GCT GAC AGG TAT GAT GTG ACA GAT GGA TAT             1320
Leu Gly Ser Asp Gly Trp Ala Asp Arg Tyr Asp Val Thr Asp Gly Tyr
            305                 310                 315

CAG CGA GAA GCT GTT GGT GGC ATC ACA ATC AAG CTC CAA TCT CCC GAT             1368
Gln Arg Glu Ala Val Gly Gly Ile Thr Ile Lys Leu Gln Ser Pro Asp
        320                 325                 330

GTC AAG TGG TTT GAT GAT TAT TAT CTG AAG CTC CGG CCA GAA ACA AAC             1416
```

|     |     |     |     |     |     |     |     |     |     |     |     |     |     |     |     |      |
| --- | --- | --- | --- | --- | --- | --- | --- | --- | --- | --- | --- | --- | --- | --- | --- | --- |
|     |     | Val | Lys | Trp | Phe | Asp | Asp | Tyr | Tyr | Leu | Lys | Leu | Arg | Pro | Glu | Thr | Asn |
|     |     |     | 335 |     |     |     | 340 |     |     |     |     | 345 |     |     |     |     |     |

```
CAC CGA AAC CCT TGG TTT CAA GAA TTT TGG CAG CAT CGT TTT CAG TGC         1464
His Arg Asn Pro Trp Phe Gln Glu Phe Trp Gln His Arg Phe Gln Cys
350                 355                 360                 365

CGA CTG GAA GCG TTT CCA CAG GAG AAC AGC AAA TAC AAC AAG ACT TGC         1512
Arg Leu Glu Ala Phe Pro Gln Glu Asn Ser Lys Tyr Asn Lys Thr Cys
                    370                 375                 380

AAT AGT TCT CTG ACT CTG AAA ACA CAT CAT GTT CAG GAT TCC AAA ATG         1560
Asn Ser Ser Leu Thr Leu Lys Thr His His Val Gln Asp Ser Lys Met
                385                 390                 395

GGA TTT GTG ATC AAC GCC ATC TAT TCG ATG GCC TAT GGG CTC CAC AAC         1608
Gly Phe Val Ile Asn Ala Ile Tyr Ser Met Ala Tyr Gly Leu His Asn
            400                 405                 410

ATG CAG ATG TCC CTC TGC CCA GGC TAT GCA GGA CTC TGT GAT GCC ATG         1656
Met Gln Met Ser Leu Cys Pro Gly Tyr Ala Gly Leu Cys Asp Ala Met
        415                 420                 425

AAG CCA ATT GAT GGA CGG AAA CTT TTG GAG TCC CTG ATG AAA ACC AAT         1704
Lys Pro Ile Asp Gly Arg Lys Leu Leu Glu Ser Leu Met Lys Thr Asn
430                 435                 440                 445

TTT ACT GGG GTT TCT GGA GAT ACG ATC CTA TTC GAT GAG AAT GGA GAC         1752
Phe Thr Gly Val Ser Gly Asp Thr Ile Leu Phe Asp Glu Asn Gly Asp
                450                 455                 460

TCT CCA GGA AGG TAT GAA ATA ATG AAT TTC AAG GAA ATG GGA AAA GAT         1800
Ser Pro Gly Arg Tyr Glu Ile Met Asn Phe Lys Glu Met Gly Lys Asp
                465                 470                 475

TAC TTT GAT TAT ATC AAC GTT GGA AGT TGG GAC AAT GGA GAA TTA AAA         1848
Tyr Phe Asp Tyr Ile Asn Val Gly Ser Trp Asp Asn Gly Glu Leu Lys
            480                 485                 490

ATG GAT GAT GAT GAA GTA TGG TCC AAG AAA AGC AAC ATC ATC AGA TCT         1896
Met Asp Asp Asp Glu Val Trp Ser Lys Lys Ser Asn Ile Ile Arg Ser
        495                 500                 505

GTG TGC AGT GAA CCA TGT GAG AAA GGC CAG ATC AAG GTG ATC CGA AAG         1944
Val Cys Ser Glu Pro Cys Glu Lys Gly Gln Ile Lys Val Ile Arg Lys
510                 515                 520                 525

GGA GAA GTC AGC TGT TGT TGG ACC TGT ACA CCT TGT AAG GAG AAT GAG         1992
Gly Glu Val Ser Cys Cys Trp Thr Cys Thr Pro Cys Lys Glu Asn Glu
                530                 535                 540

TAT GTC TTT GAT GAG TAC ACA TGC AAG GCA TGC CAA CTG GGG TCT TGG         2040
Tyr Val Phe Asp Glu Tyr Thr Cys Lys Ala Cys Gln Leu Gly Ser Trp
                545                 550                 555

CCC ACT GAT GAT CTC ACA GGT TGT GAC TTG ATC CCA GTA CAG TAT CTT         2088
Pro Thr Asp Asp Leu Thr Gly Cys Asp Leu Ile Pro Val Gln Tyr Leu
            560                 565                 570

CGA TGG GGT GAC CCT GAA CCC ATT GCA GCT GTG GTG TTT GCC TGC CTT         2136
Arg Trp Gly Asp Pro Glu Pro Ile Ala Ala Val Val Phe Ala Cys Leu
        575                 580                 585

GGC CTC CTG GCC ACC CTG TTT GTT ACT GTA GTC TTC ATC ATT TAC CGT         2184
Gly Leu Leu Ala Thr Leu Phe Val Thr Val Val Phe Ile Ile Tyr Arg
590                 595                 600                 605

GAT ACA CCA GTA GTC AAG TCC TCA AGC AGG GAA CTC TGC TAC ATT ATC         2232
Asp Thr Pro Val Val Lys Ser Ser Ser Arg Glu Leu Cys Tyr Ile Ile
                610                 615                 620

CTT GCT GGC ATC TGC CTG GGC TAC TTA TGT ACC TTC TGC CTC ATT GCG         2280
Leu Ala Gly Ile Cys Leu Gly Tyr Leu Cys Thr Phe Cys Leu Ile Ala
                625                 630                 635

AAG CCC AAA CAG ATT TAC TGC TAC CTT CAG AGA ATT GGC ATT GGT CTC         2328
Lys Pro Lys Gln Ile Tyr Cys Tyr Leu Gln Arg Ile Gly Ile Gly Leu
            640                 645                 650

TCC CCA GCC ATG AGC TAC TCA GCC CTT GTA ACA AAG ACC AAC CGT ATT         2376
```

-continued

| | | | | | | | | | | | | |
|---|---|---|---|---|---|---|---|---|---|---|---|---|
| Ser | Pro | Ala | Met | Ser | Tyr | Ser | Ala | Leu | Val | Thr | Lys | Thr | Asn | Arg | Ile |
| | 655 | | | | 660 | | | | | 665 | | | | | |

```
GCA AGG ATC CTG GCT GGC AGC AAG AAG AAG ATC TGT ACC CCC AAG CCC      2424
Ala Arg Ile Leu Ala Gly Ser Lys Lys Lys Ile Cys Thr Pro Lys Pro
670             675                 680                 685

AGA TTC ATG AGT GCC TGT GCC CAG CTA GTG ATT GCT TTC ATT CTC ATA      2472
Arg Phe Met Ser Ala Cys Ala Gln Leu Val Ile Ala Phe Ile Leu Ile
                690                 695                 700

TGC ATC CAG TTG GGC ATC ATC GTT GCC CTC TTT ATA ATG GAG CCT CCT      2520
Cys Ile Gln Leu Gly Ile Ile Val Ala Leu Phe Ile Met Glu Pro Pro
        705                 710                 715

GAC ATA ATG CAT GAC TAC CCA AGC ATT CGA GAA GTC TAC CTG ATC TGT      2568
Asp Ile Met His Asp Tyr Pro Ser Ile Arg Glu Val Tyr Leu Ile Cys
        720                 725                 730

AAC ACC ACC AAC CTA GGA GTT GTC ACT CCA CTT GGA AAC AAT GGA TTG      2616
Asn Thr Thr Asn Leu Gly Val Val Thr Pro Leu Gly Asn Asn Gly Leu
    735                 740                 745

TTG ATT TTG AGC TGC ACC TTC TAT GCG TTC AAG ACC AGA AAT GTT CCA      2664
Leu Ile Leu Ser Cys Thr Phe Tyr Ala Phe Lys Thr Arg Asn Val Pro
750             755                 760                 765

GCT AAC TTC CCC GAG GCC AAG TAT ATC GCC TTC ACA ATG TAC ACG ACC      2712
Ala Asn Phe Pro Glu Ala Lys Tyr Ile Ala Phe Thr Met Tyr Thr Thr
                770                 775                 780

TGC ATT ATA TGG CTA GCT TTT GTT CCA ATC TAC TTT GGC AGC AAC TAC      2760
Cys Ile Ile Trp Leu Ala Phe Val Pro Ile Tyr Phe Gly Ser Asn Tyr
        785                 790                 795

AAA ATC ATC ACC ATG TGT TTC TCG GTC AGC CTC AGT GCC ACA GTG GCC      2808
Lys Ile Ile Thr Met Cys Phe Ser Val Ser Leu Ser Ala Thr Val Ala
        800                 805                 810

CTA GGC TGC ATG TTT GTG CCG AAG GTG TAC ATC ATC CTG GCC AAA CCA      2856
Leu Gly Cys Met Phe Val Pro Lys Val Tyr Ile Ile Leu Ala Lys Pro
815             820                 825

GAG AGA AAC GTG CGC AGC GCC TTC ACC ACA TCT ACC GTG GTG CGC ATG      2904
Glu Arg Asn Val Arg Ser Ala Phe Thr Thr Ser Thr Val Val Arg Met
830             835                 840                 845

CAT GTA GGG GAT GGC AAG TCA TCC TCC GCA GCC AGC AGA TCC AGC AGC      2952
His Val Gly Asp Gly Lys Ser Ser Ser Ala Ala Ser Arg Ser Ser Ser
                850                 855                 860

CTA GTC AAC CTG TGG AAG AGA AGG GGC TCC TCT GGG GAA ACC TTA AGT      3000
Leu Val Asn Leu Trp Lys Arg Arg Gly Ser Ser Gly Glu Thr Leu Ser
        865                 870                 875

TCC AAT GGA AAA TCC GTC ACG TGG GCC CAG AAT GAG AAG AGC AGC CGG      3048
Ser Asn Gly Lys Ser Val Thr Trp Ala Gln Asn Glu Lys Ser Ser Arg
            880                 885                 890

GGG CAG CAC CTG TGG CAG CGC CTG TCC ATC CAC ATC AAC AAG AAA GAA      3096
Gly Gln His Leu Trp Gln Arg Leu Ser Ile His Ile Asn Lys Lys Glu
        895                 900                 905

AAC CCC AAC CAA ACG GCC GTC ATC AAG CCC TTC CCC AAG AGC ACG GAG      3144
Asn Pro Asn Gln Thr Ala Val Ile Lys Pro Phe Pro Lys Ser Thr Glu
910             915                 920                 925

AGC CGT GGC CTG GGC GCT GGC GCT GGC GCA GGC GGG AGC GCT GGG GGC      3192
Ser Arg Gly Leu Gly Ala Gly Ala Gly Ala Gly Gly Ser Ala Gly Gly
                930                 935                 940

GTG GGG GCC ACG GGC GGT GCG GGC TGC GCA GGC GCC GGC CCA GGC GGG      3240
Val Gly Ala Thr Gly Gly Ala Gly Cys Ala Gly Ala Gly Pro Gly Gly
            945                 950                 955

CCC GAG TCC CCA GAC GCC GGC CCC AAG GCG CTG TAT GAT GTG GCC GAG      3288
Pro Glu Ser Pro Asp Ala Gly Pro Lys Ala Leu Tyr Asp Val Ala Glu
    960                 965                 970

GCT GAG GAG CAC TTC CCG GCG CCC GCG CGG CCG CGC TCA CCG TCG CCC      3336
```

-continued

```
Ala Glu Glu His Phe Pro Ala Pro Ala Arg Pro Arg Ser Pro Ser Pro
    975                 980                 985

ATC AGC ACG CTG AGC CAC CGC GCG GGC TCG GCC AGC CGC ACG GAC GAC      3384
Ile Ser Thr Leu Ser His Arg Ala Gly Ser Ala Ser Arg Thr Asp Asp
    990                 995                1000                1005

GAT GTG CCG TCG CTG CAC TCG GAG CCT GTG GCG CGC AGC AGC TCC TCG      3432
Asp Val Pro Ser Leu His Ser Glu Pro Val Ala Arg Ser Ser Ser Ser
                1010                1015                1020

CAG GGC TCC CTC ATG GAG CAG ATC AGC AGT GTG GTC ACC CGC TTC ACG      3480
Gln Gly Ser Leu Met Glu Gln Ile Ser Ser Val Val Thr Arg Phe Thr
                1025                1030                1035

GCC AAC ATC AGC GAG CTC AAC TCC ATG ATG CTG TCC ACC GCG GCC CCC      3528
Ala Asn Ile Ser Glu Leu Asn Ser Met Met Leu Ser Thr Ala Ala Pro
            1040                1045                1050

AGC CCC GGC GTC GGC GCC CCG CTC TGC TCG TCC TAC CTG ATC CCC AAA      3576
Ser Pro Gly Val Gly Ala Pro Leu Cys Ser Ser Tyr Leu Ile Pro Lys
        1055                1060                1065

GAG ATC CAG TTG CCC ACG ACC ATG ACG ACC TTT GCC GAA ATC CAG CCT      3624
Glu Ile Gln Leu Pro Thr Thr Met Thr Thr Phe Ala Glu Ile Gln Pro
1070                1075                1080                1085

CTG CCG GCC ATC GAA GTC ACG GGC GGC GCT CAG CCC GCG GCA GGG GCG      3672
Leu Pro Ala Ile Glu Val Thr Gly Gly Ala Gln Pro Ala Ala Gly Ala
                1090                1095                1100

CAG GCG GCT GGG GAC GCG GCC CGG GAG AGC CCC GCG GCC GGT CCC GAG      3720
Gln Ala Ala Gly Asp Ala Ala Arg Glu Ser Pro Ala Ala Gly Pro Glu
                1105                1110                1115

GCT GCG GCC GCC AAG CCA GAC CTG GAG GAG CTG GTG GCT CTC ACC CCG      3768
Ala Ala Ala Ala Lys Pro Asp Leu Glu Glu Leu Val Ala Leu Thr Pro
            1120                1125                1130

CCG TCC CCC TTC AGA GAC TCG GTG GAC TCG GGG AGC ACA ACC CCC AAC      3816
Pro Ser Pro Phe Arg Asp Ser Val Asp Ser Gly Ser Thr Thr Pro Asn
        1135                1140                1145

TCG CCA GTG TCC GAG TCG GCC CTC TGT ATC CCG TCG TCT CCC AAA TAT      3864
Ser Pro Val Ser Glu Ser Ala Leu Cys Ile Pro Ser Ser Pro Lys Tyr
1150                1155                1160                1165

GAC ACT CTT ATC ATA AGA GAT TAC ACT CAG AGC TCC TCG TCG TTG TGAATGTC 3919
Asp Thr Leu Ile Ile Arg Asp Tyr Thr Gln Ser Ser Ser Ser Leu
                1170                1175                1180

TGGAAAGCAC GCCGGCCTGC GCGTGCGGAG CGGAGCCCCC CGTGTTCACA CACACACAAT   3979

GGCAAGCATA GTCGCCTGGT TACGGCCCAG GGGGAAGATG CCAAGGGCAC CCCTTAATGG   4039

AAACACGAGA TCAGTAGTGC TATCTCATGA CAACCGACGA AGAAAC                  4085
```

(2) INFORMATION FOR SEQ ID NO:8:

(i) SEQUENCE CHARACTERISTICS:
        (A) LENGTH: 1180 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Leu Leu Leu Ile Leu Ser Val Leu Leu Trp Lys Glu Asp Val
1               5                   10                  15

Arg Gly Ser Ala Gln Ser Ser Glu Arg Arg Val Ala His Met Pro
            20                  25                  30

Gly Asp Ile Ile Ile Gly Ala Leu Phe Ser Val His His Gln Pro Thr
        35                  40                  45

Val Asp Lys Val His Glu Arg Lys Cys Gly Ala Val Arg Glu Gln Tyr
    50                  55                  60
```

-continued

```
Gly Ile Gln Arg Val Glu Ala Met Leu His Thr Leu Glu Arg Ile Asn
 65                  70                  75                  80

Ser Asp Pro Thr Leu Leu Pro Asn Ile Thr Leu Gly Cys Glu Ile Arg
                 85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Gly Leu Val Arg
        115                 120                 125

Cys Val Asp Gly Ser Ser Ser Phe Arg Ser Lys Lys Pro Ile Val
130                 135                 140

Gly Val Ile Gly Pro Gly Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
                180                 185                 190

Pro Ser Asp Ala Gln Gln Ala Arg Ala Met Val Asp Ile Val Lys Arg
                195                 200                 205

Tyr Asn Trp Thr Tyr Val Ser Ala Val His Thr Glu Gly Asn Tyr Gly
210                 215                 220

Glu Ser Gly Met Glu Ala Ser Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
                260                 265                 270

Val Val Ala Cys Phe Cys Glu Gly Met Thr Val Arg Gly Leu Leu Met
                275                 280                 285

Ala Met Arg Arg Leu Gly Leu Ala Gly Glu Phe Leu Leu Leu Gly Ser
290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
                340                 345                 350

Pro Trp Phe Gln Glu Phe Trp Gln His Arg Phe Gln Cys Arg Leu Glu
                355                 360                 365

Ala Phe Pro Gln Glu Asn Ser Lys Tyr Asn Lys Thr Cys Asn Ser Ser
370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
                420                 425                 430

Asp Gly Arg Lys Leu Leu Glu Ser Leu Met Lys Thr Asn Phe Thr Gly
                435                 440                 445

Val Ser Gly Asp Thr Ile Leu Phe Asp Glu Asn Gly Asp Ser Pro Gly
                450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
```

-continued

```
                485                 490                 495
Asp Glu Val Trp Ser Lys Lys Ser Asn Ile Ile Arg Ser Val Cys Ser
                500                 505                 510
Glu Pro Cys Glu Lys Gly Gln Ile Lys Val Ile Arg Lys Gly Glu Val
                515                 520                 525
Ser Cys Cys Trp Thr Cys Thr Pro Cys Lys Glu Asn Glu Tyr Val Phe
                530                 535                 540
Asp Glu Tyr Thr Cys Lys Ala Cys Gln Leu Gly Ser Trp Pro Thr Asp
545                             550                 555                 560
Asp Leu Thr Gly Cys Asp Leu Ile Pro Val Gln Tyr Leu Arg Trp Gly
                        565                 570                 575
Asp Pro Glu Pro Ile Ala Ala Val Val Phe Ala Cys Leu Gly Leu Leu
                    580                 585                 590
Ala Thr Leu Phe Val Thr Val Phe Ile Ile Tyr Arg Asp Thr Pro
                595                 600                 605
Val Val Lys Ser Ser Ser Arg Glu Leu Cys Tyr Ile Ile Leu Ala Gly
                610                 615                 620
Ile Cys Leu Gly Tyr Leu Cys Thr Phe Cys Leu Ile Ala Lys Pro Lys
625                         630                 635                 640
Gln Ile Tyr Cys Tyr Leu Gln Arg Ile Gly Ile Gly Leu Ser Pro Ala
                        645                 650                 655
Met Ser Tyr Ser Ala Leu Val Thr Lys Thr Asn Arg Ile Ala Arg Ile
                    660                 665                 670
Leu Ala Gly Ser Lys Lys Lys Ile Cys Thr Pro Lys Pro Arg Phe Met
                675                 680                 685
Ser Ala Cys Ala Gln Leu Val Ile Ala Phe Ile Leu Ile Cys Ile Gln
                690                 695                 700
Leu Gly Ile Ile Val Ala Leu Phe Ile Met Glu Pro Pro Asp Ile Met
705                             710                 715                 720
His Asp Tyr Pro Ser Ile Arg Glu Val Tyr Leu Ile Cys Asn Thr Thr
                        725                 730                 735
Asn Leu Gly Val Val Thr Pro Leu Gly Asn Asn Gly Leu Leu Ile Leu
                    740                 745                 750
Ser Cys Thr Phe Tyr Ala Phe Lys Thr Arg Asn Val Pro Ala Asn Phe
                755                 760                 765
Pro Glu Ala Lys Tyr Ile Ala Phe Thr Met Tyr Thr Thr Cys Ile Ile
                770                 775                 780
Trp Leu Ala Phe Val Pro Ile Tyr Phe Gly Ser Asn Tyr Lys Ile Ile
785                             790                 795                 800
Thr Met Cys Phe Ser Val Ser Leu Ser Ala Thr Val Ala Leu Gly Cys
                        805                 810                 815
Met Phe Val Pro Lys Val Tyr Ile Ile Leu Ala Lys Pro Glu Arg Asn
                    820                 825                 830
Val Arg Ser Ala Phe Thr Thr Ser Thr Val Val Arg Met His Val Gly
                835                 840                 845
Asp Gly Lys Ser Ser Ser Ala Ala Ser Arg Ser Ser Leu Val Asn
                850                 855                 860
Leu Trp Lys Arg Arg Gly Ser Ser Gly Glu Thr Leu Ser Ser Asn Gly
865                             870                 875                 880
Lys Ser Val Thr Trp Ala Gln Asn Glu Lys Ser Ser Arg Gly Gln His
                        885                 890                 895
Leu Trp Gln Arg Leu Ser Ile His Ile Asn Lys Lys Glu Asn Pro Asn
                    900                 905                 910
```

```
Gln Thr Ala Val Ile Lys Pro Phe Pro Lys Ser Thr Glu Ser Arg Gly
        915                 920                 925

Leu Gly Ala Gly Ala Gly Gly Ser Ala Gly Gly Val Gly Ala
    930                 935                 940

Thr Gly Gly Ala Gly Cys Ala Gly Ala Gly Pro Gly Gly Pro Glu Ser
945                 950                 955                 960

Pro Asp Ala Gly Pro Lys Ala Leu Tyr Asp Val Ala Glu Ala Glu Glu
                965                 970                 975

His Phe Pro Ala Pro Ala Arg Pro Arg Ser Pro Ser Pro Ile Ser Thr
            980                 985                 990

Leu Ser His Arg Ala Gly Ser Ala Ser Arg Thr Asp Asp Val Pro
    995                 1000                1005

Ser Leu His Ser Glu Pro Val Ala Arg Ser Ser Ser Gln Gly Ser
    1010                1015                1020

Leu Met Glu Gln Ile Ser Ser Val Val Thr Arg Phe Thr Ala Asn Ile
1025                1030                1035                1040

Ser Glu Leu Asn Ser Met Met Leu Ser Thr Ala Ala Pro Ser Pro Gly
                1045                1050                1055

Val Gly Ala Pro Leu Cys Ser Ser Tyr Leu Ile Pro Lys Glu Ile Gln
                1060                1065                1070

Leu Pro Thr Thr Met Thr Thr Phe Ala Glu Ile Gln Pro Leu Pro Ala
                1075                1080                1085

Ile Glu Val Thr Gly Gly Ala Gln Pro Ala Ala Gly Ala Gln Ala Ala
                1090                1095                1100

Gly Asp Ala Ala Arg Glu Ser Pro Ala Ala Gly Pro Glu Ala Ala Ala
1105                1110                1115                1120

Ala Lys Pro Asp Leu Glu Glu Leu Val Ala Leu Thr Pro Pro Ser Pro
                1125                1130                1135

Phe Arg Asp Ser Val Asp Ser Gly Ser Thr Thr Pro Asn Ser Pro Val
                1140                1145                1150

Ser Glu Ser Ala Leu Cys Ile Pro Ser Ser Pro Lys Tyr Asp Thr Leu
                1155                1160                1165

Ile Ile Arg Asp Tyr Thr Gln Ser Ser Ser Ser Leu
                1170                1175                1180

(2) INFORMATION FOR SEQ ID NO:9:

(i) SEQUENCE CHARACTERISTICS:
        (A) LENGTH: 4181 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 370..4008
        (D) OTHER INFORMATION: /product= "HUMAN MGLUR5B"
            /note= "Variant of MGLUR5A with 96 base pair
            insertion between nucleotides 2998 and 2999."

(xi) SEQUENCE DESCRIPTION: SEQ ID NO:9:

CAGCTCGGCT GTTCTGCGCA CGCTGAGCGG AGGGAATGAG CTTGAGATCA TCTTGGGGGG      60

GAAGCCGGGG ACTGGAGAGG CCGGCTCTGC CCTGCTGATC CCCGTGGCCC AACTTTTCGG     120

GGGGCTAGCT AGACCGAGTC TCACTGCTCG CAGCGCAGCC AACAGGGGGG TTTAGAAGAT     180

CATGACCACA TGGATCATCT AACTAAATGG TACATGGGGA CAAAATGGTC CTTTAGAAAA     240

TACATCTGAA TTGCTGGCTA ATTTCTTGAT TTGCGACTCA ACGTAGGACA TCGCTTGTTC     300
```

```
GTAGCTATCA GAACCCTCCT GAATTTTCCC CACCATGCTA TCTTTATTGG CTTGAACTCC        360

TTTCCTAAA ATG GTC CTT CTG TTG ATC CTG TCA GTC TTA CTT TGG AAA           408
          Met Val Leu Leu Leu Ile Leu Ser Val Leu Leu Trp Lys
            1               5                   10

GAA GAT GTC CGT GGG AGT GCA CAG TCC AGT GAG AGG AGG GTG GTG GCT         456
Glu Asp Val Arg Gly Ser Ala Gln Ser Ser Glu Arg Arg Val Val Ala
        15                  20                  25

CAC ATG CCG GGT GAC ATC ATT ATT GGA GCT CTC TTT TCT GTT CAT CAC         504
His Met Pro Gly Asp Ile Ile Ile Gly Ala Leu Phe Ser Val His His
 30                  35                  40                  45

CAG CCT ACT GTG GAC AAA GTT CAT GAG AGG AAG TGT GGG GCG GTC CGT         552
Gln Pro Thr Val Asp Lys Val His Glu Arg Lys Cys Gly Ala Val Arg
                    50                  55                  60

GAA CAG TAT GGC ATT CAG AGA GTG GAG GCC ATG CTG CAT ACC CTG GAA         600
Glu Gln Tyr Gly Ile Gln Arg Val Glu Ala Met Leu His Thr Leu Glu
                65                  70                  75

AGG ATC AAT TCA GAC CCC ACA CTC TTG CCC AAC ATC ACA CTG GGC TGT         648
Arg Ile Asn Ser Asp Pro Thr Leu Leu Pro Asn Ile Thr Leu Gly Cys
         80                  85                  90

GAG ATA AGG GAC TCC TGC TGG CAT TCG GCT GTG GCC CTA GAG CAG AGC         696
Glu Ile Arg Asp Ser Cys Trp His Ser Ala Val Ala Leu Glu Gln Ser
         95                  100                 105

ATT GAG TTC ATA AGA GAT TCC CTC ATT TCT TCA GAA GAG GAA GAA GGC         744
Ile Glu Phe Ile Arg Asp Ser Leu Ile Ser Ser Glu Glu Glu Glu Gly
110                 115                 120                 125

TTG GTA CGC TGT GTG GAT GGC TCC TCC TCT TCC TTC CGC TCC AAG AAG         792
Leu Val Arg Cys Val Asp Gly Ser Ser Ser Ser Phe Arg Ser Lys Lys
                    130                 135                 140

CCC ATA GTA GGG GTC ATT GGG CCT GGC TCC AGT TCT GTA GCC ATT CAG         840
Pro Ile Val Gly Val Ile Gly Pro Gly Ser Ser Ser Val Ala Ile Gln
                145                 150                 155

GTC CAG AAT TTG CTC CAG CTT TTC AAC ATA CCT CAG ATT GCT TAC TCA         888
Val Gln Asn Leu Leu Gln Leu Phe Asn Ile Pro Gln Ile Ala Tyr Ser
                160                 165                 170

GCA ACC AGC ATG GAT CTG AGT GAC AAG ACT CTG TTC AAA TAT TTC ATG         936
Ala Thr Ser Met Asp Leu Ser Asp Lys Thr Leu Phe Lys Tyr Phe Met
175                 180                 185

AGG GTT GTG CCT TCA GAT GCT CAG CAG GCA AGG GCC ATG GTG GAC ATA         984
Arg Val Val Pro Ser Asp Ala Gln Gln Ala Arg Ala Met Val Asp Ile
190                 195                 200                 205

GTG AAG AGG TAC AAC TGG ACC TAT GTA TCA GCC GTG CAC ACA GAA GGC        1032
Val Lys Arg Tyr Asn Trp Thr Tyr Val Ser Ala Val His Thr Glu Gly
                210                 215                 220

AAC TAT GGA GAA AGT GGG ATG GAA GCC TCC AAA GAT ATG TCA GCG AAG        1080
Asn Tyr Gly Glu Ser Gly Met Glu Ala Ser Lys Asp Met Ser Ala Lys
                225                 230                 235

GAA GGG ATT TGC ATC GCC CAC TCT TAC AAA ATC TAC AGT AAT GCA GGG        1128
Glu Gly Ile Cys Ile Ala His Ser Tyr Lys Ile Tyr Ser Asn Ala Gly
            240                 245                 250

GAG CAG AGC TTT GAT AAG CTG CTG AAG AAG CTC ACA AGT CAC TTG CCC        1176
Glu Gln Ser Phe Asp Lys Leu Leu Lys Lys Leu Thr Ser His Leu Pro
255                 260                 265

AAG GCC CGG GTG GTG GCC TGC TTC TGT GAG GGC ATG ACG GTG AGA GGT        1224
Lys Ala Arg Val Val Ala Cys Phe Cys Glu Gly Met Thr Val Arg Gly
270                 275                 280                 285

CTG CTG ATG GCC ATG AGG CGC CTG GGT CTA GCG GGA GAA TTT CTG CTT        1272
Leu Leu Met Ala Met Arg Arg Leu Gly Leu Ala Gly Glu Phe Leu Leu
                290                 295                 300

CTG GGC AGT GAT GGC TGG GCT GAC AGG TAT GAT GTG ACA GAT GGA TAT        1320
```

```
Leu Gly Ser Asp Gly Trp Ala Asp Arg Tyr Asp Val Thr Asp Gly Tyr
            305                 310                 315

CAG CGA GAA GCT GTT GGT GGC ATC ACA ATC AAG CTC CAA TCT CCC GAT          1368
Gln Arg Glu Ala Val Gly Gly Ile Thr Ile Lys Leu Gln Ser Pro Asp
        320                 325                 330

GTC AAG TGG TTT GAT GAT TAT TAT CTG AAG CTC CGG CCA GAA ACA AAC          1416
Val Lys Trp Phe Asp Asp Tyr Tyr Leu Lys Leu Arg Pro Glu Thr Asn
335                 340                 345

CAC CGA AAC CCT TGG TTT CAA GAA TTT TGG CAG CAT CGT TTT CAG TGC          1464
His Arg Asn Pro Trp Phe Gln Glu Phe Trp Gln His Arg Phe Gln Cys
350                 355                 360                 365

CGA CTG GAA GCG TTT CCA CAG GAG AAC AGC AAA TAC AAC AAG ACT TGC          1512
Arg Leu Glu Ala Phe Pro Gln Glu Asn Ser Lys Tyr Asn Lys Thr Cys
                370                 375                 380

AAT AGT TCT CTG ACT CTG AAA ACA CAT CAT GTT CAG GAT TCC AAA ATG          1560
Asn Ser Ser Leu Thr Leu Lys Thr His His Val Gln Asp Ser Lys Met
            385                 390                 395

GGA TTT GTG ATC AAC GCC ATC TAT TCG ATG GCC TAT GGG CTC CAC AAC          1608
Gly Phe Val Ile Asn Ala Ile Tyr Ser Met Ala Tyr Gly Leu His Asn
        400                 405                 410

ATG CAG ATG TCC CTC TGC CCA GGC TAT GCA GGA CTC TGT GAT GCC ATG          1656
Met Gln Met Ser Leu Cys Pro Gly Tyr Ala Gly Leu Cys Asp Ala Met
    415                 420                 425

AAG CCA ATT GAT GGA CGG AAA CTT TTG GAG TCC CTG ATG AAA ACC AAT          1704
Lys Pro Ile Asp Gly Arg Lys Leu Leu Glu Ser Leu Met Lys Thr Asn
430                 435                 440                 445

TTT ACT GGG GTT TCT GGA GAT ACG ATC CTA TTC GAT GAG AAT GGA GAC          1752
Phe Thr Gly Val Ser Gly Asp Thr Ile Leu Phe Asp Glu Asn Gly Asp
                450                 455                 460

TCT CCA GGA AGG TAT GAA ATA ATG AAT TTC AAG GAA ATG GGA AAA GAT          1800
Ser Pro Gly Arg Tyr Glu Ile Met Asn Phe Lys Glu Met Gly Lys Asp
            465                 470                 475

TAC TTT GAT TAT ATC AAC GTT GGA AGT TGG GAC AAT GGA GAA TTA AAA          1848
Tyr Phe Asp Tyr Ile Asn Val Gly Ser Trp Asp Asn Gly Glu Leu Lys
        480                 485                 490

ATG GAT GAT GAT GAA GTA TGG TCC AAG AAA AGC AAC ATC ATC AGA TCT          1896
Met Asp Asp Asp Glu Val Trp Ser Lys Lys Ser Asn Ile Ile Arg Ser
    495                 500                 505

GTG TGC AGT GAA CCA TGT GAG AAA GGC CAG ATC AAG GTG ATC CGA AAG          1944
Val Cys Ser Glu Pro Cys Glu Lys Gly Gln Ile Lys Val Ile Arg Lys
510                 515                 520                 525

GGA GAA GTC AGC TGT TGT TGG ACC TGT ACA CCT TGT AAG GAG AAT GAG          1992
Gly Glu Val Ser Cys Cys Trp Thr Cys Thr Pro Cys Lys Glu Asn Glu
                530                 535                 540

TAT GTC TTT GAT GAG TAC ACA TGC AAG GCA TGC CAA CTG GGG TCT TGG          2040
Tyr Val Phe Asp Glu Tyr Thr Cys Lys Ala Cys Gln Leu Gly Ser Trp
            545                 550                 555

CCC ACT GAT GAT CTC ACA GGT TGT GAC TTG ATC CCA GTA CAG TAT CTT          2088
Pro Thr Asp Asp Leu Thr Gly Cys Asp Leu Ile Pro Val Gln Tyr Leu
        560                 565                 570

CGA TGG GGT GAC CCT GAA CCC ATT GCA GCT GTG GTG TTT GCC TGC CTT          2136
Arg Trp Gly Asp Pro Glu Pro Ile Ala Ala Val Val Phe Ala Cys Leu
    575                 580                 585

GGC CTC CTG GCC ACC CTG TTT GTT ACT GTA GTC TTC ATC ATT TAC CGT          2184
Gly Leu Leu Ala Thr Leu Phe Val Thr Val Val Phe Ile Ile Tyr Arg
590                 595                 600                 605

GAT ACA CCA GTA GTC AAG TCC TCA AGC AGG GAA CTC TGC TAC ATT ATC          2232
Asp Thr Pro Val Val Lys Ser Ser Ser Arg Glu Leu Cys Tyr Ile Ile
                610                 615                 620

CTT GCT GGC ATC TGC CTG GGC TAC TTA TGT ACC TTC TGC CTC ATT GCG          2280
```

```
            Leu Ala Gly Ile Cys Leu Gly Tyr Leu Cys Thr Phe Cys Leu Ile Ala
                            625                 630                 635

AAG CCC AAA CAG ATT TAC TGC TAC CTT CAG AGA ATT GGC ATT GGT CTC              2328
Lys Pro Lys Gln Ile Tyr Cys Tyr Leu Gln Arg Ile Gly Ile Gly Leu
            640                 645                 650

TCC CCA GCC ATG AGC TAC TCA GCC CTT GTA ACA AAG ACC AAC CGT ATT              2376
Ser Pro Ala Met Ser Tyr Ser Ala Leu Val Thr Lys Thr Asn Arg Ile
    655                 660                 665

GCA AGG ATC CTG GCT GGC AGC AAG AAG AAG ATC TGT ACC CCC AAG CCC              2424
Ala Arg Ile Leu Ala Gly Ser Lys Lys Lys Ile Cys Thr Pro Lys Pro
670                 675                 680                 685

AGA TTC ATG AGT GCC TGT GCC CAG CTA GTG ATT GCT TTC ATT CTC ATA              2472
Arg Phe Met Ser Ala Cys Ala Gln Leu Val Ile Ala Phe Ile Leu Ile
                690                 695                 700

TGC ATC CAG TTG GGC ATC ATC GTT GCC CTC TTT ATA ATG GAG CCT CCT              2520
Cys Ile Gln Leu Gly Ile Ile Val Ala Leu Phe Ile Met Glu Pro Pro
            705                 710                 715

GAC ATA ATG CAT GAC TAC CCA AGC ATT CGA GAA GTC TAC CTG ATC TGT              2568
Asp Ile Met His Asp Tyr Pro Ser Ile Arg Glu Val Tyr Leu Ile Cys
            720                 725                 730

AAC ACC ACC AAC CTA GGA GTT GTC ACT CCA CTT GGA AAC AAT GGA TTG              2616
Asn Thr Thr Asn Leu Gly Val Val Thr Pro Leu Gly Asn Asn Gly Leu
    735                 740                 745

TTG ATT TTG AGC TGC ACC TTC TAT GCG TTC AAG ACC AGA AAT GTT CCA              2664
Leu Ile Leu Ser Cys Thr Phe Tyr Ala Phe Lys Thr Arg Asn Val Pro
750                 755                 760                 765

GCT AAC TTC CCC GAG GCC AAG TAT ATC GCC TTC ACA ATG TAC ACG ACC              2712
Ala Asn Phe Pro Glu Ala Lys Tyr Ile Ala Phe Thr Met Tyr Thr Thr
                770                 775                 780

TGC ATT ATA TGG CTA GCT TTT GTT CCA ATC TAC TTT GGC AGC AAC TAC              2760
Cys Ile Ile Trp Leu Ala Phe Val Pro Ile Tyr Phe Gly Ser Asn Tyr
            785                 790                 795

AAA ATC ATC ACC ATG TGT TTC TCG GTC AGC CTC AGT GCC ACA GTG GCC              2808
Lys Ile Ile Thr Met Cys Phe Ser Val Ser Leu Ser Ala Thr Val Ala
            800                 805                 810

CTA GGC TGC ATG TTT GTG CCG AAG GTG TAC ATC ATC CTG GCC AAA CCA              2856
Leu Gly Cys Met Phe Val Pro Lys Val Tyr Ile Ile Leu Ala Lys Pro
    815                 820                 825

GAG AGA AAC GTG CGC AGC GCC TTC ACC ACA TCT ACC GTG GTG CGC ATG              2904
Glu Arg Asn Val Arg Ser Ala Phe Thr Thr Ser Thr Val Val Arg Met
830                 835                 840                 845

CAT GTA GGG GAT GGC AAG TCA TCC TCC GCA GCC AGC AGA TCC AGC AGC              2952
His Val Gly Asp Gly Lys Ser Ser Ser Ala Ala Ser Arg Ser Ser Ser
                850                 855                 860

CTA GTC AAC CTG TGG AAG AGA AGG GGC TCC TCT GGG GAA ACC TTA AGG              3000
Leu Val Asn Leu Trp Lys Arg Arg Gly Ser Ser Gly Glu Thr Leu Arg
            865                 870                 875

TAC AAA GAC AGG AGA CTG GCC CAG CAC AAG TCG GAA ATA GAG TGT TTC              3048
Tyr Lys Asp Arg Arg Leu Ala Gln His Lys Ser Glu Ile Glu Cys Phe
            880                 885                 890

ACC CCC AAA GGG AGT ATG GGG AAT GGT GGG AGA GCA ACA ATG AGC AGT              3096
Thr Pro Lys Gly Ser Met Gly Asn Gly Gly Arg Ala Thr Met Ser Ser
    895                 900                 905

TCC AAT GGA AAA TCC GTC ACG TGG GCC CAG AAT GAG AAG AGC AGC CGG              3144
Ser Asn Gly Lys Ser Val Thr Trp Ala Gln Asn Glu Lys Ser Ser Arg
910                 915                 920                 925

GGG CAG CAC CTG TGG CAG CGC CTG TCC ATC CAC ATC AAC AAG AAA GAA              3192
Gly Gln His Leu Trp Gln Arg Leu Ser Ile His Ile Asn Lys Lys Glu
                930                 935                 940

AAC CCC AAC CAA ACG GCC GTC ATC AAG CCC TTC CCC AAG AGC ACG GAG              3240
```

-continued

```
Asn Pro Asn Gln Thr Ala Val Ile Lys Pro Phe Pro Lys Ser Thr Glu
        945                 950                 955

AGC CGT GGC CTG GGC GCT GGC GCT GGC GCA GGC GGG AGC GCT GGG GGC       3288
Ser Arg Gly Leu Gly Ala Gly Ala Gly Ala Gly Gly Ser Ala Gly Gly
        960                 965                 970

GTG GGG GCC ACG GGC GGT GCG GGC TGC GCA GGC GCC GGC CCA GGC GGG       3336
Val Gly Ala Thr Gly Gly Ala Gly Cys Ala Gly Ala Gly Pro Gly Gly
        975                 980                 985

CCC GAG TCC CCA GAC GCC GGC CCC AAG GCG CTG TAT GAT GTG GCC GAG       3384
Pro Glu Ser Pro Asp Ala Gly Pro Lys Ala Leu Tyr Asp Val Ala Glu
990                 995                 1000                1005

GCT GAG GAG CAC TTC CCG GCG CCC GCG CGG CCG CGC TCA CCG TCG CCC       3432
Ala Glu Glu His Phe Pro Ala Pro Ala Arg Pro Arg Ser Pro Ser Pro
                1010                1015                1020

ATC AGC ACG CTG AGC CAC CGC GCG GGC TCG GCC AGC CGC ACG GAC GAC       3480
Ile Ser Thr Leu Ser His Arg Ala Gly Ser Ala Ser Arg Thr Asp Asp
                1025                1030                1035

GAT GTG CCG TCG CTG CAC TCG GAG CCT GTG GCG CGC AGC AGC TCC TCG       3528
Asp Val Pro Ser Leu His Ser Glu Pro Val Ala Arg Ser Ser Ser Ser
                1040                1045                1050

CAG GGC TCC CTC ATG GAG CAG ATC AGC AGT GTG GTC ACC CGC TTC ACG       3576
Gln Gly Ser Leu Met Glu Gln Ile Ser Ser Val Val Thr Arg Phe Thr
                1055                1060                1065

GCC AAC ATC AGC GAG CTC AAC TCC ATG ATG CTG TCC ACC GCG GCC CCC       3624
Ala Asn Ile Ser Glu Leu Asn Ser Met Met Leu Ser Thr Ala Ala Pro
1070                1075                1080                1085

AGC CCC GGC GTC GGC GCC CCG CTC TGC TCG TCC TAC CTG ATC CCC AAA       3672
Ser Pro Gly Val Gly Ala Pro Leu Cys Ser Ser Tyr Leu Ile Pro Lys
                1090                1095                1100

GAG ATC CAG TTG CCC ACG ACC ATG ACG ACC TTT GCC GAA ATC CAG CCT       3720
Glu Ile Gln Leu Pro Thr Thr Met Thr Thr Phe Ala Glu Ile Gln Pro
                1105                1110                1115

CTG CCG GCC ATC GAA GTC ACG GGC GGC GCT CAG CCC GCG GCA GGG GCG       3768
Leu Pro Ala Ile Glu Val Thr Gly Gly Ala Gln Pro Ala Ala Gly Ala
                1120                1125                1130

CAG GCG GCT GGG GAC GCG GCC CGG GAG AGC CCC GCG GCC GGT CCC GAG       3816
Gln Ala Ala Gly Asp Ala Ala Arg Glu Ser Pro Ala Ala Gly Pro Glu
                1135                1140                1145

GCT GCG GCC GCC AAG CCA GAC CTG GAG GAG CTG GTG GCT CTC ACC CCG       3864
Ala Ala Ala Ala Lys Pro Asp Leu Glu Glu Leu Val Ala Leu Thr Pro
1150                1155                1160                1165

CCG TCC CCC TTC AGA GAC TCG GTG GAC TCG GGG AGC ACA ACC CCC AAC       3912
Pro Ser Pro Phe Arg Asp Ser Val Asp Ser Gly Ser Thr Thr Pro Asn
                1170                1175                1180

TCG CCA GTG TCC GAG TCG GCC CTC TGT ATC CCG TCG TCT CCC AAA TAT       3960
Ser Pro Val Ser Glu Ser Ala Leu Cys Ile Pro Ser Ser Pro Lys Tyr
                1185                1190                1195

GAC ACT CTT ATC ATA AGA GAT TAC ACT CAG AGC TCC TCG TCG TTG TGAATGTC 4015
Asp Thr Leu Ile Ile Arg Asp Tyr Thr Gln Ser Ser Ser Ser Leu
                1200                1205                1210

TGGAAAGCAC GCCGGCCTGC GCGTGCGGAG CGGAGCCCCC CGTGTTCACA CACACACAAT    4075

GGCAAGCATA GTCGCCTGGT TACGGCCCAG GGGGAAGATG CCAAGGGCAC CCCTTAATGG    4135

AAACACGAGA TCAGTAGTGC TATCTCATGA CAACCGACGA AGAAAC                   4181
```

(2) INFORMATION FOR SEQ ID NO:10:

(i) SEQUENCE CHARACTERISTICS:
        (A) LENGTH: 1212 amino acids
        (B) TYPE: amino acid
        (D) TOPOLOGY: linear (ii) MOLECULE TYPE: protein (xi) SEQUENCE DESCRIPTION: SEQ ID NO:10:

| Met | Val | Leu | Leu | Leu | Ile | Leu | Ser | Val | Leu | Leu | Trp | Lys | Glu | Asp | Val |
|---|---|---|---|---|---|---|---|---|---|---|---|---|---|---|---|
| 1 | | | | 5 | | | | | 10 | | | | | 15 | |

| Arg | Gly | Ser | Ala | Gln | Ser | Glu | Arg | Arg | Val | Val | Ala | His | Met | Pro |
|---|---|---|---|---|---|---|---|---|---|---|---|---|---|---|
| | | | 20 | | | | 25 | | | | 30 | | | |

| Gly | Asp | Ile | Ile | Ile | Gly | Ala | Leu | Phe | Ser | Val | His | His | Gln | Pro | Thr |
|---|---|---|---|---|---|---|---|---|---|---|---|---|---|---|---|
| | | 35 | | | | | 40 | | | | | 45 | | | |

| Val | Asp | Lys | Val | His | Glu | Arg | Lys | Cys | Gly | Ala | Val | Arg | Glu | Gln | Tyr |
|---|---|---|---|---|---|---|---|---|---|---|---|---|---|---|---|
| | 50 | | | | | 55 | | | | | 60 | | | | |

| Gly | Ile | Gln | Arg | Val | Glu | Ala | Met | Leu | His | Thr | Leu | Glu | Arg | Ile | Asn |
|---|---|---|---|---|---|---|---|---|---|---|---|---|---|---|---|
| 65 | | | | | 70 | | | | | 75 | | | | | 80 |

| Ser | Asp | Pro | Thr | Leu | Leu | Pro | Asn | Ile | Thr | Leu | Gly | Cys | Glu | Ile | Arg |
|---|---|---|---|---|---|---|---|---|---|---|---|---|---|---|---|
| | | | | 85 | | | | | 90 | | | | | 95 | |

| Asp | Ser | Cys | Trp | His | Ser | Ala | Val | Ala | Leu | Glu | Gln | Ser | Ile | Glu | Phe |
|---|---|---|---|---|---|---|---|---|---|---|---|---|---|---|---|
| | | | 100 | | | | | 105 | | | | | 110 | | |

| Ile | Arg | Asp | Ser | Leu | Ile | Ser | Ser | Glu | Glu | Glu | Gly | Leu | Val | Arg |
|---|---|---|---|---|---|---|---|---|---|---|---|---|---|---|
| | | 115 | | | | | 120 | | | | | 125 | | |

| Cys | Val | Asp | Gly | Ser | Ser | Ser | Phe | Arg | Ser | Lys | Lys | Pro | Ile | Val |
|---|---|---|---|---|---|---|---|---|---|---|---|---|---|---|
| | 130 | | | | | 135 | | | | | 140 | | | |

| Gly | Val | Ile | Gly | Pro | Gly | Ser | Ser | Ser | Val | Ala | Ile | Gln | Val | Gln | Asn |
|---|---|---|---|---|---|---|---|---|---|---|---|---|---|---|---|
| 145 | | | | | 150 | | | | | 155 | | | | | 160 |

| Leu | Leu | Gln | Leu | Phe | Asn | Ile | Pro | Gln | Ile | Ala | Tyr | Ser | Ala | Thr | Ser |
|---|---|---|---|---|---|---|---|---|---|---|---|---|---|---|---|
| | | | | 165 | | | | | 170 | | | | | 175 | |

| Met | Asp | Leu | Ser | Asp | Lys | Thr | Leu | Phe | Lys | Tyr | Phe | Met | Arg | Val | Val |
|---|---|---|---|---|---|---|---|---|---|---|---|---|---|---|---|
| | | | 180 | | | | | 185 | | | | | 190 | | |

| Pro | Ser | Asp | Ala | Gln | Gln | Ala | Arg | Ala | Met | Val | Asp | Ile | Val | Lys | Arg |
|---|---|---|---|---|---|---|---|---|---|---|---|---|---|---|---|
| | | 195 | | | | | 200 | | | | | 205 | | | |

| Tyr | Asn | Trp | Thr | Tyr | Val | Ser | Ala | Val | His | Thr | Glu | Gly | Asn | Tyr | Gly |
|---|---|---|---|---|---|---|---|---|---|---|---|---|---|---|---|
| | 210 | | | | | 215 | | | | | 220 | | | | |

| Glu | Ser | Gly | Met | Glu | Ala | Ser | Lys | Asp | Met | Ser | Ala | Lys | Glu | Gly | Ile |
|---|---|---|---|---|---|---|---|---|---|---|---|---|---|---|---|
| 225 | | | | | 230 | | | | | 235 | | | | | 240 |

| Cys | Ile | Ala | His | Ser | Tyr | Lys | Ile | Tyr | Ser | Asn | Ala | Gly | Glu | Gln | Ser |
|---|---|---|---|---|---|---|---|---|---|---|---|---|---|---|---|
| | | | | 245 | | | | | 250 | | | | | 255 | |

| Phe | Asp | Lys | Leu | Leu | Lys | Lys | Leu | Thr | Ser | His | Leu | Pro | Lys | Ala | Arg |
|---|---|---|---|---|---|---|---|---|---|---|---|---|---|---|---|
| | | | | 260 | | | | | 265 | | | | | 270 | |

| Val | Val | Ala | Cys | Phe | Cys | Glu | Gly | Met | Thr | Val | Arg | Gly | Leu | Leu | Met |
|---|---|---|---|---|---|---|---|---|---|---|---|---|---|---|---|
| | | | 275 | | | | | 280 | | | | | 285 | | |

| Ala | Met | Arg | Arg | Leu | Gly | Leu | Ala | Gly | Glu | Phe | Leu | Leu | Leu | Gly | Ser |
|---|---|---|---|---|---|---|---|---|---|---|---|---|---|---|---|
| | 290 | | | | | 295 | | | | | 300 | | | | |

| Asp | Gly | Trp | Ala | Asp | Arg | Tyr | Asp | Val | Thr | Asp | Gly | Tyr | Gln | Arg | Glu |
|---|---|---|---|---|---|---|---|---|---|---|---|---|---|---|---|
| 305 | | | | | 310 | | | | | 315 | | | | | 320 |

| Ala | Val | Gly | Gly | Ile | Thr | Ile | Lys | Leu | Gln | Ser | Pro | Asp | Val | Lys | Trp |
|---|---|---|---|---|---|---|---|---|---|---|---|---|---|---|---|
| | | | | 325 | | | | | 330 | | | | | 335 | |

| Phe | Asp | Asp | Tyr | Tyr | Leu | Lys | Leu | Arg | Pro | Glu | Thr | Asn | His | Arg | Asn |
|---|---|---|---|---|---|---|---|---|---|---|---|---|---|---|---|
| | | | 340 | | | | | 345 | | | | | 350 | | |

| Pro | Trp | Phe | Gln | Glu | Phe | Trp | Gln | His | Arg | Phe | Gln | Cys | Arg | Leu | Glu |
|---|---|---|---|---|---|---|---|---|---|---|---|---|---|---|---|
| | | | 355 | | | | | 360 | | | | | 365 | | |

| Ala | Phe | Pro | Gln | Glu | Asn | Ser | Lys | Tyr | Asn | Lys | Thr | Cys | Asn | Ser | Ser |
|---|---|---|---|---|---|---|---|---|---|---|---|---|---|---|---|
| | 370 | | | | | 375 | | | | | 380 | | | | |

| Leu | Thr | Leu | Lys | Thr | His | His | Val | Gln | Asp | Ser | Lys | Met | Gly | Phe | Val |
|---|---|---|---|---|---|---|---|---|---|---|---|---|---|---|---|
| 385 | | | | | 390 | | | | | 395 | | | | | 400 |

-continued

```
Ile Asn Ala Ile Tyr Ser Met Ala Tyr Gly Leu His Asn Met Gln Met
            405                 410                 415

Ser Leu Cys Pro Gly Tyr Ala Gly Leu Cys Asp Ala Met Lys Pro Ile
            420                 425                 430

Asp Gly Arg Lys Leu Leu Glu Ser Leu Met Lys Thr Asn Phe Thr Gly
            435                 440                 445

Val Ser Gly Asp Thr Ile Leu Phe Asp Glu Asn Gly Asp Ser Pro Gly
450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
            500                 505                 510

Glu Pro Cys Glu Lys Gly Gln Ile Lys Val Ile Arg Lys Gly Glu Val
            515                 520                 525

Ser Cys Cys Trp Thr Cys Thr Pro Cys Lys Glu Asn Glu Tyr Val Phe
            530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Phe Ile Ile Tyr Arg Asp Thr Pro
            595                 600                 605

Val Val Lys Ser Ser Arg Glu Leu Cys Tyr Ile Ile Leu Ala Gly
            610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
                660                 665                 670

Leu Ala Gly Ser Lys Lys Lys Ile Cys Thr Pro Lys Pro Arg Phe Met
            675                 680                 685

Ser Ala Cys Ala Gln Leu Val Ile Ala Phe Ile Leu Ile Cys Ile Gln
            690                 695                 700

Leu Gly Ile Ile Val Ala Leu Phe Ile Met Glu Pro Pro Asp Ile Met
705                 710                 715                 720

His Asp Tyr Pro Ser Ile Arg Glu Val Tyr Leu Ile Cys Asn Thr Thr
                725                 730                 735

Asn Leu Gly Val Val Thr Pro Leu Gly Asn Asn Gly Leu Leu Ile Leu
            740                 745                 750

Ser Cys Thr Phe Tyr Ala Phe Lys Thr Arg Asn Val Pro Ala Asn Phe
            755                 760                 765

Pro Glu Ala Lys Tyr Ile Ala Phe Thr Met Tyr Thr Thr Cys Ile Ile
            770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Lys Val Tyr Ile Ile Leu Ala Lys Pro Glu Arg Asn
            820                 825                 830
```

```
Val Arg Ser Ala Phe Thr Thr Ser Thr Val Val Arg Met His Val Gly
        835                 840                 845

Asp Gly Lys Ser Ser Ser Ala Ala Ser Arg Ser Ser Ser Leu Val Asn
        850                 855                 860

Leu Trp Lys Arg Arg Gly Ser Ser Gly Glu Thr Leu Arg Tyr Lys Asp
865                 870                 875                 880

Arg Arg Leu Ala Gln His Lys Ser Glu Ile Glu Cys Phe Thr Pro Lys
                885                 890                 895

Gly Ser Met Gly Asn Gly Gly Arg Ala Thr Met Ser Ser Ser Asn Gly
            900                 905                 910

Lys Ser Val Thr Trp Ala Gln Asn Glu Lys Ser Ser Arg Gly Gln His
            915                 920                 925

Leu Trp Gln Arg Leu Ser Ile His Ile Asn Lys Lys Glu Asn Pro Asn
            930                 935                 940

Gln Thr Ala Val Ile Lys Pro Phe Pro Lys Ser Thr Glu Ser Arg Gly
945                 950                 955                 960

Leu Gly Ala Gly Ala Gly Ala Gly Ser Ala Gly Gly Val Gly Ala
                965                 970                 975

Thr Gly Gly Ala Gly Cys Ala Gly Ala Gly Pro Gly Gly Pro Glu Ser
            980                 985                 990

Pro Asp Ala Gly Pro Lys Ala Leu Tyr Asp Val Ala Glu Ala Glu Glu
        995                 1000                1005

His Phe Pro Ala Pro Ala Arg Pro Arg Ser Pro Ser Pro Ile Ser Thr
    1010                1015                1020

Leu Ser His Arg Ala Gly Ser Ala Ser Arg Thr Asp Asp Val Pro
1025                1030                1035                1040

Ser Leu His Ser Glu Pro Val Ala Arg Ser Ser Ser Ser Gln Gly Ser
                1045                1050                1055

Leu Met Glu Gln Ile Ser Ser Val Val Thr Arg Phe Thr Ala Asn Ile
            1060                1065                1070

Ser Glu Leu Asn Ser Met Met Leu Ser Thr Ala Ala Pro Ser Pro Gly
            1075                1080                1085

Val Gly Ala Pro Leu Cys Ser Ser Tyr Leu Ile Pro Lys Glu Ile Gln
    1090                1095                1100

Leu Pro Thr Thr Met Thr Thr Phe Ala Glu Ile Gln Pro Leu Pro Ala
1105                1110                1115                1120

Ile Glu Val Thr Gly Gly Ala Gln Pro Ala Ala Gly Ala Gln Ala Ala
            1125                1130                1135

Gly Asp Ala Ala Arg Glu Ser Pro Ala Ala Gly Pro Glu Ala Ala Ala
            1140                1145                1150

Ala Lys Pro Asp Leu Glu Glu Leu Val Ala Leu Thr Pro Pro Ser Pro
        1155                1160                1165

Phe Arg Asp Ser Val Asp Ser Gly Ser Thr Thr Pro Asn Ser Pro Val
    1170                1175                1180

Ser Glu Ser Ala Leu Cys Ile Pro Ser Ser Pro Lys Tyr Asp Thr Leu
1185                1190                1195                1200

Ile Ile Arg Asp Tyr Thr Gln Ser Ser Ser Ser Leu
            1205                1210
```

(2) INFORMATION FOR SEQ ID NO:11:

(i) SEQUENCE CHARACTERISTICS:
        (A) LENGTH: 3282 base pairs
        (B) TYPE: nucleic acid
        (C) STRANDEDNESS: both

```
        (D) TOPOLOGY: both (ii) MOLECULE TYPE: cDNA (ix) FEATURE:
         (A) NAME/KEY: CDS
         (B) LOCATION: 370..3003
         (D) OTHER INFORMATION: /product= "HUMAN MGLUR5C"
             /note= "Variant of MGLUR5A with truncated 3' end."

(xi) SEQUENCE DESCRIPTION: SEQ ID NO:11:

CAGCTCGGCT GTTCTGCGCA CGCTGAGCGG AGGGAATGAG CTTGAGATCA TCTTGGGGGG         60

GAAGCCGGGG ACTGGAGAGG CCGGCTCTGC CCTGCTGATC CCCGTGGCCC AACTTTTCGG        120

GGGGCTAGCT AGACCGAGTC TCACTGCTCG CAGCGCAGCC AACAGGGGGG TTTAGAAGAT        180

CATGACCACA TGGATCATCT AACTAAATGG TACATGGGGA CAAAATGGTC CTTTAGAAAA        240

TACATCTGAA TTGCTGGCTA ATTTCTTGAT TTGCGACTCA ACGTAGGACA TCGCTTGTTC        300

GTAGCTATCA GAACCCTCCT GAATTTTCCC CACCATGCTA TCTTTATTGG CTTGAACTCC        360

TTTCCTAAA ATG GTC CTT CTG TTG ATC CTG TCA GTC TTA CTT TGG AAA           408
          Met Val Leu Leu Leu Ile Leu Ser Val Leu Leu Trp Lys
           1               5                  10

GAA GAT GTC CGT GGG AGT GCA CAG TCC AGT GAG AGG AGG GTG GTG GCT         456
Glu Asp Val Arg Gly Ser Ala Gln Ser Ser Glu Arg Arg Val Val Ala
 15                  20                  25

CAC ATG CCG GGT GAC ATC ATT ATT GGA GCT CTC TTT TCT GTT CAT CAC         504
His Met Pro Gly Asp Ile Ile Ile Gly Ala Leu Phe Ser Val His His
 30                  35                  40                  45

CAG CCT ACT GTG GAC AAA GTT CAT GAG AGG AAG TGT GGG GCG TCC CGT         552
Gln Pro Thr Val Asp Lys Val His Glu Arg Lys Cys Gly Ala Val Arg
                 50                  55                  60

GAA CAG TAT GGC ATT CAG AGA GTG GAG GCC ATG CTG CAT ACC CTG GAA         600
Glu Gln Tyr Gly Ile Gln Arg Val Glu Ala Met Leu His Thr Leu Glu
         65                  70                  75

AGG ATC AAT TCA GAC CCC ACA CTC TTG CCC AAC ATC ACA CTG GGC TGT         648
Arg Ile Asn Ser Asp Pro Thr Leu Leu Pro Asn Ile Thr Leu Gly Cys
 80                  85                  90

GAG ATA AGG GAC TCC TGC TGG CAT TCG GCT GTG GCC CTA GAG CAG AGC         696
Glu Ile Arg Asp Ser Cys Trp His Ser Ala Val Ala Leu Glu Gln Ser
             95                 100                 105

ATT GAG TTC ATA AGA GAT TCC CTC ATT TCT TCA GAA GAG GAA GAA GGC         744
Ile Glu Phe Ile Arg Asp Ser Leu Ile Ser Ser Glu Glu Glu Glu Gly
110                 115                 120                 125

TTG GTA CGC TGT GTG GAT GGC TCC TCC TCT TCC TTC CGC TCC AAG AAG         792
Leu Val Arg Cys Val Asp Gly Ser Ser Ser Ser Phe Arg Ser Lys Lys
                130                 135                 140

CCC ATA GTA GGG GTC ATT GGG CCT GGC TCC AGT TCT GTA GCC ATT CAG         840
Pro Ile Val Gly Val Ile Gly Pro Gly Ser Ser Ser Val Ala Ile Gln
            145                 150                 155

GTC CAG AAT TTG CTC CAG CTT TTC AAC ATA CCT CAG ATT GCT TAC TCA         888
Val Gln Asn Leu Leu Gln Leu Phe Asn Ile Pro Gln Ile Ala Tyr Ser
        160                 165                 170

GCA ACC AGC ATG GAT CTG AGT GAC AAG ACT CTG TTC AAA TAT TTC ATG         936
Ala Thr Ser Met Asp Leu Ser Asp Lys Thr Leu Phe Lys Tyr Phe Met
    175                 180                 185

AGG GTT GTG CCT TCA GAT GCT CAG CAG GCA AGG GCC ATG GTG GAC ATA         984
Arg Val Val Pro Ser Asp Ala Gln Gln Ala Arg Ala Met Val Asp Ile
190                 195                 200                 205

GTG AAG AGG TAC AAC TGG ACC TAT GTA TCA GCC GTG CAC ACA GAA GGC        1032
Val Lys Arg Tyr Asn Trp Thr Tyr Val Ser Ala Val His Thr Glu Gly
                210                 215                 220
```

| | |
|---|---|
| AAC TAT GGA GAA AGT GGG ATG GAA GCC TCC AAA GAT ATG TCA GCG AAG<br>Asn Tyr Gly Glu Ser Gly Met Glu Ala Ser Lys Asp Met Ser Ala Lys<br>225                              230                        235 | 1080 |
| GAA GGG ATT TGC ATC GCC CAC TCT TAC AAA ATC TAC AGT AAT GCA GGG<br>Glu Gly Ile Cys Ile Ala His Ser Tyr Lys Ile Tyr Ser Asn Ala Gly<br>        240                        245                        250 | 1128 |
| GAG CAG AGC TTT GAT AAG CTG CTG AAG AAG CTC ACA AGT CAC TTG CCC<br>Glu Gln Ser Phe Asp Lys Leu Leu Lys Lys Leu Thr Ser His Leu Pro<br>255                              260                        265 | 1176 |
| AAG GCC CGG GTG GTG GCC TGC TTC TGT GAG GGC ATG ACG GTG AGA GGT<br>Lys Ala Arg Val Val Ala Cys Phe Cys Glu Gly Met Thr Val Arg Gly<br>270                              275                    280                    285 | 1224 |
| CTG CTG ATG GCC ATG AGG CGC CTG GGT CTA GCG GGA GAA TTT CTG CTT<br>Leu Leu Met Ala Met Arg Arg Leu Gly Leu Ala Gly Glu Phe Leu Leu<br>                            290                        295                    300 | 1272 |
| CTG GGC AGT GAT GGC TGG GCT GAC AGG TAT GAT GTG ACA GAT GGA TAT<br>Leu Gly Ser Asp Gly Trp Ala Asp Arg Tyr Asp Val Thr Asp Gly Tyr<br>305                              310                        315 | 1320 |
| CAG CGA GAA GCT GTT GGT GGC ATC ACA ATC AAG CTC CAA TCT CCC GAT<br>Gln Arg Glu Ala Val Gly Gly Ile Thr Ile Lys Leu Gln Ser Pro Asp<br>        320                        325                        330 | 1368 |
| GTC AAG TGG TTT GAT GAT TAT TAT CTG AAG CTC CGG CCA GAA ACA AAC<br>Val Lys Trp Phe Asp Asp Tyr Tyr Leu Lys Leu Arg Pro Glu Thr Asn<br>335                              340                        345 | 1416 |
| CAC CGA AAC CCT TGG TTT CAA GAA TTT TGG CAG CAT CGT TTT CAG TGC<br>His Arg Asn Pro Trp Phe Gln Glu Phe Trp Gln His Arg Phe Gln Cys<br>350                              355                    360                    365 | 1464 |
| CGA CTG GAA GCG TTT CCA CAG GAG AAC AGC AAA TAC AAC AAG ACT TGC<br>Arg Leu Glu Ala Phe Pro Gln Glu Asn Ser Lys Tyr Asn Lys Thr Cys<br>                            370                        375                    380 | 1512 |
| AAT AGT TCT CTG ACT CTG AAA ACA CAT CAT GTT CAG GAT TCC AAA ATG<br>Asn Ser Ser Leu Thr Leu Lys Thr His His Val Gln Asp Ser Lys Met<br>                      385                        390                    395 | 1560 |
| GGA TTT GTG ATC AAC GCC ATC TAT TCG ATG GCC TAT GGG CTC CAC AAC<br>Gly Phe Val Ile Asn Ala Ile Tyr Ser Met Ala Tyr Gly Leu His Asn<br>                  400                        405                    410 | 1608 |
| ATG CAG ATG TCC CTC TGC CCA GGC TAT GCA GGA CTC TGT GAT GCC ATG<br>Met Gln Met Ser Leu Cys Pro Gly Tyr Ala Gly Leu Cys Asp Ala Met<br>                415                        420                    425 | 1656 |
| AAG CCA ATT GAT GGA CGG AAA CTT TTG GAG TCC CTG ATG AAA ACC AAT<br>Lys Pro Ile Asp Gly Arg Lys Leu Leu Glu Ser Leu Met Lys Thr Asn<br>430                              435                    440                    445 | 1704 |
| TTT ACT GGG GTT TCT GGA GAT ACG ATC CTA TTC GAT GAG AAT GGA GAC<br>Phe Thr Gly Val Ser Gly Asp Thr Ile Leu Phe Asp Glu Asn Gly Asp<br>                      450                        455                    460 | 1752 |
| TCT CCA GGA AGG TAT GAA ATA ATG AAT TTC AAG GAA ATG GGA AAA GAT<br>Ser Pro Gly Arg Tyr Glu Ile Met Asn Phe Lys Glu Met Gly Lys Asp<br>                465                        470                    475 | 1800 |
| TAC TTT GAT TAT ATC AAC GTT GGA AGT TGG GAC AAT GGA GAA TTA AAA<br>Tyr Phe Asp Tyr Ile Asn Val Gly Ser Trp Asp Asn Gly Glu Leu Lys<br>                  480                        485                    490 | 1848 |
| ATG GAT GAT GAT GAA GTA TGG TCC AAG AAA AGC AAC ATC ATC AGA TCT<br>Met Asp Asp Asp Glu Val Trp Ser Lys Lys Ser Asn Ile Ile Arg Ser<br>495                              500                        505 | 1896 |
| GTG TGC AGT GAA CCA TGT GAG AAA GGC CAG ATC AAG GTG ATC CGA AAG<br>Val Cys Ser Glu Pro Cys Glu Lys Gly Gln Ile Lys Val Ile Arg Lys<br>510                              515                    520                    525 | 1944 |
| GGA GAA GTC AGC TGT TGT TGG ACC TGT ACA CCT TGT AAG GAG AAT GAG<br>Gly Glu Val Ser Cys Cys Trp Thr Cys Thr Pro Cys Lys Glu Asn Glu<br>                      530                        535                    540 | 1992 |

-continued

| | |
|---|---|
| TAT GTC TTT GAT GAG TAC ACA TGC AAG GCA TGC CAA CTG GGG TCT TGG<br>Tyr Val Phe Asp Glu Tyr Thr Cys Lys Ala Cys Gln Leu Gly Ser Trp<br>           545                  550                  555 | 2040 |
| CCC ACT GAT GAT CTC ACA GGT TGT GAC TTG ATC CCA GTA CAG TAT CTT<br>Pro Thr Asp Asp Leu Thr Gly Cys Asp Leu Ile Pro Val Gln Tyr Leu<br>           560                  565                  570 | 2088 |
| CGA TGG GGT GAC CCT GAA CCC ATT GCA GCT GTG GTG TTT GCC TGC CTT<br>Arg Trp Gly Asp Pro Glu Pro Ile Ala Ala Val Val Phe Ala Cys Leu<br>           575                  580                  585 | 2136 |
| GGC CTC CTG GCC ACC CTG TTT GTT ACT GTA GTC TTC ATC ATT TAC CGT<br>Gly Leu Leu Ala Thr Leu Phe Val Thr Val Val Phe Ile Ile Tyr Arg<br>590                  595                  600                  605 | 2184 |
| GAT ACA CCA GTA GTC AAG TCC TCA AGC AGG GAA CTC TGC TAC ATT ATC<br>Asp Thr Pro Val Val Lys Ser Ser Ser Arg Glu Leu Cys Tyr Ile Ile<br>                  610                  615                  620 | 2232 |
| CTT GCT GGC ATC TGC CTG GGC TAC TTA TGT ACC TTC TGC CTC ATT GCG<br>Leu Ala Gly Ile Cys Leu Gly Tyr Leu Cys Thr Phe Cys Leu Ile Ala<br>                  625                  630                  635 | 2280 |
| AAG CCC AAA CAG ATT TAC TGC TAC CTT CAG AGA ATT GGC ATT GGT CTC<br>Lys Pro Lys Gln Ile Tyr Cys Tyr Leu Gln Arg Ile Gly Ile Gly Leu<br>           640                  645                  650 | 2328 |
| TCC CCA GCC ATG AGC TAC TCA GCC CTT GTA ACA AAG ACC AAC CGT ATT<br>Ser Pro Ala Met Ser Tyr Ser Ala Leu Val Thr Lys Thr Asn Arg Ile<br>655                  660                  665 | 2376 |
| GCA AGG ATC CTG GCT GGC AGC AAG AAG AAG ATC TGT ACC CCC AAG CCC<br>Ala Arg Ile Leu Ala Gly Ser Lys Lys Lys Ile Cys Thr Pro Lys Pro<br>670                  675                  680                  685 | 2424 |
| AGA TTC ATG AGT GCC TGT GCC CAG CTA GTG ATT GCT TTC ATT CTC ATA<br>Arg Phe Met Ser Ala Cys Ala Gln Leu Val Ile Ala Phe Ile Leu Ile<br>                  690                  695                  700 | 2472 |
| TGC ATC CAG TTG GGC ATC ATC GTT GCC CTC TTT ATA ATG GAG CCT CCT<br>Cys Ile Gln Leu Gly Ile Ile Val Ala Leu Phe Ile Met Glu Pro Pro<br>           705                  710                  715 | 2520 |
| GAC ATA ATG CAT GAC TAC CCA AGC ATT CGA GAA GTC TAC CTG ATC TGT<br>Asp Ile Met His Asp Tyr Pro Ser Ile Arg Glu Val Tyr Leu Ile Cys<br>           720                  725                  730 | 2568 |
| AAC ACC ACC AAC CTA GGA GTT GTC ACT CCA CTT GGA AAC AAT GGA TTG<br>Asn Thr Thr Asn Leu Gly Val Val Thr Pro Leu Gly Asn Asn Gly Leu<br>735                  740                  745 | 2616 |
| TTG ATT TTG AGC TGC ACC TTC TAT GCG TTC AAG ACC AGA AAT GTT CCA<br>Leu Ile Leu Ser Cys Thr Phe Tyr Ala Phe Lys Thr Arg Asn Val Pro<br>750                  755                  760                  765 | 2664 |
| GCT AAC TTC CCC GAG GCC AAG TAT ATC GCC TTC ACA ATG TAC ACG ACC<br>Ala Asn Phe Pro Glu Ala Lys Tyr Ile Ala Phe Thr Met Tyr Thr Thr<br>                  770                  775                  780 | 2712 |
| TGC ATT ATA TGG CTA GCT TTT GTT CCA ATC TAC TTT GGC AGC AAC TAC<br>Cys Ile Ile Trp Leu Ala Phe Val Pro Ile Tyr Phe Gly Ser Asn Tyr<br>                  785                  790                  795 | 2760 |
| AAA ATC ATC ACC ATG TGT TTC TCG GTC AGC CTC AGT GCC ACA GTG GCC<br>Lys Ile Ile Thr Met Cys Phe Ser Val Ser Leu Ser Ala Thr Val Ala<br>           800                  805                  810 | 2808 |
| CTA GGC TGC ATG TTT GTG CCG ACG GTG TAC ATC ATC CTG GCC AAA CCA<br>Leu Gly Cys Met Phe Val Pro Thr Val Tyr Ile Ile Leu Ala Lys Pro<br>815                  820                  825 | 2856 |
| GAG AGA AAC GTG CGC AGC GCC TTC ACC ACA TCT ACC GTG GTG CGC ATG<br>Glu Arg Asn Val Arg Ser Ala Phe Thr Thr Ser Thr Val Val Arg Met<br>830                  835                  840                  845 | 2904 |
| CAT GTA GGG GAT GGC AAG TCA TCC TCC GCA GCC AGC AGA TCC AGC AGC<br>His Val Gly Asp Gly Lys Ser Ser Ser Ala Ala Ser Arg Ser Ser Ser<br>                  850                  855                  860 | 2952 |

```
CTA GTC AAC CTG TGG AAG AGA AGG GGC TCC TCT GGG GAA ACC TTA AGG         3000
Leu Val Asn Leu Trp Lys Arg Arg Gly Ser Ser Gly Glu Thr Leu Arg
            865                 870                 875

TAAAAGTTGT GGGGGCTTAC AGGGATGCTG GCCCCTAAAA CTGGAGCAGA GGCATGTGTT        3060

TCCTGGGTCT TTTAAATGGG AGAAATCTGG GTAAATGACA CCATCTGAGG CAGGGTGACT        3120

TACGGCATGG ACCTCCTCAT AAAATGGTAT TTATGGGGTT AATGGGATGT GGCTCCACTT        3180

ACTTAGCCCA AGTCTAGAAA CATGGAAGTC AAACTCTCTA ATAAAGCAGA GCTACAGCGT        3240

CGGGGGAGTG ACGTTTGACA GGGCAGACAG ACCAGAGTTC AG                          3282

(2) INFORMATION FOR SEQ ID NO:12:

(i) SEQUENCE CHARACTERISTICS:
        (A) LENGTH: 877 amino acids
        (B) TYPE: amino acid
        (D) TOPOLOGY: linear (ii) MOLECULE TYPE: protein (xi) SEQUENCE DESCRIPTION: SEQ ID NO:12:
```

Met Val Leu Leu Leu Ile Leu Ser Val Leu Leu Trp Lys Glu Asp Val
 1               5                  10                  15

Arg Gly Ser Ala Gln Ser Ser Glu Arg Arg Val Val Ala His Met Pro
                20                  25                  30

Gly Asp Ile Ile Ile Gly Ala Leu Phe Ser Val His His Gln Pro Thr
            35                  40                  45

Val Asp Lys Val His Glu Arg Lys Cys Gly Ala Val Arg Glu Gln Tyr
        50                  55                  60

Gly Ile Gln Arg Val Glu Ala Met Leu His Thr Leu Glu Arg Ile Asn
65                  70                  75                  80

Ser Asp Pro Thr Leu Leu Pro Asn Ile Thr Leu Gly Cys Glu Ile Arg
                85                  90                  95

Asp Ser Cys Trp His Ser Ala Val Ala Leu Glu Gln Ser Ile Glu Phe
            100                 105                 110

Ile Arg Asp Ser Leu Ile Ser Ser Glu Glu Glu Gly Leu Val Arg
        115                 120                 125

Cys Val Asp Gly Ser Ser Ser Ser Phe Arg Ser Lys Lys Pro Ile Val
130                 135                 140

Gly Val Ile Gly Pro Gly Ser Ser Ser Val Ala Ile Gln Val Gln Asn
145                 150                 155                 160

Leu Leu Gln Leu Phe Asn Ile Pro Gln Ile Ala Tyr Ser Ala Thr Ser
                165                 170                 175

Met Asp Leu Ser Asp Lys Thr Leu Phe Lys Tyr Phe Met Arg Val Val
            180                 185                 190

Pro Ser Asp Ala Gln Gln Ala Arg Ala Met Val Asp Ile Val Lys Arg
        195                 200                 205

Tyr Asn Trp Thr Tyr Val Ser Ala Val His Thr Glu Gly Asn Tyr Gly
        210                 215                 220

Glu Ser Gly Met Glu Ala Ser Lys Asp Met Ser Ala Lys Glu Gly Ile
225                 230                 235                 240

Cys Ile Ala His Ser Tyr Lys Ile Tyr Ser Asn Ala Gly Glu Gln Ser
                245                 250                 255

Phe Asp Lys Leu Leu Lys Lys Leu Thr Ser His Leu Pro Lys Ala Arg
            260                 265                 270

Val Val Ala Cys Phe Cys Glu Gly Met Thr Val Arg Gly Leu Leu Met
        275                 280                 285

```
Ala Met Arg Arg Leu Gly Leu Ala Gly Glu Phe Leu Leu Gly Ser
    290                 295                 300

Asp Gly Trp Ala Asp Arg Tyr Asp Val Thr Asp Gly Tyr Gln Arg Glu
305                 310                 315                 320

Ala Val Gly Gly Ile Thr Ile Lys Leu Gln Ser Pro Asp Val Lys Trp
                325                 330                 335

Phe Asp Asp Tyr Tyr Leu Lys Leu Arg Pro Glu Thr Asn His Arg Asn
            340                 345                 350

Pro Trp Phe Gln Glu Phe Trp Gln His Arg Phe Gln Cys Arg Leu Glu
            355                 360                 365

Ala Phe Pro Gln Glu Asn Ser Lys Tyr Asn Lys Thr Cys Asn Ser Ser
    370                 375                 380

Leu Thr Leu Lys Thr His His Val Gln Asp Ser Lys Met Gly Phe Val
385                 390                 395                 400

Ile Asn Ala Ile Tyr Ser Met Ala Tyr Gly Leu His Asn Met Gln Met
                405                 410                 415

Ser Leu Cys Pro Gly Tyr Ala Gly Leu Cys Asp Ala Met Lys Pro Ile
                420                 425                 430

Asp Gly Arg Lys Leu Leu Glu Ser Leu Met Lys Thr Asn Phe Thr Gly
            435                 440                 445

Val Ser Gly Asp Thr Ile Leu Phe Asp Glu Asn Gly Asp Ser Pro Gly
    450                 455                 460

Arg Tyr Glu Ile Met Asn Phe Lys Glu Met Gly Lys Asp Tyr Phe Asp
465                 470                 475                 480

Tyr Ile Asn Val Gly Ser Trp Asp Asn Gly Glu Leu Lys Met Asp Asp
                485                 490                 495

Asp Glu Val Trp Ser Lys Lys Ser Asn Ile Ile Arg Ser Val Cys Ser
                500                 505                 510

Glu Pro Cys Glu Lys Gly Gln Ile Lys Val Ile Arg Lys Gly Glu Val
            515                 520                 525

Ser Cys Cys Trp Thr Cys Thr Pro Cys Lys Glu Asn Glu Tyr Val Phe
    530                 535                 540

Asp Glu Tyr Thr Cys Lys Ala Cys Gln Leu Gly Ser Trp Pro Thr Asp
545                 550                 555                 560

Asp Leu Thr Gly Cys Asp Leu Ile Pro Val Gln Tyr Leu Arg Trp Gly
                565                 570                 575

Asp Pro Glu Pro Ile Ala Ala Val Val Phe Ala Cys Leu Gly Leu Leu
            580                 585                 590

Ala Thr Leu Phe Val Thr Val Val Phe Ile Ile Tyr Arg Asp Thr Pro
    595                 600                 605

Val Val Lys Ser Ser Ser Arg Glu Leu Cys Tyr Ile Ile Leu Ala Gly
    610                 615                 620

Ile Cys Leu Gly Tyr Leu Cys Thr Phe Cys Leu Ile Ala Lys Pro Lys
625                 630                 635                 640

Gln Ile Tyr Cys Tyr Leu Gln Arg Ile Gly Ile Gly Leu Ser Pro Ala
                645                 650                 655

Met Ser Tyr Ser Ala Leu Val Thr Lys Thr Asn Arg Ile Ala Arg Ile
                660                 665                 670

Leu Ala Gly Ser Lys Lys Lys Ile Cys Thr Pro Lys Pro Arg Phe Met
            675                 680                 685

Ser Ala Cys Ala Gln Leu Val Ile Ala Phe Ile Leu Ile Cys Ile Gln
    690                 695                 700

Leu Gly Ile Ile Val Ala Leu Phe Ile Met Glu Pro Pro Asp Ile Met
705                 710                 715                 720
```

```
His Asp Tyr Pro Ser Ile Arg Glu Val Tyr Leu Ile Cys Asn Thr Thr
            725                 730                 735

Asn Leu Gly Val Val Thr Pro Leu Gly Asn Asn Gly Leu Leu Ile Leu
            740                 745                 750

Ser Cys Thr Phe Tyr Ala Phe Lys Thr Arg Asn Val Pro Ala Asn Phe
            755                 760                 765

Pro Glu Ala Lys Tyr Ile Ala Phe Thr Met Tyr Thr Thr Cys Ile Ile
    770                 775                 780

Trp Leu Ala Phe Val Pro Ile Tyr Phe Gly Ser Asn Tyr Lys Ile Ile
785                 790                 795                 800

Thr Met Cys Phe Ser Val Ser Leu Ser Ala Thr Val Ala Leu Gly Cys
                805                 810                 815

Met Phe Val Pro Thr Val Tyr Ile Ile Leu Ala Lys Pro Glu Arg Asn
                820                 825                 830

Val Arg Ser Ala Phe Thr Thr Ser Thr Val Val Arg Met His Val Gly
        835                 840                 845

Asp Gly Lys Ser Ser Ser Ala Ala Ser Arg Ser Ser Ser Leu Val Asn
        850                 855                 860

Leu Trp Lys Arg Arg Gly Ser Ser Gly Glu Thr Leu Arg
865                 870                 875
```

(2) INFORMATION FOR SEQ ID NO:13:

(i) SEQUENCE CHARACTERISTICS:
        (A) LENGTH: 343 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..343
        (D) OTHER INFORMATION: /note= "Partial sequence of MGLUR2
           - 3' untranslated sequence."

(xi) SEQUENCE DESCRIPTION: SEQ ID NO:13:

```
TGGAGACGCC ATACTGCCGC GCTGACACAG CTGCTCCTGG GCACCTAGTG CAGACCCACG      60

TCCAGGGCCA GGAGGAAGTT GGCTGGAGCA CTGCAATAAT TTATTACCCA GCCTATGTCT     120

GCCCCCCGAG TCACTTACCC ACCTCCTTAC CCCAGCTCTT CAGACTCAGA AGTCAGGAGC     180

CTTGGCCAGG AGCCTCTGCA GTGGCCACTA ACTGCCCTTG TAGCTGTGTT TCCTCCTGGC     240

CAGGCCCAGG GCTCAGAGAG GAGCAAGCCA GGGTTCACTC TGCCCTGGAC CCGGGTGGCT     300

GAGGACGGCA GGCCCCAGTC CTAACCAGCA AAGGTGCTTC CAG                       343
```

CATION-BASED BIOASSAY USING HUMAN METABOTROPIC GLUTAMATE RECEPTORS

RELATED APPLICATIONS

This application is a 371 of International application PCT/US94/06273, filed June 3, 1994, which is in turn a continuation-in-part application of U.S. Application Ser. No. 08/072,574, filed June 4, 1993, now U.S. Pat. No. 5,521,297, the entire contents of which are hereby incorporated by reference.

The present invention relates to nucleic acids and receptor proteins encoded thereby. Invention nucleic acids encode novel human metabotropic glutamate receptor subtypes. The invention also relates to methods for making such receptor subtypes and for using the receptor proteins in assays designed to identify and characterize compounds which affect the function of such receptors, e.g., agonists, antagonists, and allosteric modulators of human metabotropic glutamate receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are NMDA (N-methyl-D-aspartate) receptors and kainate/AMPA (α-amino-3-hydroxy-5-methyl-4-isoxazole propionate, formerly called the quisqualic acid or QUIS receptor), receptors. While the metabotropic receptors bind to some of the same ligands that bind to ionotropic glutamate receptors, the metabotropic receptors alter synaptic physiology via GTP-binding proteins and second messengers such as cyclic AMP, cyclic GMP, diacylglycerol, inositol 1,4,5-triphosphate and calcium [see, for example, Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of metabotropic glutamate receptors have been studied using animal tissues and cell lines as a source of receptors, as well as non-human recombinant receptors. The value of such studies for application to the development of human therapeutics has been limited by the availability of only non-human receptors. Moreover, it is only recently that the characteristics and structure of metabotropic glutamate receptors have been investigated at the molecular level. Such investigation has, however, only been carried out in non-human species. Because of the potential physiological and pathological significance of metabotropic glutamate receptors, it is imperative (particularly for drug screening assays) to have available human sequences (i.e., DNA, RNA, proteins) which encode representative members of the various glutamate receptor classes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding human metabotropic glutamate receptor protein subtypes and the proteins encoded thereby. In a particular embodiment the novel nucleic acids encode full-length mGluR1, mGluR2, mGluR3 and mGluR5 subtypes of human metabotropic glutamate receptors, or portions thereof. In addition to being useful for the production of metabotropic glutamate receptor subtype proteins, these nucleic acids are also useful as probes, thus enabling those skilled in the art, without undue experimentation, to identify and isolate nucleic acids encoding related receptor subtypes.

In addition to disclosing novel metabotropic glutamate receptor protein subtypes, the present invention also comprises methods for using such receptor subtypes to identify and characterize compounds which affect the function of such receptors, e.g., agonists, antagonists, and modulators of glutamate receptor function. The invention also comprises methods for determining whether unknown protein(s) are functional as metabotropic glutamate receptor subtypes.

DETAILED DESCRIPTION OF THE INVENTION

Figure 1:
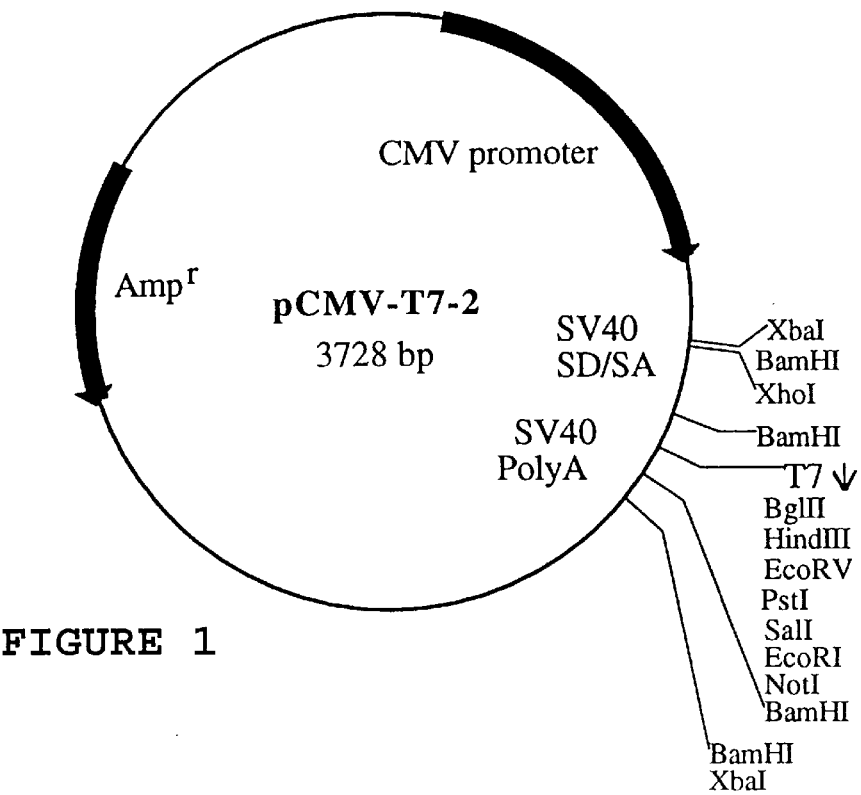
FIG. 1 presents a restriction map of CMV promoter-based vector pCMV-T7-2.
Figure 2:
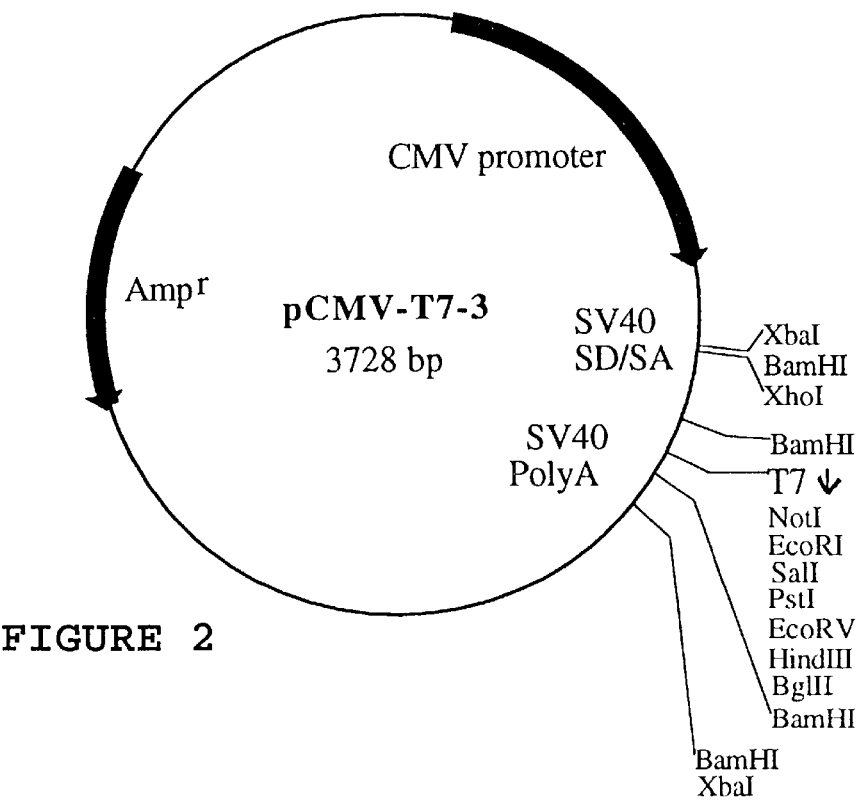
FIG. 2 presents a restriction map of CMV promoter-based vector pCMV-T7-3.

In accordance with the present invention, there are provided isolated nucleic acids encoding human metabotropic glutamate receptor subtypes. In one aspect of the present invention, nucleic acids encoding human metabotropic glutamate receptors of the mGluR1 subtype are provided. In another aspect, nucleic acids encoding at least a portion of metabotropic glutamate receptors of the mGluR2 subtype are provided. In yet another aspect, nucleic acids encoding metabotropic glutamate receptors of the mGluR3 subtype are provided. In a further aspect, nucleic acids encoding metabotropic glutamate receptors of the mGluR5 subtype are provided. In a still further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising metabotropic glutamate receptor subtype-selective portions of the above-described nucleic acids.

As employed herein, the phrase "human metabotropic glutamate receptor subtypes" refers to isolated and/or purified proteins which participate in the G-protein-coupled response of cells to glutamatergic ligands. Such receptor subtypes are individually encoded by distinct genes which do not encode other metabotropic glutamate receptor subtypes (i.e., each subtype is encoded by a unique gene). Such receptor subtypes are typically characterized by having seven putative transmembrane domains, preceded by a large putative extracellular amino-terminal domain and followed by a large putative intracellular carboxy-terminal domain. Metabotropic glutamate receptors share essentially no amino acid sequence homology with other G-protein-coupled receptors that are not metabotropic glutamate receptors.

Regarding the inter-relationship between each of the metabotropic glutamate receptor subtypes, the amino acid sequences of mGluR1 receptor subtypes are generally less than about 70% identical to the amino acid sequences of other human metabotropic glutamate receptor subtypes, with identities less than about 45% typically observed. The amino acid sequences of mGluR2 receptor subtypes are generally less than 60% identical to the amino acid sequences of other human metabotropic glutamate receptor subtypes, with identities of less than 45% typically observed. The amino acid sequences of mGluR3 receptor subtypes are generally less than 60% identical to the amino acid sequences of other human metabotropic glutamate receptor subtypes, with identities of less than 45% typically observed. The amino acid sequences of mGluR5 receptor subtypes are generally less than 70% identical to the amino acid sequences of other human metabotropic glutamate receptor subtypes, with identities of less than 45% typically observed.

Also included within the above definition are variants thereof encoded by mRNA generated by alternative splicing of a primary transcript, as well as fragments thereof which retain one or more of the above physiological and/or physical properties.

Use of the terms "isolated" or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of glutamatergic ligands (such as ACPD or ACPD-like ligands, QUIS, AP4, and the like) to said receptor protein(s) modifies the receptor interaction with G-proteins, which in turn affects the levels of intracellular second messengers, leading to a variety of physiological effects. Stated another way, "functional" means that a response is generated as a consequence of agonist activation of receptor protein(s).

As used herein, a splice variant refers to variant metabotropic glutamate receptor subtype-encoding nucleic acid(s) produced by differential processing of primary transcript(s) of genomic DNA, resulting in the production of more than one type of mRNA. cDNA derived from differentially processed primary transcript will encode metabotropic glutamate receptor subtypes that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are nucleic acids that encode metabotropic glutamate receptor subtypes as defined above, but that by virtue of degeneracy of the genetic code do not necessarily hybridize to the disclosed nucleic acids under specified hybridization conditions. Such subtypes also form functional receptors, as assessed by methods described herein or known to those of skill in the art. Typically, unless a metabotropic glutamate receptor subtype is encoded by RNA that arises from alternative splicing (i.e., a splice variant), metabotropic glutamate receptor subtype-encoding nucleic acids and the metabotropic glutamate receptor protein encoded thereby share substantial sequence homology with at least one of the metabotropic glutamate receptor subtype nucleic acids (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional metabotropic glutamate receptor subtype.

Exemplary DNA sequences encoding human mGluR1 subtypes are represented by nucleotides which encode substantially the same amino acid sequence as set forth in Sequence ID No. 2. Presently preferred sequences encode the amino acid sequence set forth in Sequence ID No. 2.

Exemplary DNA can alternatively be characterized as those nucleotide sequences which encode an human mGluR1 subtype and hybridize under high-stringency conditions to substantially the entire sequence of Sequence ID No. 1, or substantial portions thereof (i.e., typically at least 25–30 contiguous nucleotides thereof).

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C. - 16.6(\log_{10}[Na^+]) + 0.41(\% \ G+C) - 600/l,$$

where l is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refer to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.;

(2) MODERATE STRINGENCY conditions, with respect to fragment hybridization, refer to conditions equivalent to hybridization in 50% formamide, 5× Denhart's solution, 5× SSPE, 0.2% SDS at 42° C., followed by washing in 0.2× SSPE, 0.2% SDS, at 65° C.; and (3) LOW STRINGENCY conditions, with respect to fragment hybridization, refer to conditions equivalent to hybridization in 10% formamide, 5× Denhart's solution, 6× SSPE, 0.2% SDS at 42° C., followed by washing in 1× SSPE, 0.2% SDS, at 50° C.

(4) HIGH STRINGENCY conditions, with respect to oligonucleotide (i.e., synthetic DNA≦about 30 nucleotides in length) hybridization, refer to conditions equivalent to hybridization in 10% formamide, 5× Denhart's solution, 6× SSPE, 0.2% SDS at 42° C. followed by washing in 1× SSPE, and 0.2% SDS at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50× stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences encoding human mGluR1 subtypes are those which have substantially the same nucleotide sequence as the coding sequences in Sequence ID No. 1; with polynucleic acid having the same sequence as the coding sequence in Sequence ID No. 1 being most preferred.

As used herein, the phrase "substantial sequence homology" refers to nucleotide sequences which share at least about 90% identity, and amino acid sequences which typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

Exemplary DNA sequences encoding a portion of an human mGluR2 receptor subtype are represented by nucleotides which encode substantially the same amino acid sequence as set forth in Sequence ID No. 4 (optionally including some or all of the 343 nucleotides of 3' untranslated sequence set forth in sequence ID No. 13), or substantially the same amino acid sequence as that encoded by the human mGluR2-encoding portion of clone METAB40, deposited with the ATCC on May 4, 1993, under accession number 75465.

The deposited clone has been deposited on May 4, 1993, at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Presently preferred polynucleic acid sequences that encode a portion of an human mGluR2 receptor subtype are those that encode the same amino acid sequence as Sequence ID No. 4, or the same amino acid sequence as that encoded by the human mGluR2-encoding portion of clone METAB40, deposited with the ATCC on May 4, 1993, under accession number 75465.

Exemplary DNAs can alternatively be characterized as those nucleotide sequences which encode a human mGluR2 receptor subtype and hybridize under high-stringency conditions to Sequence ID No. 3, or substantial portions thereof (i.e., typically at least 25–30 contiguous nucleotides thereof), or the human mGluR2-encoding portion of clone METAB40 (ATCC accession No. 75465), or substantial portions thereof. Especially preferred sequence encoding a portion of an human mGluR2 receptor subtype is represented by polynucleic acid which has the same nucleotide sequence as the coding sequence set forth in Sequence ID No. 3, or the nucleotide sequence of the coding sequence in the human mGluR2-encoding portion of clone METAB40.

Exemplary DNA sequences encoding human mGluR3 receptor subtypes are represented by nucleotides which encode substantially the same amino acid sequence as set forth in Sequence ID No. 6. Presently preferred polynucleic acid sequences are those that encode the same sequence as Sequence ID No. 6.

Exemplary DNAs can alternatively be characterized as those nucleotide sequences which encode a human mGluR3 receptor subtype and hybridize under high-stringency conditions to substantially the entire sequence of Sequence ID No. 5, or substantial portions thereof (i.e., typically at least 25–30 contiguous nucleotides thereof). Especially preferred sequences encoding human mGluR3 subtypes are those which have substantially the same nucleotide sequence as the coding sequences in Sequence ID No. 5, with the polynucleic acid having the same nucleotide sequence as the coding sequence set forth in Sequence ID No. 5 being the presently most preferred.

Exemplary DNA sequences encoding human mGluR5 receptor subtypes or portions thereof are represented by nucleotides which encode substantially the same amino acid sequence as set forth in Sequence ID Nos. 8, 10 or 12. Presently preferred polynucleic acid sequences are those that encode the same sequence as Sequence ID Nos. 8, 10 or 12.

Exemplary DNAs can alternatively be characterized as those nucleotide sequences which encode a human mGluR5 receptor subtype and hybridize under high stringency conditions to substantially the entire sequence of Sequence ID Nos. 7, 9 or 11, or substantial portions thereof (i.e., typically at least 25–30 contiguous nucleotides thereof). Especially preferred sequences encoding human mGluR5 subtypes are those which have substantially the same nucleotide sequence as the coding sequences set forth in Sequence ID Nos. 7, 9 or 11; with polynucleic acids having the same sequence as the coding sequence set forth in Sequence ID Nos. 7, 9 or 11 being the presently most preferred.

DNA encoding human metabotropic glutamate receptor subtypes may be isolated by screening suitable human cDNA or human genomic libraries under suitable hybridization conditions with DNA disclosed herein (including nucleotides derived from any of SEQ ID Nos. 1, 3, 5, 7, 9 or 11). Suitable libraries can be prepared from neural tissue samples, e.g., hippocampus and cerebellum tissue, cell lines, and the like. For example, the library can be screened with a portion of DNA including substantially the entire receptor subtype-encoding sequence thereof, or the library may be screened with a suitable oligonucleotide probe based on a portion of the DNA.

As used herein, a probe is single-stranded DNA or RNA that has a sequence of nucleotides that includes at least about 25–30 contiguous bases that are the same as (or the complement of) any 25 or more contiguous bases set forth in any of SEQ ID Nos. 1, 3, 5, 7, 9 or 11. Preferred regions from which to construct probes include 5' and/or 3' coding sequences, sequences predicted to encode transmembrane domains, sequences predicted to encode cytoplasmic loops, signal sequences, ligand binding sites, and the like.

Either the full-length cDNA clones, fragments thereof, or oligonucleotides based on portions of the cDNA clones can be used as probes, preferably labeled with suitable label means for ready detection. When fragments are used as probes, DNA sequences for such probes will preferably be derived from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol.* Vol. 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors.

Similarly, patients having a family history of disease states related to glutamate receptor dysfunction can be screened to determine if they are also predisposed to such disease states.

In accordance with another embodiment of the present invention, there is provided a method for identifying DNA encoding human metabotropic glutamate receptor protein subtypes, said method comprising:

contacting human DNA with a nucleic acid probe as described above, wherein said contacting is carried out under low- to moderate-stringency hybridization conditions when the probe used is a polynucleic acid fragment, or under high-stringency hybridization conditions when the probe used is an oligonucleotide, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete metabotropic glutamate receptor subtype (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and deduced amino acid sequences provided herein.

Complementary DNA clones encoding various human metabotropic glutamate receptor subtypes (e.g., mGluR1, mGluR2, mGluR3, mGluR5) have been isolated. Each subtype appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate DNA encoding splice variants of human metabotropic glutamate receptor subtypes. This is accomplished by employing oligonucleotides based on DNA sequences surrounding known or predicted divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human metabotropic glutamate receptor subtypes.

It has been found that not all metabotropic glutamate receptor subtypes (and variants thereof) are expressed in all neural tissues or in all portions of the brain. Thus, in order to isolate cDNA encoding a particular subtype (or splice variants thereof), it is preferable to screen libraries prepared from different neuronal or neural tissues or cells. Preferred libraries for obtaining DNA encoding each subtype include: cerebellum to isolate human mGluR1-encoding DNAS; hippocampus to isolate human mGluR2-encoding DNAS; hippocampus and cerebellum to isolate mGluR3-encoding DNAs; hippocampus and cerebellum to isolate mGluR5-encoding DNAs; and the like.

Once DNA encoding a particular receptor subtype has been isolated, ribonuclease (RNase) protection assays can be employed to determine which tissues express MRNA encoding such subtype (or splice variant thereof). These assays provide a sensitive means for detecting and quantitating an RNA species in a complex mixture of total cellular RNA. The subtype DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. in situ hybridization techniques can also be used t o determine which tissues express mRNAs encoding particular metabotropic glutamate receptor subtypes. Thus, labeled subtype DNAs can be hybridized to different brain region slices to visualize subtype mRNA expression.

It appears that the distribution of expression of some human metabotropic glutamate receptor subtypes differs from the distribution of such receptors in rat. For example, even though RNA encoding the rat mGluR5 subtype is abundant in rat hippocampus, but is not abundant in rat cerebellum [see, e.g., Abe et al., J. Biol. Chem. 267: 13361–13368 (1992)], human mGluR5-encoding CDNAs were successfully obtained from human cerebellum cDNA libraries. Thus, the distribution of some metabotropic glutamate receptor subtypes in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

An expression vector includes vectors capable of expressing DNAs that are operatively linked with regulatory sequences, such as promoter regions, that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention metabotropic glutamate receptor subtypes in eukaryotic host cells, particularly mammalian cells, include cytomegalovirus (CMV) promoter-containing vectors such as pCMV-T7-2 and pCMV-T7-3 (see FIG. 1), pcDNA1, and the like, as well as SV40 promoter-containing vectors and MMTV LTR promoter-containing vectors, such as pMMTVT7(+) or pMMTVT7(−) (modified versions of pMAMneo (Clontech, Palo Alto, Calif.), prepared as described herein), and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' and/or 3' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. Likewise, alternative codons, encoding the same amino acid, can be substituted for coding sequences of the metabotropic glutamate receptor subunits in order to enhance transcription (e.g., the codon preference of the host cells can be adopted, the presence of G-C rich domains can be reduced, and the like). Furthermore, for potentially enhanced expression of metabotropic glutamate receptor subunits in amphibian oocytes, the subunit coding sequence can optionally be incorporated into an expression construct wherein the 5'- and 3'-ends of the coding sequence are contiguous with Xenopus β-globin gene 5' and 3' untranslated sequences, respectively. For example, metabotropic glutamate receptor subunit coding sequences can be incorporated into vector pSP64T (see Krieg and Melton (1984) in Nucleic Acids Research 12:7057–7070), a modified form of pSP64 (available from Promega, Madison, Wis.). The coding sequence is inserted between the 5' end of the β-globin gene and the 3' untranslated sequences located downstream of the SP6 promoter. In vitro transcripts can then be generated from the resulting vector. The desirability of (or need for) such modifications may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred base vectors which contain regulatory elements that can be linked to human metabotropic receptor-encoding DNAs for transfection of mammalian cells are cytomegalovirus (CMV) promoter-based vectors such as pCMV-T7-2 and pCMV-T7-3 (described herein) or pcDNA1 (Invitrogen, San Diego, Calif.), MMTV promoter-based vectors such as pMMTVT7(+) or pMMTVT7(−) (as described herein), and SV40 promoter-based vectors such as PSVP (Clontech, Palo Alto, Calif.).

Full-length DNAs encoding human metabotropic glutamate receptor subtypes have been inserted into vectors pMMTVT7(+), pMMTVT7(−) pCMV-T7-2 or pCMV-T7-3. pCMV-T7-2 (and pCMV-T7-3) are pUC19-based mammalian cell expression vectors containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of metabotropic glutamate receptor subtype DNA between the CMV promoter and SV40 polyadenylation signal should provide for constitutive expression of the foreign DNA in a mammalian host cell transfected with the construct.

Vectors pMMTVT7(+) and pMMTVT7(−) were prepared by modifying vector pMAMneo (Clontech, Palo Alto, Calif.). pMAMneo is a mammalian expression vector that contains the Rous Sarcoma Virus (RSV) long terminal repeat (LTR) enhancer, linked to the dexamethasone-inducible mouse mammary tumor virus (MMTV)-LTR promoter, followed by SV40 splicing and polyadenylation sites. pMAMneo also contains the *E. coli* neo gene for selection of transformants, as well as the β-lactamase gene (encoding a protein which imparts ampicillin-resistance) for propagation in *E. coli*.

Vector PMMTVT7(+) can be generated by modification of pMAMneo to remove the neo gene and insert the multiple cloning site and T7 and T3 promoters from pBluescript (Stratagene, La Jolla, Calif.). Thus, pMMTVT7(+) contains the RSV-LTR enhancer linked to the MMTV-LTR promoter, a T7 bacteriophage RNA polymerase promoter positioned downstream of the MMTV-LTR promoter, a polylinker positioned downstream of the T7 promoter, a T3 bacteriophage RNA polymerase promoter positioned downstream of the T7 promoter, and SV40 splicing and polyadenylation sites positioned downstream of the T3 promoter. The β-lactamase gene (encoding a protein which imparts ampicillin-resistance) from pMAMneo is retained in pMMTVT7(+), although it is incorporated in the reverse orientation relative to the orientation in pMAMneo.

Vector pMMTVT7(−) is identical to pMMTVT7(+) except that the positions of the T7 and T3 promoters are switched, i.e., the T3 promoter in pMMTVT7(−) is located where the T7 promoter is located in pMMTVT7(+), and the T7 promoter in pMMTVT7(−) is located where the T3 promoter is located in pMMTVT7(+). Therefore, vectors pMMTVT7(+) and pMMTVT7(−) contain all of the regulatory elements required for expression of heterologous DNA in a mammalian host cell, wherein the heterologous DNA has been incorporated into the vectors at the polylinker. In addition, because the T7 and T3 promoters are located on either side of the polylinker, these plasmids can be used for synthesis of in vitro transcripts of heterologous DNA that has been subcloned into the vectors at the polylinker.

For inducible expression of human metabotropic glutamate receptor subtype-encoding DNA in a mammalian cell, the DNA can be inserted into a plasmid such as pMMTVT7(+) or pMMTVT7(−). These plasmids contain the mouse mammary tumor virus (MMTV) LTR promoter for steroid-inducible expression of operatively associated foreign DNA. If the host cell does not express endogenous glucocorticoid receptors required for uptake of glucocorticoids (i.e., inducers of the MMTV LTR promoter) into the cell, it is necessary to additionally transfect the cell with DNA encoding the glucocorticoid receptor (ATCC accession no. 67200). For synthesis of in vitro transcripts, full-length human DNA clones encoding human mGluR1, mGluR3 and mGluR5 can also be subcloned into pIBI24 (International Biotechnologies, Inc., New Haven, Conn.), pCMV-T7-2 or pCMV-T7-3 (see FIG. 1), pMMTVT7(+), pMMTVT7(−), pBluescript (Stratagene, La Jolla, Calif.), pGEM7Z (Promega, Madison, Wis.), or the like.

In accordance with another embodiment of the present invention, there are provided cells containing the above-described polynucleic acids (i.e., DNA or mRNA). Such host cells as bacterial, yeast and mammalian cells can be used for replicating DNA and producing metabotropic glutamate receptor subtype(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/05625 and PCT/US92/11090, and in co-pending U.S. application Ser. Nos. 07/563,751 and 07/812,254. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subtype(s) encoded by the DNA is (are) expressed. Preferred cells include mammalian cells (e.g., HEK293, CHO and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha*, and the like), mammalian expression systems, including commercially available systems and other such systems known to those of skill in the art which express G-proteins (either endogenously or recombinantly), for expression of DNA encoding the human metabotropic glutamate receptor subtypes provided herein are presently preferred. Xenopus oocytes are preferred for expression of in vitro mRNA transcripts of DNA encoding those human metabotropic receptor subtypes that are coupled to the PI hydrolysis/$Ca^{++}$ signalling pathways. An endogenous inositol triphosphate second messenger-mediated pathway in oocytes permits functional expression of human metabotropic receptors in these cells. Oocytes expressing recombinant human metabotropic receptors respond to agonists via the oocyte G-protein-coupled $IP_3$ generation pathway, which stimulates release of $Ca^{++}$ from internal stores, and reportedly activates a chloride channel that can be detected as a delayed oscillatory current by voltage-clamp recording.

Host cells for functional recombinant expression of human metabotropic receptors preferably express endogenous or recombinant guanine nucleotide-binding proteins (i.e., G-proteins). G-proteins are a highly conserved family of membrane-associated proteins composed of α, β and γ subunits. The a subunit, which binds GDP and GTP, differs in different G-proteins. The attached pair of β and γ subunits may or may not be unique; different α chains may be linked to an identical βγ pair or to different pairs [Linder and Gilman, Sci. Am. 267:56–65 (1992)]. More than 30 different cDNAs encoding G protein α subunits have been cloned [Simon et al., Science 252:802 (1991)]. Four different β polypeptide sequences are known [Simon et al., Science 252:802 (1991)]. Three of five identified γ cDNAs have been cloned [Hurley et al., PNAS U.S.A. 81:6948 (1984); Gautam et al., Science 244:971 (1989); and Gautam et al., PNAS U.S.A. 87:7973 (1990)]. The sequences of a fourth γ cDNA [Kleuss et al., Science 259:832 (1993)] and a fifth γ cDNA [Fisher and Aronson, Mol. Cell. Bio. 12:1585 (1992)] have been established, and additional γ subtypes may exist [Tamir et al., Biochemistry 30:3929 (1991)]. G-proteins switch between active and inactive states by guanine nucleotide exchange and GTP hydrolysis. Inactive G protein is stimulated by a ligand-activated receptor to exchange GDP for GTP. In the active form, the a subunit, bound to GTP, dissociates from the βγ complex, and the subunits then interact specifically with cellular effector molecules to evoke a cellular response. Because different G-proteins can interact with different effector systems (e.g., phospholipase C, adenyl cyclase systems) and different receptors, it is useful to investigate different host cells for expression of different recombinant human metabotropic receptor subtypes. Alternatively, host cells can be transfected with G-protein subunit-encoding DNAs for heterologous expression of differing G proteins.

In preferred embodiments, human metabotropic glutamate receptor subtype-encoding DNA is ligated into a vector, and introduced into suitable host cells to produce transformed cell lines that express a specific human metabotropic glutamate receptor subtype, or specific combinations of subtypes. The resulting cell lines can then be produced in quantity for reproducible quantitative analysis of the effects of known or potential drugs on receptor function. In other embodiments, mRNA may be produced by in vitro transcription of DNA encoding each subtype. This mRNA, either from a single subtype clone or from a combination of clones, can then be injected into Xenopus oocytes where the mRNA directs the synthesis of functional human metabotropic glutamate receptor subtypes. Alternatively, the subtype-encoding DNA can be directly injected into oocytes for expression of functional human metabotropic glutamate receptor subtypes. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected and which cells express (endogenously or recombinantly) G-proteins. Preferred cells are those that express little, if any, endogenous metabotropic receptors and can be transiently or stably transfected and also express invention DNA and RNA. Presently most preferred cells are those that can form recombinant or heterologous human metabotropic glutamate receptors comprising one or more subtypes encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., Xenopus laevis oöcytes), yeast cells (e.g., Saccharomyces cerevisiae, Pichia pastoris), and the like. Exemplary cells for expressing injected RNA transcripts include Xenopus laevis oöcytes. Cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); CHO cells (which are available from ATCC under accession #CRL9618, CCL61 or CRL9096); DG44 cells (dhfr⁻ CHO cells; see, e.g., Urlaub et al. (1986) Cell. Molec. Genet. 12: 555); and BHK cells (see Waechter and Baserga, PNAS U.S.A. 79:1106–1110 (1982); also available from ATCC under accession #CRL10314). Presently preferred cells include CHO cells and HEK293 cells, particularly HEK293 cells that can be frozen in liquid nitrogen and then thawed and regrown (for example, those described in U.S. Pat. No. 5,024,939 to Gorman (see, also, Stillman et al. (1985) Mol. Cell. Biol. 5:2051–2060)), DG44, Ltk⁻ cells, and the like. Those of skill in the art recognize that comparison experiments should also be carried out with whatever host cells are employed to determine background levels of glutamate production induced by the ligand employed, as well as background levels of glutamate present in the host cell in the absence of ligand.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the E. coli β-galactosidase gene) to monitor transfection efficiency. Selectable marker genes are typically not included in the transient transfections because the transfectants are typically not grown under selective conditions, and are usually analyzed within a few days after transfection.

To produce such stably or transiently transfected cells, the cells should be transfected with a sufficient concentration of subtype-encoding nucleic acids to form human metabotropic glutamate receptors indicative of the human subtypes encoded by the heterologous DNA. The precise amounts of DNA encoding the subtypes may be empirically determined and optimized for a particular subtype, cells and assay conditions. Recombinant cells that express metabotropic glutamate receptors containing subtypes encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human metabotropic glutamate receptor subtypes may be purified using protein purification methods known to those of skill in the art. For example, antibodies or other ligands that specifically bind to one or more subtypes may be used for affinity purification of a given metabotropic glutamate receptor subtype.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human metabotropic glutamate receptor subtype, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Those of skill in the art can readily identify a variety of assays which can be used to detect the expression of functional mGluRs. Examples include PI turnover assays [see, e.g., Nakajima et al., J. Biol. Chem. 267:2437–2442 (1992) and Example 3.C.2], cAMP assays [see, e.g., Nakajima et al., supra and Example 3.C.4.], calcium ion flux assays [see, e.g., Ito et al., J. Neurochem. 56:531–540 (1991) and Example 3.C.1], cGMP assays [see, e.g., Steiner et al., J. Biol. Chem 247:1106–1113 (1972)], arachidonic acid release assays [see, e.g., Felder et al., J. Biol. Chem. 264:20356–20362 (1989)], and the like. In addition, cation-based assays (as described herein) can be employed for monitoring receptor-induced changes in intracellular cyclic nucleotide levels. Such assays employ host cells expressing cyclic nucleotide-gated ion channels. These channels, which occur in, for example, rod photoreceptor cells, olfactory cells and bovine kidney cells (see, for example, Kaupp et al., in *Nature* 342:762–766 (1989), Dhallen et al., in *Nature* 347:184–187 (1990) and Biel et al., in *Proc. Natl. Acad. Sci. USA* 91:3505–3509 (1994), are permeable to cations upon activation by binding of cAMP or cGMP. Thus, in the invention assay, host cells expressing endogenous or recombinant cyclic nucleotide-gated channels are transfected (or injected) with nucleic acids encoding receptors suspected of influencing cyclic nucleotide levels (e.g., metabotropic glutamate receptor-encoding DNA), and then monitored for changes in the amount of cyclic nucleotide activation of the channels. Measuring changes in cyclic nucleotide activation of channels allows one to indirectly identify as functional those receptors that cause a change in cAMP or cGMP levels when activated. The change in the amount of activation of the cyclic nucleotide-gated channels can be determined by measuring ion flux through the channel either by electrophysiological measurement of currents or by measuring a change in intracellular cation levels (e.g., by fluorescence measurement of intracellular calcium).

In assays of cells expressing receptor species that cause a decrease in cyclic nucleotides upon activation (e.g., some metabotropic glutamate receptors), it may be preferable to expose the cells to agents that increase intracellular levels of cyclic nucleotides (e.g., forskolin and IBMX) prior to adding a receptor-activating compound to the cells in the assay.

Host cells suitable for use in the above-described assay include any host cells suitable for expression of the receptor being studied (e.g., L cells, HEK293 cells, CHO, cells or Xenopus oocytes for assays of metabotropic glutamate receptors). The cells can be sequentially transfected (or injected) with nucleic acids encoding a cyclic nucleotide-gated channel and receptor-encoding nucleic acids, or the cells can be co-transfected with the two nucleic acids. Transient or stable transfection, as described in Examples 3A and 3B, can be carried out.

Cells transfected (or injected) with cyclic nucleotide-gated channel nucleic acid are incubated (typically for ~24–48 hours) before testing for function. The activity of the channels can be assessed using inside-out membrane patches pulled from the transfected cells (so that the concentration of cAMP reaching the cytoplasmic face can be controlled). The transfectants can also be analyzed by single-cell video imaging of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay can be conducted essentially as described in Example 3.C.4.b.

The DNA, mRNA, vectors, receptor subtypes, and cells provided herein permit production of selected metabotropic glutamate receptor subtypes, as well as antibodies to said receptor subtypes. This provides a means to prepare synthetic or recombinant receptors and receptor subtypes that are substantially free of contamination from many other receptor proteins whose presence can interfere with analysis of a single metabotropic glutamate receptor subtype. The availability of desired receptor subtypes makes it possible to observe the effect of a drug substance on a particular receptor subtype or combination of metabotropic glutamate receptor subtypes, and to thereby perform initial in vitro screening of the drug substance in a test system that is specific for humans and specific for a human metabotropic glutamate receptor subtype or combination of metabotropic glutamate receptor subtypes. The availability of specific antibodies makes it possible to identify the subtype combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subtypes or specific combinations of various receptor subtypes with a variety of potential agonists or antagonists provides additional information with respect to the function and activity of the individual subtypes and should lead to the identification and design of compounds that are capable of very specific interaction with one or more receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human metabotropic glutamate receptor subtypes enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if endogenous channels are in turn activated. If currents are detected, the fragments are functional as glutamate receptors.

In accordance with still another embodiment of the present invention, there is provided a method for identifying compounds which bind to human metabotropic glutamate receptor subtype(s), said method comprising employing receptor proteins of the invention in a competitive binding assay. Such an assay can accommodate the rapid screening of a large number of compounds to determine which compounds, if any, are capable of displacing specifically bound [$^3$H] glutamate, i.e., binding to metabotropic glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor subtype(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human metabotropic glutamate receptor subtypes of the invention, said bioassay comprising:

(a) exposing cells containing DNA encoding human metabotropic glutamate receptor subtype(s), wherein said cells express functional metabotropic glutamate receptors, to at least one compound whose ability to modulate the activity of said receptors is sought to be determined; and thereafter (b) monitoring said cells for changes in second messenger activity.

The above-described bioassay enables the identification of agonists, antagonists and allosteric modulators of human metabotropic glutamate receptors. According to this method, recombinant metabotropic glutamate receptors are contacted with an "unknown" or test substance (in the further presence of a known metabotropic glutamate agonist, when antagonist activity is being tested), the second messenger activity of the known glutamate receptor is monitored subsequent to the contact with the "unknown" or test substance, and those substances which increase or decrease the second messenger response of the known glutamate receptor(s) are identified as functional ligands (i.e., modulators, agonists or antagonists) for human metabotropic glutamate receptors. Second messenger activities which can be monitored include changes in the concentration of intracellular calcium ions, IP$_3$, cAMP levels, or monitoring of arachidonic acid release or activation or inhibition of ion current (when the host cell is an oocyte).

In accordance with a particular embodiment of the present invention, recombinant human metabotropic glutamate receptor-expressing mammalian cells or oocytes can be contacted with a test compound, and the modulating effect(s) thereof can then be evaluated by comparing the metabotropic glutamate receptor-mediated response in the presence and absence of test compound, or by comparing the metabotropic glutamate receptor-mediated response of test cells, or control cells (i.e., cells that do not express metabotropic glutamate receptors), to the presence of the compound.

As used herein, a compound or signal that "modulates the activity of a metabotropic glutamate receptor subtype" refers to a compound or signal that alters the activity of metabotropic glutamate receptors so that activity of the metabotropic glutamate receptor is different in the presence of the compound or signal than in the absence of the compound or signal. In particular, such compounds or signals include agonists and antagonists. The term agonist refers to a substance or signal, such as glutamate or ACPD, that activates receptor function; and the term antagonist refers to a substance that blocks agonist-induced receptor activation. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human metabotropic glutamate receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express the recombinant human metabotropic glutamate receptor subtype(s) expressed in the transfected cells. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the second messenger activity of human metabotropic glutamate receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subtype composition, structure of functional domains, purification of receptors, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the metabotropic glutamate receptor subtypes for use as immunogen (as either a synthetic peptide or a recombinantly produced bacterial fusion protein) include antigenicity, accessibility (i.e., extracellular and cytoplasmic domains), uniqueness to the particular subtype, etc.

The availability of subtype-specific antibodies makes possible the application of the technique of immunohistochemistry to monitor the distribution and expression density of various subtypes (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

In accordance with a still further embodiment of the present invention, there is provided a cation-based bioassay for monitoring receptor-induced changes in intracellular cyclic nucleotide levels, said bioassay comprising:

introducing nucleic acids encoding receptors suspected of influencing intracellular cyclic nucleotide levels into host cells expressing endogenous or recombinant cyclic nucleotide-gated channels, and monitoring changes in the amount of cyclic nucleotide activation of said cyclic nucleotide-gated channels in the presence and absence of ligand for said receptor suspected of influencing intracellular cyclic nucleotide levels.

The invention will now be described in greater detail by reference to the following non-limiting examples.

EXAMPLE 1

Isolation of DNA Encoding Human Metabotropic Glutamate Receptors

A. mGluR5 Receptor cDNA cDNA Library Screening

RNA isolated from human hippocampus tissue was used as a template for the synthesis of oligo dt-primed, single-stranded cDNA according to standard procedures [see, for example, Gubler and Hoffman (1983) Gene 25:263–269]. The single-stranded cDNA was converted to double-stranded cDNA, and EcoRI/SnaBI/XhoI adaptors were added to the ends of the cDNAs. The cDNAs were separated by size using agarose gel electrophoresis, and those that were >2.5 kb were ligated into EcoRI-digested λgt10 bacteriophage vectors. The resulting primary human hippocampus cDNA library (~2×10$^5$ recombinants) was screened for hybridization to a fragment of the DNA encoding the rat mGluR1 receptor (nucleotides 1 to 1723 plus 5' untranslated sequence; see Masu et al. (1991) Nature 349:760–765). Hybridization was performed in 5× SSPE, 5× Denhart's solution, 50% formamide, 0.2% SDS, 200 µg/ml denatured, sonicated herring sperm DNA at 42° C. and washes were performed in 1.0× SSPE, 0.2% SDS at 65° C. One hybridizing plaque, METAB1, was identified which contains a 3273 bp insert.

To obtain additional human mGluR5-encoding clones, METAB1 was radiolabeled and used to screen two human cerebellum cDNA libraries prepared as follows. cDNA was synthesized using random primers to prime first-strand cDNA synthesis from RNA isolated from human cerebellum tissue. The cDNAs were pooled based on length and two libraries were generated: one with inserts greater than 2.8 kb in length (i.e., a large-insert library) and one with inserts 1–2.8 kb in length (i.e., a medium-insert library). The libraries (1×10$^6$ recombinants in each) were screened for hybridization to the METAB1 probe using the same hybridization conditions as used for screening the hippocampus library for hybridization to the rat mGluR1 DNA fragment. Washes were performed in 1× SSPE, 0.2% SDS at 55° C. One hybridizing plaque, METAB2, was identified in the large-insert library, whereas four hybridizing plaques, METAB3-METAB6, were identified in the medium-insert library.

In another round of screening for human mGluR5-encoding DNAs, a randomly primed human hippocampus cDNA library (2×10$^6$ recombinants) containing inserts ranging in size from 1–2 kb and the medium-insert cerebellum cDNA library were screened for hybridization to radiolabeled METAB5 using the same conditions as those used in screening the large- and medium-insert cerebellum libraries with METAB1. Three hybridizing plaques (METAB10–METAB12) were identified in the hippocampus library and five additional hybridizing plaques (METAB13–METAB17) were identified in another primary screening of the cerebellum library. Selected plaques were purified.

Characterization of Isolated Clones

Characterization of the inserts of the purified plaques by restriction enzyme mapping and DNA sequence analysis revealed that at least three apparent splice variants of the human mGluR5 transcript were represented by the isolated clones. Analysis of METAB1 indicated that it contains a translation initiation codon but no translation termination codon. The deduced amino acid sequence is ~70% identical to the rat mGluR1 deduced amino acid sequence, but >90% identical to the rat mGluR5 deduced amino acid sequence [Abe et al. (1992) J. Biol. Chem. 267:13361–13368].

DNA sequence analysis of METAB5 showed that it overlaps the 3' end of METAB1 at the 5' end and continues for an additional 343 nucleotides in the 3' direction. Comparison of the overlapping regions of METAB1 and METAB5 revealed that METAB1 contains 96 nucleotides that are not present in METAB5 (i.e., METAB1 contains a 96-nucleotide insertion relative to METAB5). METAB5 also does not contain a translation termination codon. The insert of METAB12 overlaps the 3' end of METAB5 at the 5' end, however, and extends farther in the 3' direction to include a translation termination codon.

DNA sequence analysis of METAB2 showed that the first 869 nucleotides at the 5' end overlap, and are identical to a portion of the 3' end of METAB1; however, the sequences of METAB1 and METAB2 diverge at the beginning of the 96-nucleotide insertion of METAB1. METAB2 extends approximately 2700 nucleotides in the 3' direction and contains a putative translation termination codon 4 nucleotides 3' of the point of divergence with METAB1.

Partial DNA sequence analysis of METAB14 indicated that it encodes a portion of another human metabotropic receptor, mGluR1 (see Example 1.B.).

Preparation of Full-Length mGluR5 cDNA Constructs

Full-length constructs representing three putative splice variants of the human mGluR5 transcript, designated mGluR5a, mGluR5b and mGluR5c, can be generated and incorporated into expression vectors for use in preparing in vitro transcripts of the cDNAs and/or expression of the cDNAs in mammalian cells. The base expression vector typically used is pCMV-T7-3 or pCMV-T7-2 (see FIG. 1). Plasmid pCMV-T7-3 is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. pCMV-T7-3 and pCMV-T7-2 differ only in the orientation of the restriction sites in the polylinker.

To prepare a full-length mGluR5a construct (see Sequence ID No. 7), portions of clones METAB1, METAB5, and METAB12 were ligated together. Initially, the inserts of METAB1, METAB5 and METAB12 were separately transferred from λgt10 as EcoRI fragments into EcoRI-digested pGEM-7Zf (Promega, Madison, Wis.) for ease of manipulation. The pGEM-7Zf vector containing the METAB1 insert was digested with ScaI/NheI to release a 3.8 kb fragment containing the 5' half of the ampicillin resistance gene and a 5' portion of the METAB1 insert (nucleotides 1–2724 of Sequence ID No. 7). The pGEM-7Zf vector containing the insert of METAB5 was digested with ScaI/NheI to release a 2.6 kb fragment containing the 3' half of the ampicillin resistance gene and a 3' portion of METAB5 (nucleotides 2725–3469 of Sequence ID No. 7), and this fragment was ligated with the 3.8 kb fragment from the pGEM-7Zf vector containing METAB1 to create pGEM-METAB1+5. pGEM-METAB1+5 was digested with ScaI/NotI to release a 4.4 kb fragment containing the 5' half of the ampicillin resistance gene and nucleotides 1–3316 of Sequence ID No. 7. This 4.4 kb fragment was then ligated with a 2.6 kb fragment obtained by ScaI/NotI (partial) digestion of the pGEM-7Zf vector containing the METAB12 insert [the 2.6 kb fragment contains the 3' half of the ampicillin resistance gene and a 3' portion of METAB12 (nucleotides 3317–4085 of Sequence ID No. 7)]. The resulting vector contained the complete mGluR5a coding sequence in pGEM-7Zf. The full-length mGluR5a cDNA was isolated from the vector as an AatII (blunt-ended)-HindIII fragment and subcloned into NotI (blunt-ended)/HindIII-digested pCMV-T7-3 to generate construct mGluR5a1.

In summary, construct mGluR5a1 contains 369 bp of 5' untranslated sequence from METAB1 (nucleotides 1–369 of Sequence ID No. 7) and a complete coding sequence (nucleotides 370–3912 of Sequence ID No. 7) for the mGluR5a variant of the mGluR5 receptor, as well as 173 bp of 3' untranslated sequence (nucleotides 3913–4085 of Sequence ID No. 7). The mGluR5a-encoding sequence is operatively linked to the regulatory elements in pCMV-T7-3 for use in expressing the receptor in mammalian host cells and for use in generating in vitro transcripts of the DNA to be expressed in Xenopus oocytes.

Two additional mGluR5a constructs (mGluR5a2 and mGluR5a3) were prepared by modification of the 5' untranslated region of the first mGluR5a construct. The above-described mGluR5a construct contains seven potentially inappropriate ATG translation initiation codons in the 5' untranslated region that precedes the proposed translation initiation codon (nucleotides 370 to 372 of Sequence ID No. 7). The mGluR5a1 construct was digested with Bal3l to accomplish the following: (1) remove 255 nucleotides of sequence (nucleotides 1–255 of Sequence ID No. 7, containing six of the seven upstream ATG triplets), thereby creating mGluR5a2 and (2) remove 348 nucleotides of sequence (nucleotides 1–348 of Sequence ID No. 7, containing all upstream ATG triplets), thereby creating mGluR5a3. Thus, mGluR5a2 is identical to mGluR5a1 except that it lacks some of the 5' untranslated sequence and thus contains only one ATG triplet upstream of the proposed translation initiation codon. Similarly, mGluR5a3 is identical to mGluR5a1 except that it lacks all of the ATG triplets upstream of the proposed translation initiation codon and contains only 21 nucleotides of 5' untranslated sequence.

A third mGluR5a construct, MMTV-hmGluR5a, was prepared for use in MMTV promoter-regulated expression of mGluR5a as follows. mGluR5a3 was digested with XbaI. The 4.1 kb fragment containing the SV40 splice sites, the full-length mGluR5a coding sequence (plus 21 nucleotides of 5' untranslated sequence and 173 nucleotides of 3' untranslated sequence) and the polyadenylation signal was isolated, blunt-ended and ligated to a 2 kb EcoRI-NdeI (blunt-ended) fragment of pBR322 to create pBR-hmGluR5. Vector pMAMneo (Clontech, Palo Alto, Calif.), which contains the MMTV LTR promoter, and ampicillin and neomycin resistance genes, was digested with BamHI, to remove the neomycin resistance gene, and allowed to religate. The vector was then digested with EcoRI, and the fragment containing the ampicillin resistance gene was religated with the larger vector fragment in the reverse orientation to create pMAMneo⁻ampopp. This vector was digested with PstI/NheI, and the 2.3 kb fragment containing a 5' portion of the ampicillin resistance gene and the MMTV-LTR was isolated. Plasmid pBR-hmGluR5 was digested with PstI/XbaI, and the 5.3 kb fragment containing a 3' portion of the ampicillin resistance gene and the mGluR5a sequence (with SV40 splice sites and polyadenylation signal) was ligated with the 2.3 kb Pst/NheI fragment of pMAMneo⁻ampopp to create MMTV-hmGluR5a.

Thus, pMMTV-hmGluR5a contains the MMTV-LTR followed by SV40 splice sites in operative linkage with the mGluR5a DNA (containing nucleotides 349–4085 of Sequence ID No. 7) followed by a polyadenylation signal.

A fourth mGluR5a construct, pSV-hmGluR5, was prepared for use in SV40 promoter-regulated expression of mGluR5a as follows. mGluR5a3 was partially digested with XhoI, treated with Klenow and allowed to religate to itself, thereby destroying the XhoI site located 3' of the mGluR5a DNA. The plasmid was then digested with ScaI/XhoI, generating a fragment containing the SV40 splice sites, the full-length mGluR5a coding sequence (plus 21 nucleotides of 5' untranslated sequence and 173 nucleotides of 3' untranslated sequence), the polyadenylation signal and a 3' portion of the ampicillin resistance gene. Plasmid pSVβ (Clontech, Palo Alto, Calif.) was digested with ScaI/XhoI, and the fragment containing a 5' portion of the ampicillin resistance gene and the SV40 early promoter was ligated to the ScaI/XhoI fragment containing the mGluR5a DNA to create pSV-hmGluR5. Thus, pSV-hmGluR5 contains the SV40 early promoter followed by SV40 splice sites in operative linkage with the mGluR5a DNA (containing nucleotides 349–4085 of Sequence ID No. 7) followed by a polyadenylation signal.

To prepare a full-length mGluR5b construct, an mGluR5a construct (mGluR5al, mGluR5a2 or mGluR5a3) was digested with NheI/PmlI to release a fragment containing nucleotides 2725–3020 of Sequence ID No. 7. The remaining vector fragment was then ligated to the NheI/PmlI fragment isolated from METAB1. The resulting vector, mGluR5b, is identical to the mGluR5a construct from which it was prepared, except that it includes a 96 bp insertion (nucleotides 3000–3095 of Sequence ID No. 9) located between nucleotides 2999 and 3000 of Sequence ID No. 7. Sequence ID No. 9 is the complete nucleotide sequence of the full-length mGluR5b cDNA prepared from vector mGluR5a1.

To prepare a full-length mGluR5c construct, an mGluR5a construct (mGluR5a1, mGluR5a2 or mGluR5a3) is digested with NheI/HindIII (the HindIII site is present in the polylinker of the pCMV-T7-3 portion of the mGluR5a vector) to release a fragment containing nucleotides 2725–4085 of Sequence ID No. 7. The remaining vector fragment is then ligated to the NheI/HindIII fragment isolated from METAB2. The resulting full-length cDNA, mGluR5c (Sequence ID No. 11), is identical to the mGluR5a construct from which it was prepared for the first 2630 nucleotides of the coding sequence; however, at nucleotide 2631 of the coding sequence, the coding sequences of mGluR5c and mGluR5a diverge (e.g., beginning at nucleotide 3000 of Sequence ID No. 7) with the mGluR5c coding sequence having a guanine nucleotide as nucleotide 2631 of the coding sequence followed immediately by a translation termination codon (nucleotides 3001–3003 of Sequence ID No. 11).

B. mGluR1 Receptor cDNA cDNA Library Screening

The medium-insert cerebellum library was screened for hybridization to a fragment of the DNA encoding the rat mGluR1 receptor (nucleotides 1 to 3031 plus 5' untranslated sequence; see Masu et al. (1991) *Nature* 349:760–765). Hybridization was performed in 5× SSPE, 5× Denhart's solution, 50% formamide, 0.2% SDS, 200 µg/ml denatured, sonicated herring sperm DNA at 42° C. and washes were performed in 1× SSPE, 0.2% SDS at 55° C. Three hybridizing plaques, METAB7–METAB9, were identified.

In a subsequent round of screening, an independent plating of 1×10⁶ recombinants of the human medium-insert cerebellum cDNA library was probed for additional human mGluR1 clones. This plating was screened sequentially for hybridization first to a DNA fragment containing nucleotides 1–1256 (plus 5' untranslated sequence) of the rat mGluR1 cDNA (i.e., a 5' probe) and then to a DNA fragment containing nucleotides 2075–3310 of the rat mGluR1a cDNA (i.e., a 3' probe) using the same hybridization and wash conditions as those used in the previous screening that identified clones METAB7–METAB9. Three clones (METAB18, METAB21 and METAB22) were identified by hybridization to the 5' probe, and four clones (METAB14, METAB20, METAB32 and METAB35) were identified by hybridization to the 3' probe.

The 5' rat mGluR1 fragment was used as a probe to screen the large-insert human cerebellum cDNA library for further mGluR1 clones. Hybridization and wash conditions were essentially identical to those used in isolating the six mGluR1 clones from the medium-insert cerebellum library (except 20% formamide was used in the hybridization solution). Three plaques, METAB58, METAB59 and METAB60, hybridized to the probe.

Characterization of Isolated Clones

The inserts of the purified plaques were characterized by restriction enzyme mapping and DNA sequence analysis. METAB58 is ~2.8 kb and contains 5' untranslated sequence, a translation initiation codon and ~2.3 kb of coding sequence. The 3' end of METAB58 overlaps the 5' end of METAB14. METAB14 extends ~700 bp in the 3' direction and contains a translation termination codon. Thus, METAB58 and METAB14 overlap to encode a full-length mGluR1 receptor (see Sequence ID No. 1). The other clones are also partial mGluR1 cDNAs that contain nucleotide sequences from the portion of the mGluR1 coding sequence located between the translation initiation and termination codons.

To determine if additional clones encoding the 3' end of the human mGluR1 transcript were present in human cDNA libraries, the cDNAs from the hippocampus/basal ganglia and cerebellum libraries were subjected to nucleic acid amplification. The 5' primer consisted of nucleotides 2218 to 2240 of Sequence ID No. 1 whereas the 3' primer was a degenerate oligonucleotide based on amino acids 890–897 of the rat mGluR1a coding sequence (see Pin et al. (1992) *Neurobiology* 89:10331–10335). The products of the amplification were analyzed by gel electrophoresis. A single product (i.e., a 500 bp fragment) was detected in only the hippocampus/basal ganglia library.

To obtain additional clones representing the 3' end of the mGluR1 transcript, the hippocampus and cerebellum cDNA libraries can be screened (using conditions similar to those used for obtaining human mGluR1 cDNAs described above) with a fragment from the 3' end of the rat mGluR1a cDNA (e.g., the ~2 kb NcoI/ClaI fragment of the rat mGluR1a cDNA). This probe corresponds to a portion of the 3' region of the mGluR1 cDNA that does not appear to be alternatively spliced. Hybridizing clones are then analyzed by restriction mapping and DNA sequence analysis to determine if different 3' ends are represented.

Preparation of Full-Length mGluR1 cDNA Constructs

To prepare a full-length construct encoding the B form of the human mGluR1 receptor, portions of clones METAB58 and METAB14 are ligated. METAB58 is digested with EcoRI/AccI and the 2459 bp fragment containing nucleotides 154–2612 of Sequence ID No. 1 is isolated. The 704 bp fragment of METAB14 (containing nucleotides 2613–3321 of Sequence ID No. 1) is isolated by digestion of METAB14 with AccI/XhoI. This fragment is then ligated to the 2459 bp fragment of METAB58 and to EcoRI/SalI-digested vector pCMV-T7-3. The resulting construct encoding human mGluR1B contains 234 nucleotides of 5' untranslated sequence (nucleotides 154–387 of Sequence ID No. 1), the entire mGluR1B coding sequence (nucleotides 388–3108 of Sequence ID No. 1), and 213 nucleotides of 3' untranslated sequence (nucleotides 3109–3321 of Sequence ID No. 1). The mGluR1B-encoding sequence is operatively linked to the regulatory elements in pCMV-T7-3 for expression in mammalian cells.

Several methods can be employed to determine which mGluR5 and mGluR1 receptor variants are actually expressed in various human tissues. For example, oligonucleotides specific for the nucleotide sequences located 5' and 3' of the insertions/deletions (i.e., regions of divergence) of mGluR transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues. These assays are a sensitive method for detecting and quantitating an RNA species in a complex mixture of total cellular RNA. A portion of the mGluR DNA is labeled and hybridized with cellular RNA. If complementary MRNA is present in the cellular RNA, a DNA-RNA hybrid results.

The RNA sample is then treated with RNase, which degrades single-stranded RNA. Any RNA-DNA hybrids are protected from RNase degradation and can be visualized by gel electrophoresis and autoradiography.

Isolation of genomic clones containing human metabotropic receptor-encoding sequences by, for example, hybridization to the human mGluR cDNAs disclosed herein and subsequent characterization of the clones provides further information on possible splice variants of the mGluR primary transcripts.

C. mGluR3 Receptor cDNA cDNA Library Screening

A human hippocampus cDNA library (generated using random primers to prime cDNA synthesis and then selecting cDNAs that were 1.0–2.8 kb for ligation to λgt10 vectors) was screened for hybridization to a 500 bp SmaI/XbaI fragment of the rat mGluR2 cDNA and a 3 kb AccI-BamHI fragment of the rat mGluR3 cDNA [see Tanabe et al. (1992) Neuron 8:169–179]. Hybridization was performed in 5× SSPE, 5× Denhart's solution, 50% formamide, 0.2% SDS, 200 µg/ml denatured, sonicated herring sperm DNA at 42° C. and washes were performed in 0.5× SSPE, 0.2% SDS at 65° C. Three hybridizing plaques, METAB40, METAB41 and METAB45, were identified.

A portion of the 5' end of METAB45 (i.e., the first 244 bp; nucleotides 2634–2877 of Sequence ID No. 5) was then used to screen an amplified cerebellum library (generated using random primers to prime cDNA synthesis and then selecting cDNAs that were >2.8 kb for ligation to λgt10 vectors) and an amplified hippocampus cDNA library (generated using random primers to prime cDNA synthesis and then selecting cDNAs that were >2.0 kb for ligation to λgt10 vectors) for additional mGluR3 clones. One million clones from each library were screened. Hybridization and wash conditions were identical to those used in isolating METAB40, METAB41 and METAB45 from the hippocampus library. Three hybridizing plaques were identified in each library: METAB46, METAB49 and METAB50 in the cerebellum library and METAB47, METAB48 and METAB51B in the hippocampus library.

Characterization of Isolated Clones

The inserts of the purified plaques were characterized by restriction enzyme mapping and DNA sequence analysis. Each of the isolated clones are partial cDNAs encoding portions of the human mGluR3 receptor, except for clone METAB40, which encodes a portion of the human mGluR2 receptor (see Example 1.D.). Clones METAB41, METAB45 and METAB47–49 contain sequence from the 3' end of the mGluR3 coding sequence as well as a translation termination codon. Clones METAB46, METAB50 and METAB51B contain sequence from the 5' end of the mGluR3 cDNA, including a translation initiation codon, and varying amounts of 5' untranslated sequence.

Preparation of Full-Length mGluR3 cDNA Constructs

Four constructs containing the full-length human mGluR3 coding sequence were prepared by ligating portions of METAB48 and METAB46 or METAB51B. The full-length coding sequence is provided in Sequence ID No. 5 (nucleotides 1064–3703). The inserts of clones METAB46 and METAB51B were separately subcloned into pCMV-T7-3 as EcoRI fragments. The insert of clone METAB48 was subcloned as an EcoRI fragment into pCMV-T7-2.

To generate construct mGluR3B, the pCMV-T7-3 plasmid containing the METAB51B insert was digested with ScaI/BglII, and the 2.6 kb fragment containing the 5' half of the ampicillin resistance gene and a 5' portion of the METAB51B insert (nucleotides 748–1671 of Sequence ID No. 5) was isolated. This fragment was ligated to a 4.3 kb fragment isolated from a ScaI/BglII digest of the pCMV-T7-2 plasmid harboring the insert of METAB48 [the 4.3 kb fragment contains the 3' half of the ampicillin resistance gene and a 3' portion of METAB48 (nucleotides 1672–3919 of Sequence ID No. 5)]. The resulting construct, mGluR3B, contains 316 nucleotides of 5' untranslated sequence (nucleotides 748–1063 of Sequence ID No. 5), the entire mGluR3 coding sequence (nucleotides 1064–3703 of Sequence ID No. 5), and 216 nucleotides of 3' untranslated sequence (nucleotides 3704–3919 of Sequence ID No. 5). The mGluR3B-encoding sequence is operatively linked to the regulatory elements from vectors pCMV-T7-3 and pCMV-T7-2 for expression in mammalian cells.

To generate construct mGluR3C, the pCMV-T7-3 plasmid harboring the insert of METAB46 was digested with ScaI/BglII and the 3.4 kb fragment containing the 5' half of the ampicillin resistance gene and a 5' portion of METAB46 (nucleotides 1–1671 of Sequence ID No. 5) was isolated. This fragment was ligated to the same ScaI/BglII fragment of METAB48 as was used in construct mGluR3B. The resulting construct, mGluR3C, contains 1063 nucleotides of 5' untranslated sequence (nucleotides 1–1063 of Sequence ID No. 5), the entire mGluR3 coding sequence (nucleotides 1064–3703 of Sequence ID No. 5), and 216 nucleotides of 3' untranslated sequence (nucleotides 3704–3919 of Sequence ID No. 5). The mGluR3C-encoding sequence is operatively linked to the regulatory elements from vectors pCMV-T7-2 and pCMV-T7-3 for expression in mammalian cells.

Construct mGluR3A was generated by digesting mGluR3C with EcoRV and NotI to remove a fragment containing nucleotides 1–1035 of Sequence ID No. 5, making the NotI site blunt-ended and then allowing the larger vector fragment to re-ligate. Construct mGluR3A contains 28 nucleotides of 5' untranslated sequence (nucleotides 1036–1063 of Sequence ID No. 5), the entire mGluR3 coding sequence (nucleotides 1064–3703 of Sequence ID No. 5) and 216 nucleotides of 3' untranslated sequence (nucleotides 3704–3919 of Sequence ID No. 5). The mGluR3A-encoding sequence is operatively linked to the regulatory elements from vectors pCMV-T7-3 and pCMV-T7-2 for expression in mammalian cells.

To generate construct pSV-hmGluR3C (for use in SV40 promoter-regulated expression of mGluR3), the pCMV-T7-3 plasmid harboring the insert of METAB46 was digested with ScaI/NotI, and the fragment containing the 3' portion of the ampicillin resistance gene and the entire METAB46 insert was isolated. Plasmid pSVp was digested with ScaI/NotI, and the fragment containing the 5' portion of the ampicillin resistance gene and the SV40 early promoter and splice sites was ligated to the ScaI/NotI fragment from the pCMV-T7-3 vector harboring METAB46 to create pSV-METAB46. Plasmid pSV-METAB46 was digested with ScaI/BglII and the fragment containing the 5' portion of the ampicillin resistance gene, the SV40 early promoter and splice sites and a 5' portion of METAB46 (nucleotides 1–1671 of Sequence ID No. 5) was isolated. This fragment was ligated to the same ScaI/BglII fragment of METAB48 as was used in constructs mGluR3B and mGluR3C. The resulting construct, pSV-hmGluR3C, contains the SV40 promoter followed by SV40 splice sites in operative linkage with the mGluR3 DNA (containing nucleotides 1–3919 of Sequence ID No. 5) followed by a polyadenylation signal.

D. mGluR2 Receptor cDNA

Clone METAB40 was isolated from a human hippocampus cDNA library as described in Example 1.C. The insert cDNA of METAB40 is 1100 bp in length and encodes the 3' end of a human mGluR2 receptor, including a translation termination codon and 3' untranslated sequence. The first 355 nucleotides of METAB40 are provided in Sequence ID No. 3; the last 343 nucleotides of METAB40 (which are all from the 3' untranslated sequence) are provided in Sequence ID No. 13).

To isolate clones containing DNA representing the 5' portion of the mGluR2 transcript, the human hippocampus cDNA library can be screened for hybridization to an oligonucleotide corresponding to the 5' end of METAB40. Hybridizing plaques are purified and characterized by DNA sequence analysis. Clones that overlap with METAB40 and contain a translation initiation codon can be ligated to METAB40 at appropriate restriction sites to generate a full-length mGluR2-encoding cDNA construct.

EXAMPLE 2

Expression of Recombinant Human Metabotropic Glutamate Receptors in Oocytes

Xenopus oocytes were injected with in vitro transcripts prepared from constructs containing DNA encoding human metabotropic receptors. Electrophysiological measurements of the oocyte transmembrane currents were made using the two-electrode voltage clamp technique (see e.g., Stuhmer (1992) *Meth. Enzymol.* 207:319–339).

A. Preparation of In Vitro Transcripts

Recombinant capped transcripts of metabotropic receptor cDNAs contained in construct mGluR5a3 were synthesized from linearized plasmids using the Megascript Kit (Cat. #1334, Ambion, Inc., Austin, Tex.). The mass of each synthesized transcript was determined by UV absorbance and the integrity of each transcript was determined by electrophoresis through an agarose gel.

B. Electrophysiology

Xenopus oocytes were injected with 10–50 ng of metabotropic receptor transcripts per oocyte. The preparation and injection of oocytes were carried out as described by Dascal [(1987) *Crit. Rev. Biochem.* 22:317–387]. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3), and the membrane potential was clamped at −80 to −100 mV. Drugs were applied by pipetting 60 μl aliquots of drug-containing solution directly into the bath. Data were sampled at 2–5 Hz with a Labmaster data acquisition board in PC-386 using AXOTAPE version 1.2 (Axon Instruments, Foster City, Calif.) software. Data were exported to a laser printer or plotted using Sigmaplot version 5.0.

Metabotropic receptor-modulating compounds, i.e., 0.001–0.1 μM quisqualate, 0.1–10 μM glutamate and 0.1–300 μM 1S,3R-ACPD (1-amino-cyclopentyl-1,3-dicarboxylic acid), were applied to the bath and the transmembrane currents were recorded. Significant currents were detected after application of the compounds. Dose-response studies in which the currents measured after application of varying amounts of each compound were compared revealed that the current magnitude increased with increasing concentration of each compound. Analysis of these data enabled a calculation of $EC_{50}$ values for each compound which were used in determining the relative potencies of the compounds.

EXAMPLE 3

Recombinant Expression of Human Metabotropic Glutamate Receptor Subunits in Mammalian Cells Human embryonic kidney (HEK 293) and Chinese hamster ovary (CHO) cells (i.e, DG44 cells; see Urlaub et al. (1986) *Som. Cell. Molec. Genet.* 12:555) were transfected with DNA encoding human metabotropic receptors. Transfectants were analyzed for expression of metabotropic receptors using various assays, e.g., inositol phosphate ($IP_1$) assays, $Ca^{++}$-sensitive fluorescent indicator-based assays, and [$^3$H]-glutamate binding assays.

A. Transient Transfection of HEK 293 Cells

HEK 293 cells were transiently transfected with DNA encoding mGluR5a (constructs mGluR5a2 and mGluR5a3 and construct MMTV-hmGluR5a) receptors. Approximately $2 \times 10^6$ HEK cells were transiently transfected with 5–18 μg (or 0.18 μg in some transfections, see Example 3.C.2.) of the indicated plasmid according to standard $CaPO_4$ transfection procedures [see Wigler et al. (1979) *Proc. Natl. Acad. Sci. USA* 76:1373–1376]. In addition, 0.5–2 μg (or 0.18 μg in some transfections, see Example 3.C.2) of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the X-gal substrate [Jones (1986) *EMBO* 5:3133–3142]. Transfectants can also be analyzed for β-galactosidase expression by measurement of β-galactosidase activity [Miller (1972) in *Experiments in Molecular Genetics*, pp.352–355, Cold Spring Harbor Press].

HEK 293 cells that were transiently transfected with 5 μg of MMTV-hmGluR5A were co-transfected with 5 μg of pRShGR (ATCC accession no. 67200) which contains DNA encoding a glucocorticoid receptor operatively linked to the Rous Sarcoma virus (RSV) LTR promoter. Co-expression of glucocorticoid receptors in these cells should insure that induction of expression of the MMTV promoter-mGluR5a DNA occurs upon addition of glucocorticoid (e.g., dexamethasone) to the cells.

The efficiency of these transfections of HEK cells was typical of standard efficiencies (i.e., ~50%).

B. Stable Transfection of Mammalian Cells

Mammalian cells, such as HEK 293, Ltk$^-$ and CHO cells (e.g., DG44 cells), can be stably transfected using the calcium phosphate transfection procedure [*Current Protocols in Molecular Biology*, Vol. 1, Wiley Inter-Science, Supplement 14, Unit 9.1.1–9.1.9 (1990)]. When CHO cells are used as hosts, it is generally preferable to use the SV40 promoter to regulate expression of the human metabotropic receptor-encoding cDNA. Ten-cm plates, each containing $1-2 \times 10^6$ cells, are transfected with 1 ml of DNA/calcium phosphate precipitate containing approximately 5–10 μg of metabotropic receptor-encoding DNA and 0.5–1 μg of DNA encoding a selectable marker, for example, the neomycin-resistance gene (i.e., pSV2neo) for selection of HEK 293 transformants, the thymidine kinase gene for Ltk$^-$ cell transfectants, or the dihydrofolate reductase (dhfr) gene for selection of DG44 cell transformants. After ~14 days of growth in the appropriate selective media, colonies form and are individually isolated using cloning cylinders. The isolates are then subjected to limiting dilution and screened to identify those that express metabotropic receptors using, for example, methods described below.

C. Analysis of Transfectants

1. Fluorescent Indicator-Based Assays

Activation of G-protein-coupled metabotropic receptors by agonists leads to stimulation of the phosphatidylinositol (PI) hydrolysis/intracellular $Ca^{++}$ signalling pathway and/or the inhibitory cAMP cascade. Methods of detecting transient increases in intracellular calcium concentration can be applied to the analysis of functional expression of metabotropic receptors that are coupled to the PI hydrolysis/$Ca^{++}$ mobilization pathway or to both the PI hydrolysis/$Ca^{++}$ mobilization pathway and the inhibitory cAMP cascade. One method for measuring intracellular calcium levels relies on calcium-sensitive fluorescent indicators.

Calcium-sensitive indicators, such as fluo-3 and fura-2 (Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{++}$ concentration of cells containing the indicator can be expressed directly as an increase in fluorescence (or an increase in the ratio of the fluorescence at two wavelengths when fura-2 is used). An automated fluorescence detection system for assaying metabotropic receptors has been described in commonly assigned pending U.S. patent application Ser. No. 07/812,254 and corresponding PCT Patent Application No. US92/11090, both of which are hereby incorporated by reference herein. Additionally, fluorescence imaging techniques can be utilized to visualize intracellular $Ca^{++}$ oscillations.

HEK cells th at were transiently transfected with DNA encoding a human mGluR5a receptor were analyzed for expression of functional recombinant metabotropic receptors using the automated fluorescent indicator-based assay and the fluorescence imaging assay. Likewise, cells stably transfected with metabotropic receptor DNAs can also be analyzed for functional metabotropic receptors using these assay systems.

a. Automated Fluorescence Assay

Untransfected HEK 293 cells (or HEK 293 cells transiently transfected with PCMV-T7-3) and HEK 293 cells that had been transfected with mGluR5a-encoding DNA were plated in the wells of a 96-well microtiter dish (Nunc Catalog No. 1-6708, distributed by Alameda Industries, Escondido, Calif.) that had been precoated with poly-L-lysine at a density of $2 \times 10^5$ cells/well and loaded with fluo-3 by incubation for 2 hours at 20° C. in a medium containing 20 μM fluo-3, 0.2% Pluronic F-127 in HBS (125 mM NaCl, 5 mM KCl, 1.8 mM $CaCl_2$, 0.62 mM $MgCl_2$, 20 mM glucose, 20 mM HEPES, pH 7.4). The cells were then washed with assay buffer (i.e. HBS). The microtiter dish was then placed into a fluorescence plate reader (e.g., Fluoroskan II, Lab Products International, Ltd., Raleigh, N.C.), and the basal fluorescence of each well was measured and recorded before addition of metabotropic receptor-modulating compounds such as quisqualate, glutamate, trans-ACPD (1-amino-cyclopentane-1,3-dicarboxylic acid), 1S,3R-ACPD, AP3 (2-amino-3-phosphonopropionate) AP5 (2-amino-5-phosphonopentanoate), and CNQX (6-cyano-7-nitroquinoxaline-2,3-dione) to the wells. The fluorescence of the wells was monitored repeatedly (75 readings at 0.63-sec intervals) following addition of agonist.

In general, the fluorescence of the untransfected HEK 293 cells did not change after addition of any of these compounds. The fluorescence of HEK 293 cells transiently transfected with either the mGluR5a3 or MMTV-hmGluR5a constructs increased in response to application of glutamate, quisqualate, trans-ACPD, or 1S,3R-ACPD. The fluorescence increased to a peak value, then decreased over time to the basal level of fluorescence in cells prior to application of the compounds. The effects of AP3, AP5 or CNQX on glutamate-, quisqualate- or trans-ACPD-stimulated fluorescence increases in cells transfected with mGluR5a2 were also investigated. Neither of these compounds (AP3, AP5 or CNQX) inhibited the agonist-induced fluorescence increases in these cells.

Dose-response studies in which the peak fluorescence values measured after application of varying amounts of glutamate, quisqualate or 1S,3R-ACPD to cells transfected with mGluR5a3 were compared revealed that the magnitude of the peak fluorescence increased with increasing concentration of each compound. Analysis of these data enabled a calculation of $EC_{50}$ values for each compound which were used in determining the relative potencies of the compounds.

HEK 293 cells transiently co-transfected with MMTV-hmGluR5a and pRShGR (a glucocorticoid receptor construct) were also analyzed in the fluorescence assay. The fluorescence of these cells increased in response to 100 μM quisqualate; the peak response was greater when the cells were preincubated with dexamethasone (~1 M) for 16 hrs at 37° C. before being assayed.

b. Fluorescence imaging assay

HEK 293 cells that had been transiently transfected with mGluR5a3 and untransfected HEK 293 cells (control) were analyzed by digital video imaging in order to visualize metabotropic receptor-mediated changes in intracellular $Ca^{++}$ concentration. Transfectants ($4 \times 10^5$ cells per 35-mm culture dish with glass-insert bottom) were loaded with fura-2 by exposing the cells to 1 μM fura-2 (acetoxymethyl ester) for 25 min at room temperature in the dark. The cells were then washed three times with DMEM and four times with Ringer's (160 mM NaCl, 5 mM KCl, 2 mM $CaCl_2$, 1 mM $MgCl_2$, 11 mM glucose, 5 mM HEPES, pH 7.3) solution.

The transfectants and untransfected cells were then placed on the stage of an Axiovert 100 TV inverted microscope (Zeiss, Oberkochren, Germany) equipped with a 150 W xenon lamp as the UV light source. An Image 1 Fluor System (Universal Imaging, West Chester, Pa.) was used to control the alternate excitation of the cells at 340 and 380 nm (typically every 3 sec) through a 40× 1.3 N.A. oil immersion objective. Light emitted at greater than 510 nm was collected by a CCD 72 intensified CCD camera (MTI Dage, Michigan City, Ind.) and digitized. The background emitted light was subtracted from the 340 and 380 nm excitation images. The corrected values were used in calculating the 340/380 intensity ratio. These uncalibrated fura-2 ratio values were reliable indicators of changes in the intracellular $Ca^{++}$ concentration.

The uncalibrated fura-2 ratios were used to generate pseudocolor images with purple corresponding to resting intracellular $Ca^{++}$ concentration (~100 nM) and red to high intracellular $Ca^{++}$ concentration (~1 μM). For quantitative analysis, the average ratio value in a 12-by-12 pixel region over each cell was calculated by the software for each ratio image in an experiment and imported into a spreadsheet for further analysis and graphing.

To demonstrate that HEK 293 cells express the intracellular components required in receptor-mediated activation of the PI hydrolysis/$Ca^{++}$ mobilization pathway, transfectants and untransfected cells (which express endogenous G-protein-coupled muscarinic acetylcholine receptors) were exposed to 1 mM carbamylcholine (CCh; a muscarinic acetylcholine receptor agonist), and the cells were monitored for increases in intracellular $Ca^{++}$ concentration. Typically, a detectable increase in the intracellular $Ca^{++}$ concentration of the majority of the cells was observed in response to CCh addition in the imaging studies.

Both transfected and untransfected HEK 293 cells were also monitored for increases in intracellular $Ca^{++}$ concentration in response to 100 µM quisqualate. On average, the intracellular $Ca^{++}$ concentration of the untransfected cells did not change after exposure to quisqualate. In contrast, the intracellular $Ca^{++}$ concentration of 26.7±22.3% of the transfected cells increased in response to application of 100 µM quisqualate.

2. Phosphatidylinositol Hydrolyis ($IP_1$) Assays

Because activation of G-protein-coupled metabotropic receptors by agonists can lead to stimulation of the phosphatidylinositol (PI) hydrolysis pathway, methods of detecting increases in the products of PI hydrolysis (e.g., $IP_3$, $IP_2$ or $IP_1$) can be applied to the analysis of functional expression of metabotropic receptors that are coupled to the PI hydrolysis/$Ca^{++}$ mobilization pathway or to both the PI hydrolysis/$Ca^{++}$ mobilization pathway and the inhibitory cAMP cascade. One method for measuring $IP_1$ and/or $IP_2$ and/or $IP_3$ generated by hydrolysis of PI involves incorporation of [$^3$H]-myo-inositol into cell membrane phospholipids and subsequent separation of [$^3$H]-$IP_1$, [$^3$H]-$IP_2$ and [$^3$H]-$IP_3$, followed by quantitation of the radioactivity in each fraction, as follows.

HEK 293 cells that had been transiently transfected with mGluR5a3 were plated in 24-well microtiter plates at a density of $8\times10^5$ cells/well. After the cells were allowed to settle and adhere to the bottom of the plate for a few hours, 2 µCi of [$^3$H]-myo-inositol (Amersham catalog # PT6-271, Arlington Heights, Ill.; specific activity=17.7 Ci/mmol) was added to each well and incubated overnight at 37° C. The next day, the cells were examined under a Nikon Diaphot inverted microscope to assess the health of the cells morphologically as well as to determine if the wells contained a confluent layer of cells. Media was then aspirated and the cells were washed twice with 0.5 ml Krebs bicarbonate buffer [117.9 mM NaCl, 4.72 mM KCl, 2.54 mM $CaCl_2$, 1.18 mM $MgSO_4$, 1.19 mM $KH_2PO_4$, 25 mM $NaHCO_3$, 11.1 mM dextrose (equilibrated with 95% $O_2$, 5% $CO_2$, pH 7.4)]. The cells were incubated for 45 min. at room temperature. The buffer was then aspirated from each well and the cells were washed and incubated in 0.5 ml/well for 45 min at room temperature. The buffer was aspirated from each well, and the cells were then incubated for 20 min at 37° C. with 450 µl Krebs-bicarbonate buffer containing 10 mM LiCl instead of 10 mM NaCl (to block hydrolysis of $IP_1$ to inositol and inorganic phosphate) and 10 mM unlabeled myo-inositol.

To begin treatment of the cells with metabotropic receptor-modulating compounds, 50 µl of Krebs-bicarbonate buffer (control) or 10× the final concentration of the compound was added to each well and the incubation was continued for 40 min. Incubation was terminated by addition of 1 ml ice-cold methanol to each well.

In order to isolate $IP_1$ from the cells, the cells were removed from the plates by scraping with plastic pipette tips, and the cell suspension was transferred to 12×75 mm glass tubes. The tubes were thoroughly vortexed, and a 150-µl aliquot, i.e., one-tenth of the total volume, of each reaction mixture was transferred to another tube for protein determination. The water-soluble inositol phosphates were separated from the radiolabelled membrane phospholipids by extraction in 1 ml chloroform. The tubes were incubated at room temperature for 30 min before centrifugation at 500×g for 5 min at 4° C. The aqueous (top) layer containing the [$^3$H]-inositol phosphates was transferred to 10-ml syringes connected to Accell QMA SEP-PAK columns (Millipore; California), which were attached to an Amersham Super-separator apparatus that was modified to allow collection into 20-ml scintillation vials. Water (10 ml) was added to the cartridge to remove [$^3$H]-inositol precursor, followed by 4 ml 0.02 M triethylammonium hydrogen carbonated buffer (TEAB, Fluka; New York). To separately remove [$^3$H]-$IP_1$, [$^3$H]-$IP_2$ and [$^3$H]-$IP_3$ from the cartridge, 4 ml of 0.1 M TEAB, 4 ml of 0.3 M TEAB and 4 ml of 0.4 M TEAB were sequentially added to the cartridge and the separate eluate fractions were collected in large scintillation vials. Ecolume cocktail (15 ml; ICN; California) was added to each vial for subsequent scintillation counting to determine the amount of each IP in the separate fractions. Protein concentration was determined using the Bio-Rad Protein Micro-Assay (Bio-Rad, Richmond, Calif.).

HEK 293 cells transiently transfected with 18 µg of mGluR5a3 displayed relatively high basal levels of $IP_1$ when analyzed in this assay. However, HEK 293 cells transiently transfected with 0.18 µg of mGluR5a3 exhibited lower basal $IP_1$ levels and detectable increases in $IP_1$ levels when treated with 1 mM glutamate, 1 mM quisqualate or 1 mM 1S,3R-ACPD. The quisqualate-induced increase in $IP_1$ levels was not affected by 1 mM AP3.

Dose-response studies which compared the $IP_1$ levels measured after application of varying amounts of glutamate, quisqualate or 1S,3R-ACPD to cells transfected with mGluR5a3 revealed that $IP_1$ levels increased with increasing concentration of each compound. Analysis of these data enabled calculation of $EC_{50}$ values for each compound which were used in determining the relative potencies of the compounds.

3. Metabotropic Receptor Ligand Binding Assays

HEK cells transiently transfected with mGluR5a3 or with pUC19 (negative control) were analyzed for [$^3$H]-glutamate binding. Rat brain membranes were included in the binding assays as a positive control.

a. Preparation of Membranes i. Rat Forebrain Membranes

Rat forebrain membranes were prepared from rat brains as described by Schoepp et al. [(1992) Neurosci. Lett. 145:100]. Briefly, forebrains, consisting essentially of cerebral cortex, striatum and hippocampus, from ten rat brains were homogenized in 50 volumes of 30 mM ice-cold Tris-HCl containing 2.5 mM $CaCl_2$, pH 7.6 using a Polytron (Brinkman, Westbury, N.Y.). The homogenate was centrifuged at 30,000×g for 15 minutes at 4° C. The supernatant was discarded, the pellet was resuspended in 50 volumes of buffer using a Polytron and the suspension was centrifuged at 30,000×g for 15 min. This step was repeated twice. The pellet was resuspended in buffer and incubated at 37° C. for 30 min. The suspension was then centrifuged at 30,000×g for 15 min. at 4° C. This step was repeated three times. The final pellet was resuspended in 15 volumes of 50 mM Tris-HCl, pH 7.6, buffer, aliquoted, quick frozen and stored at −70° C.

ii. Membranes from Transfected and Untransfected HEK293 Cells

In order to prepare membranes from HEK 293 cells transfected with mGluR5a-encoding DNA or pUC19 (negative control), cells were scraped from the tissue culture plates, and the plates rinsed with 5 ml of PBS (phosphate-buffered saline: 137 mM NaCl, 2.7 mM KCl, 10 mM $Na_2HPO_4$, 1.7 mM $KH_2PO_4$). The cells were centrifuged at low speed in a table-top centrifuge, and the cell pellet was rinsed with PBS. The cell pellet was resuspended in 20 volumes of 50 mM Tris-HCl containing 0.5 mM PMSF, pH 7.6. The cells were homogenized on ice in a Dounce (teflon/glass) homogenizer using 10–20 strokes. The homogenate was centrifuged at 12,000×g for 30 min. at 4° C. The final membrane pellet was resuspended in 50 mM Tris-HCl containing 0.5 mM PMSF, pH 7.6. The membrane preparations were aliquoted, quick-frozen, and stored at −70° C. The protein concentration was determined using the method of Bradford [(1976) *Anal. Biochem.* 72:248].

b. [$^3$H]-Glutamate Binding Assays

Specific binding of [$^3$H]-glutamate to metabotropic receptors in rat forebrain membranes was determined basically as described by Schoepp et al. (supra). On the day of the assay, frozen homogenate was thawed and washed three times with 50 mM Tris-HCl, pH 7.6. The final pellet was resuspended in 50 mM Tris-HCl, pH 7.6. The protein concentration was determined using the method of Bradford [(1976) *Anal. Biochem.* 72:248]. The suspension was centrifuged at 30,000×g for 15 min. in order to be able to resuspend the pellet in the assay buffer (50 mM Tris-HCl, 0.5 mM PMSF, 0.1% BSA, pH 7.6) at a concentration of 1 mg/ml. The membrane suspension was incubated in triplicate with 10 or 100 nM [$^3$H]-glutamate (New England Nuclear, Boston, Mass.; catalog no. NET-490, specific activity=57.4 Ci/mmol) in a total volume of 0.5 ml assay buffer containing 100 μM NMDA (Sigma, St. Louis, Mo.), 100 μM AMPA and 100 μM kainate (Research Biochemicals Inc., Natick, Mass.) to block [$^3$H]-glutamate binding to ionotropic glutamate receptors and 100 μM SITS (Sigma, St. Louis, Mo.) to inhibit [$^3$H]-glutamate binding to chloride-dependent uptake sites for 45 min on ice. Bound radioactivity was separated from free radioactivity by centrifugation for 5 min. at 20,000×g (4° C.) in an SM-24 rotor (Sorvall, Wilmington, Del.). The pellets were washed twice with 5–6 ml of ice-cold 50 mM Tris-HCl buffer, pH 7.6. The pellets were solubilized by vortexing in 5 ml of Ecolume scintillation cocktail. The radioactivity was measured in a Beckman scintillation counter. The nonspecific binding observed in the presence of 1 mM glutamate was subtracted from the total binding in order to determine specific binding.

Specific binding of [$^3$H]-glutamate to membranes prepared from HEK 293 cells transfected with mGluR5a-encoding DNA or pUC19 was determined essentially as described for measuring binding to rat brain membranes with minor modifications. On the day of the assay, frozen homogenate was thawed and centrifuged in a MR-150 high-speed refrigerated microcentrifuge (Peninsula Laboratories, Inc., Belmont, Calif.). The pellet was washed twice with assay buffer (50 mM Tris-HCl, 0.5 mM PMSF, 0.1% BSA, pH 7.6), and the final pellet was resuspended in assay buffer at a concentration of 1 mg/ml. NMDA, AMPA and kainate were excluded from the assay mixture when HEK 293 cell membranes were being analyzed for [$^3$H]-glutamate binding.

Specific binding of [$^3$H]-glutamate to rat brain membranes was measured using 200 μg of membrane and 100 nM [$^3$H]-glutamate. The ratio of total-to-nonspecific binding was approximately 2:1.

Specific binding of [$^3$H]-glutamate to membranes prepared from HEK 293 cells transfected with mGluR5a3 or pUC19 was measured using 200 μg of membranes and 100 nM [$^3$H]-glutamate. The amount of specific binding to membranes prepared from HEK 293 cells transfected with mGluR5a3 was significantly higher than that to membranes prepared from HEK 293 cells transfected with pUC19. Competitive binding studies were conducted in which the amount of specific binding of [$^3$H]-glutamate to membranes prepared from HEK 293 cells transfected with mGluR5a3 in the presence of various concentrations of unlabeled glutamate was determined. $IC_{50}$ values were calculated from the data obtained in these studies.

4. Cyclic AMP (cAMP) Assays a. RIA-Based Assays

Because activation of some G-protein-coupled receptors results in decreases (as opposed to increases) in cAMP, assays that measure intracellular cAMP levels can also be used to evaluate recombinant human metabotropic receptors expressed in mammalian host cells. Mammalian cells transiently or stably transfected with human metabotropic receptor-encoding DNA or pUC19 (negative control) are plated in 24-well microtiter plates at a density of 5×10$^5$ cells/well and allowed to incubate overnight. The following day, cells are examined under a Nikon Diaphot inverted microscope to assess the health of the cells morphologically as well as to determine if the wells contain a confluent layer of cells. Media is then aspirated and the cells are washed twice with 0.5 ml Krebs bicarbonate buffer (same buffer used in the PI hydrolysis assay; see Example 3.C.2) containing 1 mM IBMX (3-isobutyl-1-methylxanthine; Sigma, St. Louis, Mo.) and 0.1% BSA. Alternatively, 1× PBS can be used in place of Krebs bicarbonate buffer. Each wash is followed with a 30-min incubation at 37° C. The buffer is aspirated from each well and the cells are then incubated for 20 min at 37° C. with 0.2 ml Krebs-bicarbonate buffer containing 1 mM IBMX and 0.1% BSA.

To begin treatment of the cells with metabotropic receptor-modulating compounds, 50 μl of Krebs-bicarbonate buffer, with or without 5× the final concentration of forskolin, is added to some of the cells (basal control) and 5× the final concentration of the compound plus 5× the final concentration of forskolin is added to some cells (test cells) and the incubation is continued for 15 min at 37° C. At the end of this 15-min period, the reaction is terminated by adding 25 μl of 1% Triton X-100 solution and the incubation is continued for another 10 min. The lysed cells plus the cell suspension are transferred to 12×75 mm polypropylene tubes with plastic pipette tips. Each well is rinsed with 75 μl of Krebs-bicarbonate buffer containing 1 mM IBMX and 0.1% BSA. The rinse is combined with the cell lysate. The cell lysate suspension is centrifuged at 2300×g for 5 min and the supernatant is assayed for cAMP levels using an RIA kit (Amersham Life Sciences catalog #TRK 432; Arlington Heights, Ill.).

b. Cyclic Nucleotide-Gated Channel-Based Assay

HEK293 cells were grown in monolayers (approximately 2×10$^6$ cells per 10 cm poly-D-lysine-coated plate) in Dulbecco's modified Eagle's medium (DMEM; Gibco) containing 5% defined supplemented calf serum (Hyclone) including 100 U/ml penicillin and 100 μg/ml streptomycin sulfate. The cells were transiently transfected by the calcium phosphate method (see Ausubel, et al., supra, pp 9.1.1–9.1.7) with 5 μg of pCMV-OCNA (containing DNA encoding the olfactory cyclic nucleotide-gated channel (see Dhallen et al., supra) linked to the CMV promoter, 2 μg pCMV-βgal (Clontech, Palo Alto, Calif.), and 13 μg pUC19 as a control plasmid. Vector PCMV-OCNA was constructed by isolating the olfactory cyclic nucleotide-gated channel-encoding DNA as ~3.0 kb EcoRI fragment from pBluescript KS and ligating the resulting fragment to EcoRI-digested pCMV-T7-3. Six hours after transfection, the calcium phosphate precipitate was washed off and cells fed with DMEM containing 10% dialyzed fetal bovine serum (Hyclone), 100 U/ml penicillin, 100 μg/ml streptomycin, and supplemented with 2 mM glutamine. Transfection efficiencies, as determined by measuring β-galactosidase activity, were 50–70%.

HEK cells transfected with olfactory cyclic nucleotide-gated channel DNA were incubated 24–48 hours before testing for function. The activity of the channels was first assessed electrophysiologically using inside-out membrane patches pulled from the transfected cells so that the concentration of cAMP reaching the cytoplasmic face could be controlled (see, e.g., *Single-Channel Recording*, Sakmann and Neher, eds., Plenum Press, N.Y. (1983)). The patch was exposed to $Ca^{++}/Mg^{++}$-free Ringer's solution on both surfaces. In one patch, a current was elicited by ramping the membrane potential from −100 to +100 mV in 2 seconds, in the presence of 1 mM cAMP. This result suggested that the channel was functionally expressed.

The transfectants were also analyzed by single-cell video imaging of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay was conducted essentially as described in Example 3.C.1.b., with some modifications. After dye loading, the cells were examined using a Zeiss Axiovert microscope and 100 W mercury lamp, a Dage intensified CCD camera, and Image-1 hardware and software for image processing. The software controlled the alternate excitation of the cells at 350 and 385 nm (typically every 5 seconds) through a 20×1.3 N.A. oil immersion objective. Light emitted at greater than 510 nm was collected by the CCD camera, digitized, and 350 and 385 nm excitation images were background-subtracted before calculating the 350/385 nm intensity ratio.

For quantitative analysis, the average 350/385 ratio value in a 12 by 12 pixel region over each cell was calculated by the software for each ratio image in an experiment and imported into a spreadsheet for further analysis and graphing. Fura-2 signals were calibrated with an intact cell in which $R_{min}$ was obtained by exposing the cells to Ringer's solution containing 10 μM ionomycin, 10 mM EGTA and no added $Ca^{++}$. $R_{max}$ was next obtained by exposing the cells to Ringer's solution containing 10 μM ionomycin and 10 mM $Ca^{++}$, with three washes. Using a $K_d$ of 250 nM for fura-2 inside living cells and the equation of Grynkiewicz et al. (*J. Biol. Chem.* 260:3440 (1985)), the resting $[Ca^{++}]_i$ was typically 100 nM.

In these experiments, the HEK293 cell transfectants were exposed to agents which increase intracellular cAMP levels and monitored for subsequent changes in $[Ca^{++}]_i$. There was a small increase in $[Ca^{++}]_i$ in the averaged results from 64 cells, and in individual cells in response to addition of 100 μM forskolin (activator of adenyl cyclase). A more significant increase was observed after addition of 1 mM IBMX (inhibitor of cAMP phosphodiesterase). In a control experiment, only 1 out of 64 untransfected HEK293 cells showed an increase in $[Ca^{++}]_i$ in response to elevation of intracellular cAMP levels. This response was transient and clearly different from the sustained response seen in HEK293 cells transfected with the cyclic nucleotide-gated channel DNA.

These results demonstrate that HEK cells expressing cyclic nucleotide-gated channels may be used as host cells in assays of receptors that cause a change in intracellular cyclic nucleotide levels when activated (e.g., metabotropic receptors).

5. Northern Blot Hybridization Analysis

Cells transfected with human metabotropic receptor-encoding DNA can also be analyzed for expression of the corresponding transcript by northern blot analysis. Total RNA was isolated from ~1×10⁷ cells that have been transfected with the human metabotropic receptor-encoding DNA, and 10–15 μg of RNA is used for northern hybridization analysis. The inserts from human metabotropic receptor-encoding plasmids are nick-translated and used as probes. Typical conditions for northern blot hybridization and washing are as follows:

hybridization in 5× SSPE, 5× Denhart's solution, 50% formamide, at 42° C. followed by washing in 0.2× SSPE, 0.1% SDS, at 65° C.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence (and the deduced amino acid sequence) of a DNA encoding a metabotropic glutamate receptor subtype (mGluR1B) of the present invention.

Sequence ID No. 2 is the deduced amino acid sequence of the nucleotide sequence of Sequence ID No. 1.

Sequence ID No. 3 is a nucleotide sequence (and the deduced amino acid sequence) of a partial clone encoding a portion of an human mGluR2 receptor subtype.

Sequence ID No. 4 is the amino acid sequence of a portion of an human mGluR2 receptor subunit as encoded by the nucleotide sequence of Sequence ID No. 3.

Sequence ID No. 5 is the nucleic acid sequence (and the deduced amino acid sequence) of a DNA encoding a metabotropic glutamate receptor subtype (mGluR3) of the present invention.

Sequence ID No. 6 is the deduced amino acid sequence of the nucleotide sequence of Sequence ID No. 5.

Sequence ID No. 7 is the nucleic acid sequence (and the deduced amino acid sequence) of a DNA encoding a metabotropic glutamate receptor (mGluR5a1) of the present invention.

Sequence ID No. 8 is the deduced amino acid sequence of the nucleotide sequence of Sequence ID No. 7.

Sequence ID No. 9 is the nucleic acid sequence (and the deduced amino acid sequence) of a DNA encoding an mGluR5 variant metabotropic glutamate receptor (mGluR5b) of the present invention.

Sequence ID No. 10 is the deduced amino acid sequence of the nucleotide sequence of Sequence ID No. 9.

Sequence ID No. 11 is the nucleic acid sequence (and the deduced amino acid sequence) of a DNA encoding an mGluR5 variant metabotropic glutamate receptor (mGluR5c) of the present invention.

Sequence ID No. 12 is the deduced amino acid sequence of the nucleotide sequence of Sequence ID No. 11.

Sequence ID No. 13 is 343 nucleotides of 3' untranslated sequence of an human mGluR2 receptor subtype.

That which is claimed is:

1. A cation-based bioassay for monitoring receptor-induced changes in intracellular cyclic nucleotide levels, said bioassay comprising:

introducing a polynucleic acid encoding a human metabotropic glutamate receptor into mammalian or Xenopus host cells, that contain at least one type of endogenous or recombinant cyclic nucleotide-gated channel, thereby producing modified host cells wherein said receptor is encoded by a polynucleotide that hybridizes under high stringency conditions to a nucleic acid encoding the amino acid sequence set forth in SEQ ID NO. 4 or SEQ ID NO. 6; and said receptor is expressed by said modified host cells; and measuring changes in the amount of cyclic nucleotide activation of said cyclic nucleotide-gated channels in the presence and absence of a potential ligand for said receptor.

2. bioassay of claim 1 wherein said receptor is encoded by a polynucleotide that hybridizes under high stringency conditions to a nucleic acid encoding the amino acid sequence set forth in SEQ ID NO. 4.

3. bioassay of claim 1 wherein said receptor is encoded by a polynucleotide that hybridizes under high stringency conditions to a nucleic acid encoding the amino acid sequence set forth in SEQ ID NO. 6.

4. The bioassay of claim 1 wherein said host cells are selected from the group consisting of COS cells, mouse L cells, Chinese hamster ovary cells, human embryonic kidney cells, African green monkey cells, Ltk– cells, BHK cells, and *Xenopus laevis* oocytes.

5. The bioassay of claim 1 wherein said polynucleic acid further comprises a promoter operatively linked to said polynucleic acid encoding said receptor, wherein said promoter is selected from the group consisting of SV40 promoters, cytomegalovirus promoters, mouse mammary tumor virus promoters, Rous sarcoma virus promoters, T7 bacteriophage promoters, and Moloney murine leukemia virus promoters.

6. The bioassay of claim 1 wherein said measuring step comprises electrophysiological measurement of ion flux currents, fluorescence measurement of intracellular calcium, or single cell video imaging.

7. The bioassay of claim 1 wherein said potential ligand is selected from the group consisting of quisqualate, glutamate, trans-1-amino-cyclopentane-1,3-dicarboxylic acid, 1S,3R-1-amino-cyclopentane-1,3-dicarboxylic acid, 2-amino-3-phosphonopropionate, 2-amino-5-phosphonopentanoate, and 6-cyano-7-nitroquinoxaline-2,3-dione.

8. The bioassay of claim 1 further comprising:
providing a second host cell that contains said cyclic nucleotide-gated channel, with the proviso that said second host cell does not express said receptor;
measuring changes in the amount of cyclic nucleotide activation of said cyclic nucleotide-gated channels in said second host cell in the presence and absence of said potential ligand; and
comparing said changes in the amount of cyclic nucleotide activation of said cyclic nucleotide-gated channels in said second host cell with the amount of cyclic nucleotide activation of said cyclic nucleotide-gated channels in said modified host cell.

9. A cation-based bioassay for monitoring receptor-induced changes in intracellular cyclic nucleotide levels, said bioassay comprising:
introducing a polynucleic acid encoding a human metabotropic glutamate receptor into mammalian or Xenopus host cells, that contain at least one type of endogenous or recombinant cyclic nucleotide-gated channel, thereby producing modified host cells, wherein said polynucleic acid hybridizes under high stringency conditions to the nucleic acid sequence set forth in SEQ ID NO. 3 or SEQ ID NO. 5; and said receptor is expressed by said modified host cells; and
measuring changes in the amount of cyclic nucleotide activation of said cyclic nucleotide-gated channels in the presence and absence of a potential ligand for said receptor.

10. The bioassay of claim 9 wherein said polynucleic acid hybridizes under high stringency conditions to the nucleic acid sequence set forth in SEQ ID NO:3.

11. The bioassay of claim 9 wherein said polynucleic acid hybridizes under high stringency conditions to the nucleic acid sequence set forth in SEQ ID NO:5.

12. The bioassay of claim 9 wherein said host cells are selected from the group consisting of COS cells, mouse L cells, Chinese hamster ovary cells, human embryonic kidney cells, African green monkey cells, Ltk– cells, BHK cells, and *Xenopus laevis* oocytes.

13. The bioassay of claim 9 wherein said polynucleic acid further comprises a promoter operatively linked to said polynucleic acid encoding said receptor, wherein said promoter is selected from the group consisting of SV40 promoters, cytomegalovirus promoters, mouse mammary tumor virus promoters, Rous sarcoma virus promoters, T7 bacteriophage promoters, and Moloney murine leukemia virus promoters.

14. The bioassay of claim 9 wherein said measuring step comprises electrophysiological measurement of ion flux currents, fluorescence measurement of intracellular calcium, or single cell video imaging.

15. The bioassay of claim 9 further comprising:
providing a second host cell that contains said cyclic nucleotide-gated channel, with the proviso that said second host cell does not express said receptor;
measuring changes in the amount of cyclic nucleotide activation of said cyclic nucleotide-gated channels in said second host cell in the presence and absence of said potential ligand; and
comparing said changes in the amount of cyclic nucleotide activation of said cyclic nucleotide-gated channels in said second host cell with the amount of cyclic nucleotide activation of said cyclic nucleotide-gated channels in said modified host cell.

* * * * *